US008691772B2

(12) United States Patent
Cohen et al.

(10) Patent No.: US 8,691,772 B2
(45) Date of Patent: Apr. 8, 2014

(54) HSP60, HSP60 PEPTIDES AND T CELL VACCINES FOR IMMUNOMODULATION

(75) Inventors: Irun R. Cohen, Rehovot (IL); Alexandra Zanin-Zhorov, Staten Island, NY (US); Guy Tal, Tel-Aviv (IL); Francisco Quintana, Buenos Aires (AR); Meirav Pevsner, Karmiel-Yosef (IL); Ofer Lider, Kfar Bilu B (IL); Osnat Lider, legal representative, Kfar Bilu B (IL); Lihi Lider, legal representative, Kfar Bilu B (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1045 days.

(21) Appl. No.: 11/813,333

(22) PCT Filed: Jan. 4, 2006

(86) PCT No.: PCT/IL2006/000014
§ 371 (c)(1),
(2), (4) Date: Mar. 4, 2009

(87) PCT Pub. No.: WO2006/072946
PCT Pub. Date: Jul. 13, 2006

(65) Prior Publication Data
US 2010/0003225 A1    Jan. 7, 2010

Related U.S. Application Data

(60) Provisional application No. 60/641,075, filed on Jan. 4, 2005, provisional application No. 60/679,647, filed on May 11, 2005.

(51) Int. Cl.
*A61K 38/00* (2006.01)
*C07K 7/08* (2006.01)

(52) U.S. Cl.
USPC ........................................ 514/21.4; 514/12.2

(58) Field of Classification Search
None
See application file for complete search history.

(56) References Cited

U.S. PATENT DOCUMENTS

| | | |
|---|---|---|
| 3,561,444 A | 2/1971 | Boucher |
| 3,699,963 A | 10/1972 | Zaffaroni |
| 3,703,173 A | 11/1972 | Dixon |
| 3,944,064 A | 3/1976 | Bashaw |
| 3,948,262 A | 4/1976 | Zaffaroni |
| 3,993,073 A | 11/1976 | Zaffaroni |
| 4,073,943 A | 2/1978 | Wretlind |
| 4,168,308 A | 9/1979 | Wretlind |
| 4,226,848 A | 10/1980 | Nagai |
| 4,309,404 A | 1/1982 | DeNeale |
| 4,309,406 A | 1/1982 | Guley |
| 4,556,552 A | 12/1985 | Porter |
| 4,624,251 A | 11/1986 | Miller |
| 4,635,627 A | 1/1987 | Gam |
| 4,704,295 A | 11/1987 | Porter |
| 4,713,243 A | 12/1987 | Schiraldi |
| 4,837,027 A | 6/1989 | Lee |
| 4,917,895 A | 4/1990 | Lee |
| 4,940,587 A | 7/1990 | Jenkins |
| 5,110,597 A | 5/1992 | Wong |
| 5,114,844 A | 5/1992 | Cohen |
| 5,141,750 A | 8/1992 | Lee |
| 5,151,272 A | 9/1992 | Engstrom |
| 5,284,660 A | 2/1994 | Lee |
| 5,356,635 A | 10/1994 | Raman |
| 5,371,109 A | 12/1994 | Engstrom |
| 5,405,619 A | 4/1995 | Santus |
| 5,578,303 A | 11/1996 | Cohen |
| 5,671,848 A | 9/1997 | Cohen |
| 5,736,146 A | 4/1998 | Cohen |
| 5,780,034 A | 7/1998 | Cohen |
| 5,958,416 A | 9/1999 | Birnbaum |
| 5,961,970 A | 10/1999 | Lowell |
| 5,993,803 A | 11/1999 | Cohen |
| 6,180,103 B1 | 1/2001 | Cohen |
| 2002/0146759 A1 | 10/2002 | Albani |
| 2003/0190323 A1 | 10/2003 | Cohen |
| 2004/0005588 A1 | 1/2004 | Cohen |

FOREIGN PATENT DOCUMENTS

| | | |
|---|---|---|
| EP | 259013 B2 | 6/1991 |
| EP | 262710 B2 | 8/1992 |
| EP | 322990 B2 | 3/1994 |

(Continued)

OTHER PUBLICATIONS

Bogdanos et al. "Autoimmune Hepatitis: An Update on Current Animal Models" Open Pathology Journal. 2008, 284(2):39-45).*
Achiron et al., "T cell vaccination in multiple sclerosis relapsing-remitting nonresponders patients", Clin. Immunol, 113:155-160 (2004).
Alexander W et al., "Suppressors of cytokine signaling (SOCS): negative regulators of signal transduction" J Leukoc Biol, 66:588-592 (Oct. 1999).
Anderton et al., "Differential Mycobacterial 65-kDa Heat Shock Protein T Cell Epitope Recognition after Adjuvant Arthritis-Inducing or Protective Immunization Protocols", J Immunol, 152:3656-3664 (1994).

(Continued)

Primary Examiner — Daniel E Kolker
Assistant Examiner — James Rogers
(74) Attorney, Agent, or Firm — Rodney J. Fuller; Booth Udall Fuller, PLC

(57) ABSTRACT

The present invention provides novel uses for peptide p277—positions 437-460 of human heat shock protein 60 (HSP60)—in modulation of immune responses and inflammatory diseases. The invention further provides novel uses for HSP60 and p277 in the treatment or prevention of hepatic disorders. The invention discloses methods for treating, preventing or ameliorating the symptoms of T cell mediated inflammatory and autoimmune disorders, including hepatic disorders, which comprise administering to a subject in need thereof a composition comprising as an active ingredient an effective quantity of a molecule selected from: HSP60, p277, fragments, analogs, homologs and derivatives thereof, and nucleic acids encoding same. Also disclosed are T cell vaccination methods for treating or preventing T cell mediated disorders.

6 Claims, 44 Drawing Sheets

(56) References Cited

FOREIGN PATENT DOCUMENTS

| EP | 354742 B2 | 3/1994 |
|---|---|---|
| EP | 205282 B2 | 9/1995 |
| EP | 516141 B2 | 8/1996 |
| EP | 417271 B2 | 12/1998 |
| IL | 94241 B2 | 3/1996 |
| WO | 85/02092 A1 | 5/1985 |
| WO | 89/12455 A1 | 12/1989 |
| WO | 91/02542 A1 | 3/1991 |
| WO | 92/04049 A1 | 3/1992 |
| WO | 94/02509 A1 | 2/1994 |
| WO | 94/29459 A1 | 12/1994 |
| WO | 95/11011 A1 | 4/1995 |
| WO | 95/15191 A1 | 6/1995 |
| WO | 95/25744 A1 | 9/1995 |
| WO | 96/10039 A1 | 4/1996 |
| WO | 96/16083 A1 | 5/1996 |
| WO | 96/18646 A2 | 6/1996 |
| WO | 96/19236 A1 | 6/1996 |
| WO | 97/01959 A1 | 1/1997 |
| WO | 97/02016 A2 | 1/1997 |
| WO | 97/11966 A1 | 4/1997 |
| WO | 00/27870 A1 | 5/2000 |
| WO | 01/43691 A2 | 6/2001 |
| WO | 02/16549 A2 | 2/2002 |
| WO | WO 02062959 A2 * | 8/2002 |
| WO | 03/063759 A2 | 8/2003 |
| WO | 03/070761 A1 | 8/2003 |
| WO | 03/096967 A2 | 11/2003 |
| WO | 2004/089280 A2 | 10/2004 |
| WO | 2004/098489 A2 | 11/2004 |
| WO | 2005/048914 A2 | 6/2005 |

OTHER PUBLICATIONS

Ben-Nun et al., "Vaccination against autoimmune encephalymyelitis with T-lymphocite line cells reactive against myelin basic protein", Nature 292:60-61 (Jul. 2, 1981).
Caramalho I. et al., "Regulatory T cells selectively express toll-like receptors and are activated by lipopolysaccharide", J Exp Med, 197(4):403-411 (Feb. 17, 2003).
Chedid et al., "Cell-Mediated Hepatic Injury in Alcoholic Livery Disease", Gastroenterology, 105:254-266 (1993).
Elias et al., "Hsp60 Peptide Therapy of NOD Mouse Diabetes Induces a Th2 Cytokine Burst and Downregulates Autoimmunity to Various B-Cell Antigens", Diabetes, 46:758-764 (1997).
Ferris et al., "Mitogen and lymphokine stimulation of heat shock proteins in T lymphocytes", Proc Natl Acad Sci U S A, 85:3850-3854 (Jun. 1988).
Gao et al., "Recombinant Human Heat Shock Protein 60 Does Not Induce the Release of Tumor Necrosis Factor a from Murine Macrophages", J. Biol Chem, 278(25):22523-22529 (2003).
Heneghan et al., "Current and Novel Immunosuppressive Therapy for Autoimmune Hepatitis", Hepatology, 35:7-13 (2002).
Holoshitz et al., "Lines of T Lymphocytes Induce or Vaccinate Against Autoimmune Arthritis", Science, 219:56-58 (Jan. 7, 1983).
Hu et al., "Experimental mucosal induction of uveitis with 60-kDa heat shock protein-derived peptide 336-351", Eur. J. Immunol., 28:2444-2455 (1998).
Kol et al., "Chlamydial Heat Shock Protein 60 Localizes in Human Atheroma and Regulates Macrophage Tumor Necrosis Factor-a and Matrix Metalloproteinase Expression", Circulation, 98:300-307 (1998).
Kol et al., "Chlamydial and human heat shock protein 60s activate human vascular endothelium, smooth muscle cells, and macrophages", J Clin Invest, 103:571-577 (1999).
Kollet O et al., "Rapid and efficient homing of human CD34+CD38{-}/lowCXCR4+ stem and progenitor cells to the bone marrow and spleen of NOD/SCID and NOD/SCID/B2mnull mice", Blood 97:3283-3291 (2001).
Laplante et al., "Expression of Heat Shock Proteins in Mouse Skin During Wound Healing", J Histochem Cytochem 46 (11):1291-1301 (1998).

Mor et al., "T Cells in the Lesion of Experimental Autoimmune Encephalomyelitis", J Clin Invest, 90:2447-2455 (1992).
Mosmann, T, "Rapid Colorimetric Assay for Cellular Growth and Survival: Application to Proliferation and Cytotoxicity Assays", J Immunol Methods, 65(1-2):55-63 (1983).
Ohashi et al., "Cutting Edge: Heat Shock Protein 60 is a Putative Endogenous Ligand of the Toll-Like Receptor-4 Complex", J Immunol, 164:558-561 (2000).
Ponomaryov T.et al., "Induction of the chemokine stromal-derived factor-1 following DNA damage improves human stem cell function", J Clin Invest, 106(11):1331-1339 (Dec. 2000).
Quintana et al., "Vaccination with Empty Plasmid DNA or CpG Oligonucleotide Inhibits Diabetes in Nonobese Diabetic Mice: Modulation of Spontaneous 60-kDa Heat Shock Protein Autoimmunity", J Immunol, 165:6148-6155 (2000.
Quintana et al., "DNA Vaccination with Heat Shock Protein 60 Inhibits Cyclophosphamide-Accelerated Diabetes", J Immunol, 169:6030-6035 (2002).
Quintana et al., "Inhibition of Adjuvant Arthritis by a DNA Vaccine Encoding Human Heat Shock Protein 60", J Immunol 169:3422-3428 (2002).
Quintana et al., "DNA Fragments of the Human 60-kDa Heat Shock Protein (HSP60) Vaccinate Against Adjuvant Arthritis: Identification of a Regulatory HSP60 Peptide", J Immunol, 171:3533-3541 (2003).
Ragno et al., "Protection of Rats from Adjuvant Arthritis by Immunization with Naked DNA Encoding for Mycobacterial Heat Shock Protein 65", Arthritis Rheum, 40:277-283 (1997).
Raz et al., "B-cell function in new-onset type 1 diabetes and immunomodulation with a heat-shock protein peptide (DiaPep277): a randomised, double-blind, phase II trial", Lancet 358:1749-1753 (Nov. 24, 2001).
Reizis et al., "The peptide binding specificity of the MHC class II I-A molecule of the Lewis rat, RT1.B", Int Immunol, 8 (12):1825-1832 (1996).
Rosen et al., "Frequencies of HCV-Specific Effector CD4+ T Cells by Flow Cytometry: Correlation with Clinical Disease Stages", Hepatology, 35:190-198 (2002).
Starr R. et al., "A family of cytokine-inducible inhibitors of signalling", Nature, 387:917-921 (Jun. 26, 1997).
Stribling et al., "Aerosol gene delivery in vivo", Proc. Natl. Acad. Sci. USA, 189:11277-11281 (Dec. 1992).
Tiegs et al., "A T Cell-dependent Experimental Liver Injury in Mice Inducible by Concanavalin A", J. Clinic. Invest., 90:196-203 (Jul. 1992).
Van Eden et al., "Cloning of Mycobacterial Epitope Recognized by T Lymphocytes in Adjuvant Arthritis", Nature, 331:171-173 (Jan. 14, 1988).
Wallin et al., "Heat-shock proteins as activators of the innate immune system", Trends Immunol, 23(3):130-135 (Mar. 2002).
Wang et al., "T-Cell Antigen Receptor Peptides Inhibit Signal Transduction within the Membrane Bilayer", Clin. Immunol., 105(2):199-207 (Nov. 2002).
Wolff et al., "Direct Gene Transfer into Mouse Muscle in Vivo", Science, 247:1465-1468 (Mar. 23, 1999).
Xu et al., "Serum Soluble Heat Shock Protein 60 is Elevated in Subjects with Atherosclerosis in a General Population", Circulation, 102:14-20 (2000).
Yokota et al., "Autoantibodies against chaperonin CCT in human sera with rheumatic autoimmune diseases: coomparison with antibodies against other Hsp60 family proteins", Cell Stress Chaperones, 5(4):337-346 (2000).
Zanin-Zhorov et al., "T cells respond to heat shock protein 60 via TLR2: activation of adhesion and inhibition of chemokine receptors", Faseb J, 17:1567-9 (2003).
Zanin-Zhorov et al., "Fibronectin-Associated Fas Ligand Rapidly Induces Opposing and Time-Dependent Effects on the Activation and Apoptosis of T Cells", J Immunol, 171:5882-5889 (2003).
Cohen et al., "Tregs in T cell vaccination: exploring the regulation of regulation," The Journal of Clinical Investigation, 114(9): 1227-1232 (2004).

(56) References Cited

OTHER PUBLICATIONS

Macht et al., "Relationship between disease severity and responses by blood mononuclear cells from patients with rheumatoid arthritis to human heat-shock protein 60," Immunology, 99(2): 208-214 (2000).
Van Eden et al., "Heat-shock proteins induce T-cell regulation of chronic inflammation," Nature Reviews Immunology 2005, 5: 318-330.
Zanin-Zhorov et al., "Heat shock protein 60 enhances CD4+ CD25+ regulatory T cell function via innate TLR2 signaling," J Clin Invest., 116(7): 2022-2032 (2006).
International Application No. PCT/IL06/00014 International Search Report Sep. 29, 2010.
Yamashita et al., "Apolipoprotein A-H Suppressed Concanavalin A-Induced Hepatitis via the Inhibition of CD4 T Cell Function," J. Immunol., 186: 3410-3420 (2011).

* cited by examiner

|  | TLR2 (% cells±S.D.) | TLR4 (% cells±S.D.) |
|---|---|---|
| $CD4^+$ | 67%±8 | 20%±4 |
| $CD4^+CD25^+$ | 75%±11 | 15%±7 |
| $CD4^+CD25^-$ | 62%±9 | 19%±5 |
Figure 19D
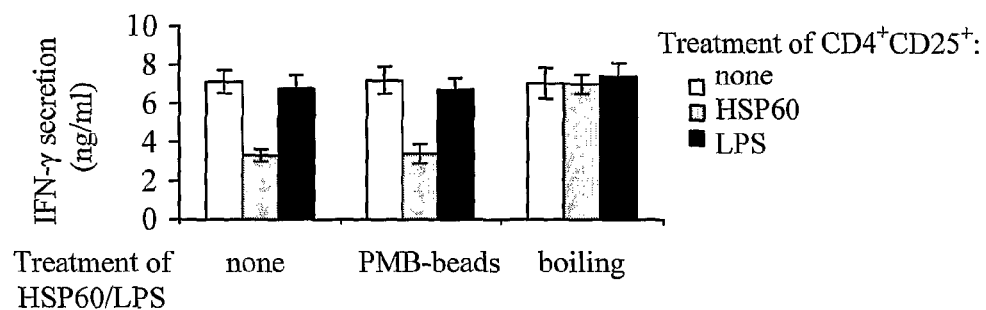
Figure 19E
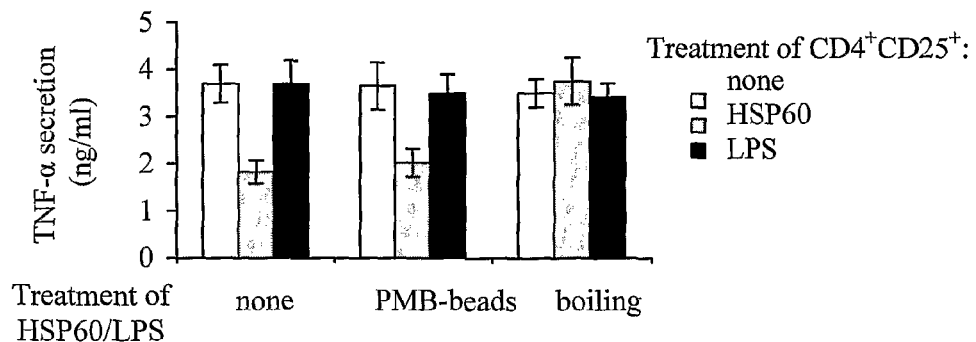
Figure 19F
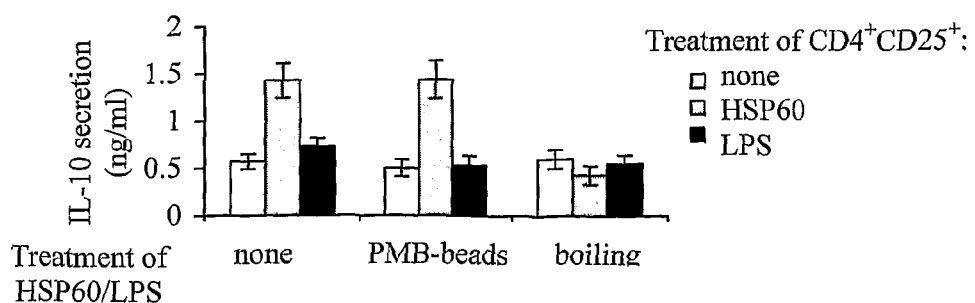
Figure 19G

HSP60, HSP60 PEPTIDES AND T CELL VACCINES FOR IMMUNOMODULATION

RELATED APPLICATION DATA

This application is the U.S. national stage of PCT/IL2006/000014 filed on Jan. 4, 2006, which is based on and claims the benefit of U.S. Provisional Patent Application Nos. 60/679,647 filed on May 11, 2005 and 60/641,075 filed on Jan. 4, 2005, the content of each which is expressly incorporated herein in its entirety by this reference.

FIELD OF THE INVENTION

The invention relates to the use of heat shock protein 60 (HSP60) and the HSP60-derived peptide p277, fragments, analogs, derivatives and salts thereof, nucleic acids encoding same and T cell vaccines thereof, in modulation of immune responses and T cell mediated inflammatory diseases.

BACKGROUND OF THE INVENTION

While the normal immune system is closely regulated, aberrations in immune response are not uncommon. A wide variety of medical treatments thus require regulation of the immune response in a patient. For example, T cell-mediated inflammatory diseases are known, in which an inappropriate T cell response is a component of the disease. These include both diseases mediated directly by T cells, and diseases in which an inappropriate T cell response contributes to the production of abnormal antibodies. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly affect such autoimmune pathologies.

Heat Shock Proteins and Immunity

During their migration into inflammatory sites, T cells interact with tissue components and encounter a variety of immuno-modulators, including cytokines, chemokines, acute phase proteins, and heat shock proteins (HSP). In addition to serving as a chaperone inside the cell, HSP60 is expressed by cells exposed to stress (Wallin et al., 2002, Kol et al., 1999) or immune activation (van Eden et al., 1988), and is present in the blood and tissues during inflammation (Yokota et al., 2000; Xu et al., 2000; Laplante et al., 1998; Ohashi et al., 2000, Hu et al., 1998; Mor et al., 1992). HSP60 is also involved as an autoantigen in type 1 diabetes and arthritis, and appeal's to down-regulate inflammation in models of these autoimmune diseases (Elias et al., 1997, Quintana et al., 2002, van Eden et al., 1988).

Numerous disclosures claim uses of heat shock proteins or fragments thereof as immune modulators in diagnosis, treatment or prevention of autoimmune diseases. Many of these disclosures relate to the human HSP60 or to its bacterial equivalent HSP65, or fragments thereof.

For example, the particular protein produced by the human body during development of Insulin Dependent Diabetes Mellitus (IDDM, type 1 diabetes), which serves as a diagnostic marker for the incipient outbreak of IDDM, is the human heat shock protein having a size of about 62 kD (human HSP60) or an antigen cross reactive therewith as disclosed in EP 0417271, and in U.S. Pat. Nos. 5,114,844, 5,578,303, 5,671,848, and 5,780,034. The p277 peptide, being the epitope of the human HSP60 involved in IDDM and corresponding to positions 437-460 of the human HSP60 sequence (SEQ ID NO:1), was first described in Israeli Patent No. 94241 of the present applicant. It has been disclosed that fragments of this HSP60 protein, including p277 and derivatives thereof, may serve as therapeutically useful entities in preventing or alleviating IDDM (U.S. Pat. No. 6,180,103, WO 96/19236, and WO 97/01959).

WO 89/12455 and WO 94/29459 disclose the use of stress proteins and analogs for producing or enhancing an immune response or for inducing immune tolerance, for prophylaxis or therapy of autoimmune diseases and for treating or preventing infections or cancers. A fusion protein is claimed comprising a stress protein fused to a protein against which an immune response is desired.

WO 95/25744 discloses microbial stress protein fragments containing epitopes homologous to related mammalian epitopes—used to treat and prevent inflammatory autoimmune diseases and to prevent transplant rejection. The protective epitopes are located in short peptides comprising sequences of 5-15 amino acids of stress proteins that are highly conserved between microorganisms and animals.

WO 97/11966 and WO 96/10039 disclose polypeptides of up to 21 amino acids derived from microbial heat shock protein, which are useful for prophylaxis or treatment of autoimmune diseases especially arthritis.

WO 96/16083 discloses a peptide 25 amino acids long, derived from the 10 kD heat shock protein (HSP10) of *Mycobacterium tuberculosis*, which is useful in pharmaceutical products for the treatment of inflammatory pathologies, especially rheumatoid arthritis.

WO 91/02542 discloses the use of antigenic and/or immuno-regulatory material derived from *Mycobacterium vaccae* and specifically HSP60, for treating chronic inflammatory disorders caused or accompanied by an abnormally high release of IL-6 and/or TNF-α.

WO 96/18646 discloses peptides of 9-20 amino acids derived from Mycobacterial HSP60 used for treatment or prevention of autoimmune CNS diseases, e.g. multiple sclerosis, chronic inflammatory CNS disease and primary brain tumors.

WO 94/02509 discloses peptides of 7-30 amino acids derived from DR3-restricted epitope of Mycobacterial HSP60 used for treatment of HLA-DR3 related autoimmune diseases.

U.S. Pat. No. 5,958,416 describes heat shock protein peptides and methods for modulating autoimmune central nervous system diseases.

EP 262710 of Cohen et al. discloses the use of HSP65, or fragments thereof for the preparation of compositions for the alleviation, treatment and diagnosis of autoimmune diseases, especially arthritic conditions. EP 322990 of Cohen et al. discloses that a polypeptide having amino acid sequence 172-192 of HSP65 is capable of inducing resistance to autoimmune arthritis and similar autoimmune diseases. WO 92/04049 of Boog et al. discloses peptides derived from *Mycobacterium tuberculosis* protein HSP65 containing at least 7 amino acid residues that inhibit antigen recognition by T lymphocytes in treatment of arthritis and organ rejection. The use of p277 in the treatment of arthritic conditions has not been disclosed previously.

WO 02/16549 of Cohen et al. relates to DNA vaccines useful for the prevention and treatment of ongoing autoimmune diseases. The compositions and methods of the invention feature the CpG oligonucleotide, preferably in a motif flanked by two 5' purines and two 3' pyrimidines. The vaccines optionally further comprise DNA encoding a peptide or a polypeptide selected from the group consisting of HSP60, p277 or p277 valiants. That disclosure is directed to methods and compositions for the ameliorative treatment of ongoing autoimmune disease in general and Insulin Dependent Diabetes Mellitus (IDDM) in particular.

WO 03/096967 of Cohen et al. discloses DNA vaccines encoding HSP60, HSP70 or HSP90 and active fragments thereof for the treatment of autoimmune diseases such as arthritis.

U.S. Pat. No. 5,993,803 discloses that when HSP60, p277, or other peptides and analogs thereof, are administered in a recipient subject before transplantation of an organ or tissue, autoimmunity to HSP60 is down-regulated, resulting in the prevention or suppression of graft rejection of the transplanted organ or tissue.

WO 00/27870 of Naparstek and colleagues discloses a series of related peptides derived from heat shock proteins HSP65 and HSP60, their sequences, antibodies, and use as vaccines for conferring immunity against autoimmune and/or inflammatory disorders such as arthritis. These peptides are intended according to that disclosure to represent the shortest sequence or epitope that is involved in protection of susceptible rat strains against adjuvant induced arthritis. These sequences further disclose what the inventors identify as the common "protective motif".

WO 01/43691 provides peptides and peptide analogs capable of acting as antagonists of HSP60 characterized in that they have the ability to reduce or prevent the induction of a pro-inflammatory response of cells of the innate immune system by HSP60.

Apart from the disclosures utilizing the role of HSP60 as an autoantigen involved in the progression of various autoimmune diseases for modulating the development of such diseases, other recent disclosures indicate that HSP60, via Toll-like receptor 2 (TLR-2), may directly inhibit T-cell migration in response to CXCL12 (SDF-lα), and the expression of its receptor, CXCR4 (Zanin-Zhorov et al., 2003). WO 03/070761 of Cohen et al provides novel conjugates comprising HSP60 peptides and their uses in treating immune conditions, particularly inflammatory conditions and autoimmune diseases. These conjugates comprise as a first part an HSP60 epitope that is capable of reacting via TLR2 on T cells and as a second segment a specific peptide capable of eliciting a reaction via a T cell receptor (TcR). Conjugates comprising p277 and a suitable TcR epitope were suggested for the therapy of various diseases, depending on the identity of the TcR epitope.

WO 03/063759 discloses peptides and peptide analogs of heat shock proteins capable of interacting directly with dendritic cells, and pharmaceutical compositions comprising dendritic cells exposed to such peptides and analogs, exemplified by a p277 analog, useful for prevention or treatment of inflammatory disorders and autoimmune diseases or malignancies, viral infections and allergy.

WO 04/098489 discloses HSP60 epitopes capable of binding to LPS or to macrophages and pharmaceutical compositions comprising these novel compounds, useful for prevention or treatment of inflammatory and autoimmune diseases and disorders.

WO 2005/048914, published after the priority dates of the present invention, discloses recombinant constructs encoding active fragments of HSP60, which are effective in treating T cell-mediated inflammatory autoimmune diseases by DNA vaccines. The HSP60 fragments of the disclosed invention are identified by their ability to react with T cells isolated from an animal vaccinated with DNA constructs encoding HSP70 to induce Th2/3 T-cell responses.

None of the background art demonstrates, however, that p277 and analogs thereof may be used to down-regulate T cell mediated inflammation irrespective of the involvement of HSP60 as an autoantigen contributing to the development of the pathology, and without being conjugated to or administered with a second TcR antigen.

Hepatitis

Hepatitis is an inflammatory disease that predominantly affects the liver. The disease is characterized by the initial onset of symptoms such as anorexia, nausea, vomiting, fatigue, malaise, arthralgias, myalgias, and headaches, followed by the onset of jaundice. The disease may also be characterized by increased serum levels of liver aminotransferases aspartate aminotransferase (AST) and alanine aminotransferase (ALT); Quantification of these enzymes in serum indicates the extent of liver damage.

Infectious, autoimmune, as well as non-infectious processes such as chemicals, are among the causes of hepatitis. Examples of infectious diseases affecting the liver include, but are not limited to: (i) viral hepatitis, e.g., hepatitis A, B, C, D, E, and G and (ii) parasitic hepatitis, e.g., *Schistosoma mansoni, Schistosoma hematobium*, and *Schistosoma japonicum*. Examples of noninfectious diseases affecting the liver include, but are not limited to, autoimmune diseases, such as autoimmune hepatitis and primary biliary cirrhosis. Other forms of noninfectious hepatitis are caused by hepatotoxic agents such as alcohol, drugs and toxins. Regardless of whether the attack on the liver is infectious, autoimmune or noninfectious, the liver responds to injury by recruiting inflammatory cells into the site of attack. T cells, as the primary regulators of the immune system, play an important role in the pathogenesis of a variety of human liver disorders (Heneghan et al., 2002), including autoimmune liver disease, viral hepatitis (Rosen et al., 2002), and alcoholic liver disease (Chedid et al., 1993). Injection of the T cell mitogenic plant lectin concanavalin A (ConA) is a well-established model to study T cell-mediated hepatitis (Tiegs et al., 1992).

Unfortunately, there are few effective treatments for hepatitis. For example, treatment of autoimmune chronic hepatitis is generally limited to immunosuppressive treatment with corticosteroids. While corticosteroid therapy has been shown to extend life, improve biochemical abnormalities and enhance quality of life in many patients, the beneficial effects of corticosteroids are compensated by the often serious complications and side effects associated with the prolonged treatment therewith. For the treatment of hepatitis B and C, the FDA has approved administration of recombinant interferon alpha. However, for adult patients with hepatitis B infections only about 35% responded to such treatment, and in perinatal infectees only about 10% responded to treatment. For hepatitis C infections, despite apparent short-term success utilizing such therapy, the rate of relapse after termination of treatment is high. In addition, a further difficulty with alpha interferon therapy is that the composition frequently has toxic side effects such as thrombocytopenia, leukopenia, bacterial infections, and influenza-like symptoms, which require reduced dosages for sensitive patients. Other agents used to treat chronic hepatitis B or C include the nucleoside analog ribovirin and ursodeoxycholic acid; however, neither has been shown to be very effective. Consequently, the need remains for finding new and effective drugs and methods for treating hepatitis.

None of the background art demonstrates that HSP60 or a fragment thereof may be an effective agent particularly useful for preventing or treating hepatitis.

There exists a long-felt need for an effective means of curing or ameliorating T cell mediated pathologies, including hepatic disorders. Such a treatment should ideally control the inappropriate T cell response, rather than merely reducing the symptoms. The development of new agents capable of selectively inhibiting the deleterious T cell mediated response with minimal side effects is therefore desirable.

SUMMARY OF THE INVENTION

The present invention provides compositions and methods utilizing heat shock protein 60 (HSP60) and peptides derived from HSP60 including the known peptide designated p277 (positions 437-460 of human HSP60), nucleic acids encoding same, and analogs, derivatives and salts thereof, for the treatment and prevention of T cell mediated pathologies.

The application is based, in part, on the unexpected finding that p277 and analogs thereof may be used for inhibiting T-cell mediated inflammation, regardless of the specific antigen to which these T cells are directed. p277 and analogs thereof were surprisingly found to inhibit T cell mediated inflammation via induction of an anti-inflammatory response characterized by at least one of p277-specific anti-ergotypic response, stimulation of $CD4^+CD25^+$ regulatory T cells, and SOCS3-mediated inhibition of chemotaxis.

Thus, the invention provides novel uses for p277 and its analogs and derivatives and nucleic acid sequences encoding them in treating T cell mediated pathologies, beyond the known uses for IDDM and graft rejection. Therapeutic and prophylactic T-cell vaccination compositions and methods thereof are further disclosed.

According to one embodiment, the invention specifically demonstrates, for the first time, that HSP60, as well as a p277 analog designated p277($Val^6Val^{11}$) (also known as DiaPep277), is an effective agent for treating or preventing T cell-mediated hepatitis. Thus, the invention provides novel therapeutic methods utilizing HSP60 and p277, fragments, analogs, homologs and derivatives thereof, and nucleic acids encoding same, for the treatment and prevention of hepatic disorders by suppression of inflammation.

Peptide p277($Val^6Val^{11}$), also known as DiaPep277, disclosed in U.S. Pat. No. 6,180,103, is a synthetic analog of a native 24-amino acid fragment p277 of the 60 kDa human HSP60. The terms p277 and Peptide p277 are used interchangeably throughout the specification and in the claims and these terms are intended to denote both the native sequence (SEQ ID NO:1) as well as synthetic variants thereof, such as DiaPep277 (SEQ ID NO:2).

In various embodiments of the present invention, there are provided T cell vaccine compositions and methods utilizing HSP60, active fragments thereof, p277, and analogs, variants, derivatives and salts thereof for the treatment of T cell mediated pathologies.

In one aspect, the invention provides a pharmaceutical composition comprising attenuated activated T cells exposed ex vivo to a compound selected from the group consisting of: p277 (SEQ ID NO:1), analogs, variants, derivatives and salts thereof.

In certain embodiments, the compound is a p277 analog wherein at least one of the cysteine residues in positions 6 and 11 of p277 has been substituted. In another embodiment, the p277 analog is p277($Val^6Val^{11}$) (SEQ ID NO:2). In another embodiment, the p277 analog is p277($Ser^6Ser^{11}$) (SEQ ID NO:3).

In another aspect, the invention provides a pharmaceutical composition comprising a first population of T cells cultured ex vivo in the presence of a second population of T cells, the second population of T cells being histocompatible attenuated activated T cells exposed ex vivo to a compound selected from a group consisting of: p277 (SEQ ID NO:1), analogs, variants, derivatives and salts thereof.

In certain embodiments, the compound is a p277 analog wherein at least one of the cysteine residues in positions 6 and 11 of p277 has been substituted. In another embodiment, the p277 analog is p277($Val^6Val^{11}$) (SEQ ID NO:2). In another embodiment, the p277 analog is p277($Ser^6Ser^{11}$) (SEQ ID NO:3).

In another aspect, the invention provides methods of treating or preventing a T cell mediated pathology in a subject in need thereof, comprising: (a) isolating T cells from the subject or from a donor histocompatible with said subject; (b) activating the T cells ex vivo to induce Major Histocompatibility Complex (MHC) II expression; (c) exposing said activated cells to a compound selected from a group consisting of: p277 (SEQ ID NO:1), analogs, variants, derivatives and salts thereof; (d) attenuating said T cells; and (e) introducing said T cells into the subject in an amount sufficient to induce an anti-ergotypic response in said subject.

In another embodiment, the attenuation step is performed after activating the cells and prior to exposing them to said compound. In another embodiment, the p277 analog is p277($Val^6Val^{11}$) (SEQ ID NO:2). In another embodiment, the p277 analog is p277($Ser^6Ser^{11}$) (SEQ ID NO:3). In various embodiments, the T cell mediated pathology is selected from the group consisting of: inflammatory diseases, autoimmune diseases, allergic diseases and Th1 mediated diseases.

In another aspect, the invention provides methods of treating or preventing a T cell mediated pathology in a subject in need thereof, comprising: (a) isolating a first population of T cells from the subject or from a donor histocompatible with said subject; (b) culturing the first population of T cells in the presence of a second population of histocompatible attenuated activated T cells and a compound selected from a group consisting of: p277 (SEQ ID NO:1), analogs, variants, derivatives and salts thereof; and (c) introducing said first population of T cells into the subject in an amount sufficient to induce an anti-ergotypic response in said subject.

Advantageously, culturing includes repeated exposure of the first population of T cells to fresh attenuated activated T cells and said compound under conditions suitable for proliferation of said first population of T cells.

In another embodiment, step (b) may alternatively comprise culturing the first population of T cells in the presence of a second population of histocompatible attenuated activated T cells that were previously exposed to a compound selected from a group consisting of: p277 (SEQ ID NO:1), analogs, variants, derivatives and salts thereof. In another embodiment, the p277 analog is p277($Val^6Val^{11}$) (SEQ ID NO:2). In another embodiment, the p277 analog is p277($Ser^6Ser^{11}$) (SEQ ID NO:3). In various embodiments, the T cell mediated pathology is selected from the group consisting of: inflammatory diseases, autoimmune diseases, allergic diseases and Th1 mediated diseases.

In another aspect, the invention provides methods of treating hepatitis or liver damage associated therewith in a subject in need thereof, comprising: (a) isolating T cells from the subject or from a donor histocompatible with said subject; (b) activating the T cells ex vivo to induce Major Histocompatibility Complex (MHC) II expression; (c) exposing said activated cells to a compound selected from a group consisting of: HSP60, an active fragment thereof, p277 (SEQ ID NO:1), analogs, variants, derivatives and salts thereof; (d) attenuating said T cells; and (e) introducing said T cells into the subject in an amount sufficient to induce an anti-ergotypic response in said subject.

In another embodiment, the attenuation step is performed after activating the cells and prior to exposing them to said compound.

In another aspect, the invention provides methods of treating hepatitis or liver damage associated therewith in a subject in need thereof, comprising: (a) isolating a first population of T cells from the subject or from a donor histocompatible with said subject; (b) culturing the first population of T cells in the presence of a second population of histocompatible attenuated activated T cells and a compound selected from a group consisting of: HSP60, an active fragment thereof, p277 (SEQ ID NO:1), analogs, variants, derivatives and salts thereof; and (C) introducing said first population of T cells into the subject in an amount sufficient to induce an anti-ergotypic response in said subject.

In another embodiment, step (b) may alternatively comprise culturing the first population of T cells in the presence of a second population of histocompatible attenuated activated T cells that were previously exposed to a compound selected from a group consisting of: p277 (SEQ ID NO:1), analogs, variants, derivatives and salts thereof.

In another aspect, the invention provides methods of treating or preventing a T cell mediated pathology other than insulin-dependent diabetes mellitus and graft rejection in a subject in need thereof, comprising administering to the subject a therapeutically-effective amount of a compound selected from a group consisting of: p277 (SEQ ID NO:1), analogs, variants, derivatives and salts thereof.

In one embodiment, the compound is a p277 analog in which at least one of the cysteine residues in positions 6 and 11 of p277 has been substituted. In another embodiment, the p277 analog is p277(Val$^6$Val$^{11}$) (SEQ ID NO:2). In another embodiment, the p277 analog is p277(Ser$^6$Ser$^{11}$) (SEQ ID NO:3).

In another embodiment, the compound is administered in the form of a pharmaceutical composition further comprising a pharmaceutically acceptable carrier, and optionally an adjuvant. In another embodiment, the composition is administered in a manner selected from: enteral (e.g. oral, rectal), buccal, transmucosal, intranasal, bronchial and intrapulmonary administration. In another embodiment, the composition comprises a sustained release formulation of said compound.

In other embodiments, the T cell mediated pathology is selected from the group consisting of: inflammatory diseases, autoimmune diseases, allergic diseases and Th1 mediated diseases.

Another aspect of the present invention is a method of treating hepatitis comprising administering to a subject in need thereof a therapeutically effective amount of a compound selected from a group consisting of: HSP60 protein, an active fragment thereof, and analogs, variants, derivatives and salts thereof.

In one preferred embodiment, the HSP60 protein is human HSP60. In another embodiment, the HSP60 protein has an amino acid sequence as set forth in any one of SEQ ID NOS:4 and 11. In another embodiment, other mammalian HSP60 are used. In yet another embodiment, the HSP60 polypeptide is bacterial HSP60. In another embodiment, the HSP60 polypeptide is E. coli GroEL (Zanin-Zhorov et al., 2003; SEQ ID NO:9). In another preferred embodiment, the active fragment of HSP60 is the p277 peptide (SEQ ID NO:1). In another embodiment, the HSP60 fragment analog has an amino acid sequence as set forth in SEQ ID NO:2. In yet another embodiment, the HSP60 fragment analog has an amino acid sequence as set forth in SEQ ID NO:3. In another embodiment, the compound is administered in the form of a pharmaceutical composition further comprising a pharmaceutically acceptable carrier or diluent. In another embodiment, the composition comprises a sustained release formulation of said compound.

In another aspect, there is provided a method of treating or preventing liver damage comprising administering to a subject in need thereof a therapeutically effective amount of a compound selected from a group consisting of: HSP60 protein, an active fragment thereof, and analogs, variants, derivatives and salts thereof.

In one embodiment, the HSP60 protein is selected from the group consisting of: human HSP60, mammalian HSP60 and bacterial HSP60. In a preferred embodiment, the HSP60 protein is human HSP60. In another embodiment, the HSP60 protein has an amino acid sequence as set forth in any one of SEQ ID NOS:4 and 11. In another embodiment, the HSP60 protein has an amino acid sequence as set forth in SEQ ID NO:9. In another particular embodiment, the HSP60 fragment is the p277 peptide, having an amino acid sequence as set forth in SEQ ID NO:1. In another embodiment, the HSP60 fragment analog has an amino acid sequence as set forth in SEQ ID NO:2. In yet another embodiment, the HSP60 fragment analog has an amino acid sequence as set forth in SEQ ID NO:3. In another embodiment, the compound is administered in the form of a pharmaceutical composition further comprising a pharmaceutically acceptable carrier or diluent. In another embodiment, the composition comprises a sustained release formulation of said compound. According to various embodiments, the subject in need thereof is afflicted with a disease selected from: (i) viral hepatitis (ii) parasitic hepatitis (iii) autoimmune hepatitis (iv) primary biliary cirrhosis (v) alcoholic liver disease.

In another aspect, the present invention provides methods of treating or preventing a T cell mediated pathology other than insulin-dependent diabetes mellitus and graft rejection in a subject in need thereof, comprising administering to the subject a therapeutically-effective amount of a pharmaceutical composition comprising a recombinant construct, the recombinant construct comprising a nucleic acid sequence encoding a peptide selected from: p277 (SEQ ID NO:1), analogs and variants thereof, the nucleic acid sequence being operably linked to one or more transcription control sequences; and a pharmaceutically acceptable carrier.

In one embodiment, the encoded peptide is a p277 analog in which at least one of the cysteine residues in positions 6 and 11 of p277 has been substituted. In another embodiment, the encoded p277 analog is p277(Val$^6$Val$^{11}$) (SEQ ID NO:2). In another embodiment, the encoded p277 analog is p277 (Ser$^6$Ser$^{11}$) (SEQ ID NO:3). In another embodiment, said construct comprises a nucleic acid sequence as set forth in any one of SEQ ID NOS:5-7. In another embodiment, the nucleic acid composition is administered as naked DNA. In other embodiments, the T cell mediated pathology is selected from the group consisting of: inflammatory diseases, autoimmune diseases, allergic diseases and Th1 mediated diseases.

In another aspect, the invention provides a method of treating hepatitis, comprising administering to a subject in need thereof a therapeutically effective amount of a pharmaceutical composition comprising as an active ingredient a recombinant construct, the recombinant construct comprising a nucleic acid sequence encoding a polypeptide selected from a group consisting of: HSP60 protein, an active fragment thereof, and analogs and variants thereof, wherein the nucleic acid sequence is operably linked to one or more transcription control sequences, thereby treating hepatitis.

In one embodiment, the HSP60 protein is selected from the group consisting of: human HSP60, mammalian HSP60 and bacterial HSP60. In a preferred embodiment, the HSP60 protein is human HSP60. In another embodiment, the HSP60 protein has an amino acid sequence as set forth in any one of SEQ ID NOS:4 and 11. In another embodiment, the HSP60 protein has an amino acid sequence as set forth in SEQ ID NO:9. In another particular embodiment, the HSP60 fragment is the p277 peptide, having an amino acid sequence as set forth in SEQ ID NO:1. In another embodiment, the HSP60 fragment analog has an amino acid sequence as set forth in SEQ ID NO:2. In yet another embodiment, the HSP60 fragment analog has an amino acid sequence as set forth in SEQ ID NO:3. In another embodiment, said construct comprises a nucleic acid sequence as set forth in any one of SEQ ID NOS:5-8.

The invention provides, in another aspect, a method of treating or preventing liver damage, comprising administering to a subject in need thereof a therapeutically effective amount of a pharmaceutical composition comprising as an active ingredient a recombinant construct, the recombinant construct comprising an isolated nucleic acid sequence encoding a polypeptide selected from a group consisting of: HSP60 protein, an active fragment thereof, and analogs and variants thereof, wherein the nucleic acid sequence is operably linked to one or more transcription control sequences, thereby treating or preventing liver damage.

In one embodiment, the HSP60 protein is selected from the group consisting of: human HSP60, mammalian HSP60 and bacterial HSP60. In a preferred embodiment, the HSP60 protein is human HSP60. In another embodiment, the HSP60 protein has an amino acid sequence as set forth in any one of SEQ ID NOS:4 and 11. In another embodiment, the HSP60 protein has an amino acid sequence as set forth in SEQ ID NO:9. In another particular embodiment, the HSP60 fragment is the p277 peptide, having an amino acid sequence as set forth in SEQ ID NO:1. In another embodiment, the HSP60 fragment analog has an amino acid sequence as set forth in SEQ ID NO:2. In yet another embodiment, the HSP60 fragment analog has an amino acid sequence as set forth in SEQ ID NO:3. In another embodiment, said construct comprises a nucleic acid sequence as set forth in any one of SEQ ID NOS:5-8. In another embodiment, the subject in need thereof is afflicted with a disease selected from: (i) viral hepatitis (ii) parasitic hepatitis (iii) autoimmune hepatitis (iv) primary biliary cirrhosis (v) alcoholic liver disease.

In another aspect, there is provided a method of treating hepatitis or liver damage associated therewith comprising the steps of (a) obtaining cells from a subject; (b) introducing a recombinant construct into the cells ex vivo, the construct comprising an isolated nucleic acid sequence encoding a polypeptide selected from a group consisting of: HSP60 protein, an active fragment thereof, and analogs and variants thereof, wherein the nucleic acid sequence is operably linked to one or more transcription control sequences; and (c) reintroducing said treated cells to the subject; wherein the HSP60 or fragment, analog or variant thereof is expressed in vivo in said treated cells in an amount sufficient to treat hepatitis or liver damage associated therewith.

In one embodiment, the HSP60 protein is selected from the group consisting of: human HSP60, mammalian HSP60 and bacterial HSP60. In a preferred embodiment, the HSP60 protein is human HSP60. In another embodiment, the HSP60 protein has an amino acid sequence as set forth in any one of SEQ ID NOS:4 and 11. In another embodiment, the HSP60 protein has an amino acid sequence as set forth in SEQ ID NO:9. In another particular embodiment, the HSP60 fragment is the p277 peptide, having an amino acid sequence as set forth in SEQ ID NO:1. In another embodiment, the HSP60 fragment analog has an amino acid sequence as set forth in SEQ ID NO:2. In yet another embodiment, the HSP60 fragment analog has an amino acid sequence as set forth in SEQ ID NO:3. In another embodiment, said construct comprises a nucleic acid sequence as set forth in any one of SEQ ID NOS:5-8. In another embodiment, the subject in need thereof is afflicted with a disease selected from: (i) viral hepatitis (ii) parasitic hepatitis (iii) autoimmune hepatitis (iv) primary biliary cirrhosis (v) alcoholic liver disease.

These and other embodiments of the present invention will become apparent in conjunction with the FIGS., description and claims that follow.

DETAILED DESCRIPTION OF THE INVENTION

Figure 1A:
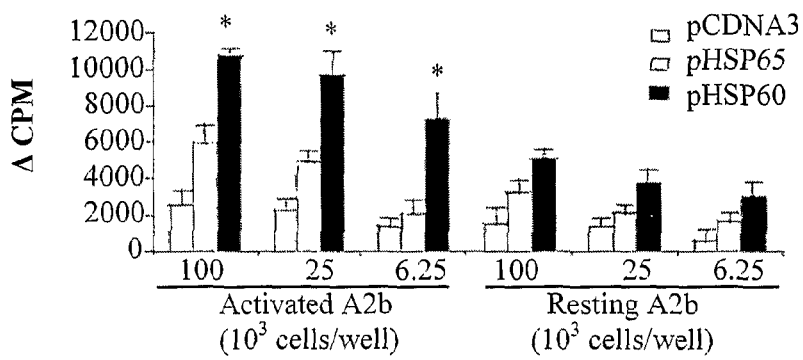
FIG. 1. DNA vaccination with HSP60 induces anti-ergotypic T cells. A and B. Anti-ergotypic proliferative response of LNC from rats vaccinated with pcDNA3, pHSP65 or pHSP60 (A) or pcDNA3, pI or pII (B), taken 26 days after the induction of AA. Proliferative responses are presented as the ΔCPM±SEM of quadruplicate cultures. * $p<0.05$ compared to the pHSP65 (A) or the pcDNA3 (B) groups. C. Monoclonal antibodies to MHC-II/RT1.B, MHC-II/RT1.D or MHC-I were assayed for their ability to block the anti-ergotypic proliferative response. Results are presented as the percent of inhibition of proliferation±SEM of quadriplicate cultures. D. Anti-ergotypic cytokine response of LNC taken from rats vaccinated with pcDNA3, pHSP65, pHSP60, pI or pII 26 days after the induction of AA. IFNγ, TGFβ1, IL-10 and IL-4 were quantified in the culture supernatants after 72 hr of stimulation with $10^5$ activated or resting, irradiated, A2b cells per well. The results are presented as pg/ml±SEM of triplicate cultures. Three independent experiments produced similar results.

The invention provides novel compositions and methods utilizing HSP60 and peptides thereof, including the p277 peptide (SEQ ID NOT, positions 437-460 of human HSP60) and analogs thereof for the treatment of T cell mediated disorders.

It is herein demonstrated for the first time that p277 may be used for inhibiting T-cell mediated inflammation, regardless of the specific antigen to which these T cells are directed. Thus, the invention provides novel uses for p277 and its analogs and derivatives in treating T cell mediated pathologies beyond the reported uses for IDDM and graft rejection.

The invention is based, in part, on the surprising discovery that HSP60 and p277 are presented by activated T cells to regulatory (anti-ergotypic) T cells. It is now disclosed for the first time that HSP60 and p277-specific T cell lines demonstrating anti-ergotypic activity inhibit IFNγ production by activated T-cells and ameliorate adjuvant arthritis (AA) when adoptively transferred to rats.

The invention is further based, in part, on the unexpected discovery that HSP60 and p277 act as co-stimulators of human CD4$^+$CD25$^+$ T regulatory cells (Tregs), added before mitogenic anti-CD3 activation. Treatment of Tregs with HSP60 or p277 suppressed IFN-γ and TNF-α secretion, and proliferation of CD4$^+$CD25$^-$ or CD8$^+$ T cells in a TLR-2-dependent manner.

The present invention is also based, in part, on the unexpected discovery that HSP60 and p277 up-regulate suppressors of cytokine signaling (SOCS)$_3$ expression, thereby inhibiting the down-stream effects of stromal cell-derived (SDF)-1α (CXCL12)-CXCR4 interactions in vitro and in vivo.

In one aspect, the present invention provides methods for treating or preventing a T cell mediated pathology. The term "T-cell mediated pathology" as used herein indicates any condition in which an inappropriate T cell response is a component of the pathology. The term is intended to include both diseases directly mediated by T cells, and also diseases in which an inappropriate T cell response contributes to the production of abnormal antibodies.

According to various embodiments, the T cell mediated pathology includes, but is not limited to, autoimmune diseases, allergic diseases, Th1 mediated diseases and other inflammatory diseases. In one embodiment of the invention, the compositions and methods of the invention are useful for treating a T cell-mediated autoimmune disease, including but not limited to: multiple sclerosis, rheumatoid arthritis, autoimmune neuritis, systemic lupus erythematosus (SLE), psoriasis, Sjogren's disease, thyroid disease, myasthenia gravis, sarcoidosis, autoimmune uveitis, and inflammatory bowel disease (Crohn's and ulcerative colitis). In other particular embodiments the compositions and methods of the invention are useful for treating a Th1-associated inflammatory disease, e.g. Th1 mediated allergic responses which result in skin sensitivity and inflammation, such as contact dermatitis. In other embodiments, the compositions and methods of the invention are useful in treating a wide range of inflammatory diseases and conditions. According to certain other particular embodiments, the compositions and methods of the invention are useful in treating inflammatory conditions in which chemotaxis of T cells in response to a chemoattractant (particularly SDF-1α) results in migration of the cells to a site of inflammation, e.g. glomerulonephritis, post-viral myocarditis and atherosclerosis. It should be emphasized, however, that the present invention is not intended to include known therapeutic uses of p277, such as for inhibiting IDDM and graft rejection.

The present invention is also based, in part, on the unexpected discovery that HSP60, as well as a peptide thereof, i.e. p277, is an effective agent for treating or preventing the symptoms of T cell-mediated hepatitis. It is now disclosed for the first time that HSP60 and p277 inhibit the clinical, histological, and serological manifestations of concanavalin A (ConA)-induced hepatitis, an animal disease model of acute inflammatory hepatitis. Without wishing to be bound by any theory or mechanism of action, this phenomenon may be associated with a Toll-like receptor 2 (TLR2)-dependent modulation of the expression of Th1/Th2 transcription factors. HSP60 is herein demonstrated to differentially modulate the expression of Th1/Th2 transcription factors: down-regulating T-bet, NF-κB, and NFATp, and up-regulating GATA-3, leading to decreased secretion of TNFα and IFNγ and enhanced secretion of IL-10. HSP60 and p277 also modulate the secretion of IL-6, a well-known regulator of T cell mediated hepatitis.

The term "hepatitis" is used herein to refer to a disease of patients characterized in part by inflammation of the liver. Causative agents of hepatitis include, for example, viral infections, such as infections of hepatitis A, B, C, D, E, and G viruses; parasitic infections, including, but not limited to infections of *Schistosoma mansoni*, *Schistosoma hematobium*, and *Schistosoma japonicum*; autoimmune diseases, including, but not limited to, autoimmune hepatitis and primary biliary cirrhosis; and non-infectious hepatotoxic agents, including, but not limited to, alcohol, drugs and toxins. Liver damage due to inflammation is associated with these hepatic disorders. The compositions and methods of the invention are thus useful for treating or preventing liver damage associated, for example, with inflammation secondary to viral or parasitic infection.

Protein- and Peptide-Based Compositions and Methods

According to one aspect, the present invention is directed to the use of pharmaceutical compositions comprising as an active ingredient a compound selected from a group consisting of: p277 (VLGGGCALLRCIPALDSLTPANED, SEQ ID NO:1), analogs, variants, derivatives and salts thereof, for the treatment and prevention of T cell mediated pathologies. In one embodiment, the compositions further comprise pharmaceutically acceptable carriers, excipients or diluents.

In one embodiment, the active ingredient is a p277 analog, in which at least one of the cysteine residues in positions 6 and 11 of p277 has been substituted. In one preferred embodiment, the p277 analog is p277(Val$^6$Val$^{11}$) (VLGGGVALLRVIPALDSLTPANED, SEQ ID NO:2).

In another preferred embodiment, the active ingredient is p277(Ser$^6$Ser$^{11}$) (VLGGGSALLRSIPALDSLTPANED SEQ ID NO:3). Surprisingly, it is now disclosed that certain p277 analogs that may be inactive as specific antigens modulating IDDM, may be used to regulate T cell function according to the present invention (see Example 36). Thus, for example, p277(Ser$^6$Ser$^{11}$) that did not reduce the incidence of diabetes upon immunization by a single subcutaneous injection in mineral oil (see U.S. Pat. No. 6,180,103), may be useful for modulating T cell immunity (e.g. in hepatitis) upon prolonged administration without an adjuvant, e.g. as a sustained-release formulation.

Another aspect of the present invention relates to the use of a compound selected from a group consisting of: p277 (SEQ ID NO:1), analogs, variants, derivatives and salts thereof, for the preparation of a pharmaceutical compositions for the treatment and prevention of T cell mediated pathologies or symptoms associated therewith.

In another aspect, there is provided a method for treating a T cell mediated pathology other than insulin-dependent diabetes mellitus and graft rejection in a subject in need thereof, comprising administering to the subject a therapeutically-effective amount of a compound selected from a group consisting of: p277 (SEQ ID NO:1), analogs, variants, derivatives and salts thereof. In one embodiment, the subject is human.

In another aspect, there is provided a method for preventing a T cell mediated pathology other than insulin-dependent diabetes mellitus and graft rejection in a subject in need thereof, comprising administering to the subject a therapeutically-effective amount of a compound selected from a group consisting of: p277 (SEQ ID NO:1), analogs, variants, derivatives and salts thereof.

In another aspect, the invention is directed to a composition comprising heat shock protein 60 (HSP60), or an active fragment thereof, for treating or preventing the symptoms of hepatitis. In one preferred embodiment, the HSP60 polypeptide is human HSP60. In one embodiment, the human HSP60 has an amino acid sequence as set forth in SEQ ID NO:4 (corresponding to accession number: P10809). In another embodiment, the human HSP60 has an amino acid sequence as set forth in SEQ ID NO:11 (corresponding to accession number: gi:306890). In another embodiment, other mammalian HSP60 are used. In yet another embodiment, the HSP60 polypeptide is bacterial HSP60. In another embodiment, the HSP60 polypeptide is *E. coli* GroEL (which have been previously implicated in TLR-2 mediated T cell adhesion, see Zanin-Zhorov et al., 2003). In one embodiment, the *E. coli* GroEL has an amino acid sequence as set forth in SEQ ID NO:9 (accession number: AAS75782). In another preferred embodiment, the active fragment of HSP60 is the p277 peptide (SEQ ID NO:1). According to other embodiments, the composition may comprise homologs, analogs, derivatives and salts thereof. In one preferred embodiment, the analog has an amino acid sequence as set forth in SEQ ID NO:2. In another preferred embodiment, the analog has an amino acid sequence as set forth in SEQ ID NO:3.

Another aspect of the present invention relates to the use of a compound selected from a group consisting of: HSP60 protein, an active fragment thereof, and analogs, variants, derivatives and salts thereof, for the preparation of a pharmaceutical compositions for the treatment and prevention of the symptoms of hepatitis.

Another aspect of the present invention is a method of treating hepatitis comprising administering to a subject in need thereof a therapeutically effective amount of a compound selected from a group consisting of: HSP60 protein, an active fragment thereof, and analogs, variants, derivatives and salts thereof.

In another aspect, there is provided a method of treating or preventing liver damage comprising administering to a subject in need thereof a therapeutically effective amount of a compound selected from a group consisting of: HSP60 protein, an active fragment thereof, and analogs, variants, derivatives and salts thereof.

The polypeptides or peptides of the invention may be synthesized using any recombinant or synthetic method known in the air, including, but not limited to, solid phase and solution phase synthesis methods. A non-limitative example of peptide synthesis is presented in the Examples; however, other methods known in the art may be used. For solid phase peptide synthesis, a summary of the many techniques may be found in: Stewart and Young, 1963; and Meienhofer, 1973. For a review of classical solution synthesis, see Schroder and Lupke, 1965.

The amino acid residues described herein are preferred to be in the "L" isomeric form. However, residues in the "D" isomeric form can be substituted for any L-amino acid residue, as long as the peptide retains the desired functional property.

It should be understood that a polypeptide or a peptide of the invention need not be identical to the amino acid sequence of SEQ ID NOS:1, 2 or 3, so long as it retains their biological activity with respect to T cell mediated pathologies, as described herein. Several non-limitative examples of methods suitable for determining p277 activity are described in the Examples below. Similarly, a polypeptide or a peptide of the invention need not be identical to the amino acid sequence of SEQ ID NOS:4, 9 or 11, so long as it retains their biological activity with respect to hepatitis, as described herein.

As used herein, the terms "peptide", "polypeptide" and "protein" all refer to a primary sequence of amino acids that are joined by covalent "peptide linkages". In general, a peptide consists of a few amino acids, typically from 2-50 amino acids, and is shorter than a protein. The term "polypeptide" encompasses peptides and proteins. In some embodiments, the peptide, polypeptide or protein is synthetic, while in other embodiments, the peptide, polypeptide or protein is recombinant or naturally occurring. A synthetic peptide is a peptide which is produced by artificial means in vitro (i.e., was not produced in vivo). The HSP60 fragments and peptides according to the present invention are preferably 7-30 amino acids in length.

Whenever the terms "p277", "peptide p277", "fragment of HSP60" or "peptide of HSP60" are mentioned in the invention, also salts and functional derivatives thereof are contemplated, as long as the biological activity of the peptide with respect to T cell mediated pathologies and/or hepatitis is maintained. The present invention encompasses any analog, derivative, and conjugate containing a polypeptide or a peptide of the invention, so long as the polypeptide or peptide is capable of inhibiting or preventing hepatitis and/or other T cell mediated pathologies. Thus, the present invention encompasses peptides containing non-natural amino acid derivatives or non-protein side chains.

The term "analog" indicates molecule which has the amino acid sequence according to the invention except for one or more amino acid changes or one or more modification/replacement of an amide bond. In one embodiment, the term relates to peptides in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. In other embodiments, the term further includes non-conservative substitutions in an amino acid that does not contribute to the biological activity of the peptide. For example, without limitation, at least one of the cysteine residues in positions 6 and 11 of p277 may be substituted.

The phrase "conservative substitution" also includes the use of a chemically derivatized residue in place of a non-derivatized residue provided that such polypeptide or peptide displays the requisite inhibitory function on hepatic disorders and/or other T cell mediated pathologies as specified herein.

The term "derivative" includes any chemical derivative of the polypeptides or peptides of the invention having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxy-carbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptide of the invention by chemical modifications including, but not limited to, amino terminal acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

Peptides of the present invention also include any peptide having one or more additions and/or deletions of residues relative to the sequence of p277, so long as they are able to inhibit T cell mediated pathologies. Polypeptides or peptides of the present invention also include any polypeptide or peptide having one or more additions and/or deletions of residues relative to the sequence of the HSP60 or p277, so long as they are able to inhibit hepatitis and/or liver damage.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

A polypeptide or peptide of the present invention may be coupled to or conjugated with another protein or polypeptide to produce a conjugate. Such a conjugate may have advantages over the polypeptide or peptide used alone.

A pharmaceutical composition useful in the practice of the present invention typically contains a polypeptide or a peptide of the invention formulated into the pharmaceutical composition as a neutralized pharmaceutically acceptable salt form. Pharmaceutically acceptable salts include the acid addition salts (formed with the free amino groups of the polypeptide), which are formed with inorganic acids, such as for example, hydrochloric or phosphoric acid, or with organic acids such as acetic, oxalic, tartaric, and the like.

Suitable bases capable of forming salts with the polypeptides or peptides of the present invention include, but are not limited to, inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

The preparation of pharmaceutical compositions, which contain peptides or polypeptides as active ingredients is well known in the art. Typically, such compositions are prepared as indictable, either as liquid solutions or suspensions, however, solid forms, which can be suspended or solubilized prior to injection, can also be prepared. The preparation can also be emulsified. The active therapeutic ingredient is mixed with inorganic and/or organic carriers, which are pharmaceutically acceptable and compatible with the active ingredient. Carriers are pharmaceutically acceptable excipients (vehicles) comprising more or less inert substances when added to a pharmaceutical composition to confer suitable consistency or form to the composition. Suitable carriers are, for example, water, saline, dextrose, glycerol, ethanol, or the like and combinations thereof. In addition, if desired, the composition can contain minor amounts of auxiliary substances such as wetting or emulsifying agents and pH buffering agents, which enhance the effectiveness of the active ingredient.

In one particular embodiment, the composition is a vaccine composition comprising an immunogenic adjuvant suitable for enhancing a p277-specific anti-ergotypic reaction in said subject.

The term "anti-ergotypic T cell response" refers to the activation of regulatory anti-ergotypic T cells. In various embodiments, the anti-ergotypic T cell response may be measured as increased T cell proliferation response to activated syngeneic T cells. Alternatively, the activation of regulatory anti-ergotypic T cells may be determined by measuring the secretion level of cytokines by said T cells.

The vaccine composition may optionally comprise adjuvants such as vegetable oils or emulsions thereof, surface active substances, e.g., hexadecylamin, octadecyl amino acid esters, octadecylamine, lysolecithin, dimethyl-dioctadecy-lammonium bromide, N,N-dicoctadecyl-N'-N'bis(2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions (including, but not limited to, oil-in-water emulsions having oil droplets in the submicron range, such as those disclosed by U.S. Pat. Nos. 5,961,970, 4,073,943 and 4,168,308), liposaccharides such as MPL® and mineral gels. The peptide antigens of the present invention can be coupled to albumin or to other carrier molecule in order to modulate or enhance the immune response, all as are well known to those of ordinary skill in the vaccine art. Metabolizable lipid emulsions, such as Intralipid or Lipofundin, may also be used as vehicles for the p277 vaccination in the mamier disclosed in WO 97/02016, the entire contents of which being hereby incorporated herein by reference. These lipid emulsions may be formulated as oil-in-water submicron emulsion, as disclosed in U.S. Pat. No. 5,961,970.

The vaccines can be administered to a human or animal by a variety of routes, including but not limited to parenteral, intradermal, transdermal (such as by the use of slow release polymers), intramuscular, intraperitoneal, intravenous, subcutaneous, oral and intranasal routes of administration, according to protocols well known in the art. The vaccine compositions of the invention are administered in a dose which is suitable to elicit an immune response in said subject. The particular dosage of the p277 peptide will depend upon the age, weight and medical condition of the subject to be treated, as well as on the identity of the antigen and the method of administration. Suitable doses will be readily determined by the skilled artisan. A preferred dose for human intramuscular, subcutaneous and oral vaccination is between about 12.5 µg to about 20 mg per kg body weight, preferably between about 25 µg to about 10 mg per kg body weight, and more preferably between about 125 µg to about 2 mg per kg body weight. Adjustment and manipulation of established dosage ranges used with traditional carrier antigens for adaptation to the present vaccine is well within the ability of those skilled in the art.

In other particular embodiments, the compound is formulated for oral, buccal, rectal, transmucosal, transnasal, enteral, bronchial, or intrapulmonary administration. In these embodiments, the compound is formulated without an adjuvant. The preparation of such formulations is well within the ability of one skilled in the art.

Sustained-release oral delivery systems are also contemplated and are preferred method of mucosal administration. Non-limiting examples of sustained-release oral dosage forms include those described in: U.S. Pat. Nos. 4,704,295; 4,556,552; 4,309,404; 4,309,406; 5,405,619; 5,371,109; 5,356,635 and 5,151,272. In one preferable embodiment, the p277, analogs derivatives and salts thereof of the invention are derivatized by reversible pegylation as described for example by WO/2004/089280, hereby fully incorporated herein by reference. In this embodiment, the active ingredient is a peptide-PEG conjugate having an increased half-life in the circulation, from which PEG can be released by hydrolysis under physiological conditions.

Sustained-release oral dosage forms coated with bioadhesives may also be used. Examples of such compositions are disclosed by: WO 85/02092, EP 516141 and EP 205282; U.S. Pat. Nos. 4,226,848; 4,713,243; and 4,940,587; WO 85/02092

Commercially available sustained-release oral delivery formulations and devices include those marketed by ALZA Corporation, Palo Alto, Calif., USA, under the trade names OROS®, ALZET®, INFUSET™, IVOS™, and OSMET®, and those described by: U.S. Pat. Nos. 5,284,660; 5,141,750; 5,110,597; 4,917,895; 4,837,027; 3,993,073; 3,948,262; 3,944,064; and 3,699,963; PCT/US93/10077 and PCT/US93/11660; and EP 259013 and EP 354742.

For by-inhalation administration (i.e., delivery to the bronchopulmonary mucosa), suitable sprays and aerosols can be used, for example, with a nebulizer, such as those described in U.S. Pat. Nos. 4,624,251; 3,703,173; 3,561,444; and 4,635,627. The aerosol material is inhaled by the subject to be treated.

Other systems of aerosol delivery, such as the pressurized metered-dose inhaler (MDI) and the dry powder inhaler, as disclosed by Newman, S. P. (1984) (Aerosols and the Lung, Clarke, S. W. Davis, D., eds., pp. 197-224, Butterworths, London, England) can be used when practicing the present invention.

Aerosol delivery systems of the type disclosed herein are available from numerous commercial sources, including Fisons Corporation (Bedford, Mass.), Schering Corp. (Kenilworth, N.J.), and American Pharmoseal Co. (Valencia, Calif.).

Formulations for nasal administration can be administered, for example, as a dry powder or in an aqueous solution. Preferred aerosol-based pharmaceutical formulations may comprise, for example, a physiologically acceptable buffered saline solution containing p277, analogs derivatives and salts thereof of the present invention.

The nasally administered formulation of the present invention may comprise a thermosetting gel, which increases in viscosity at body temperature upon contact with the nasal mucosa.

Formulations for buccal administration may comprise a mucoadhesive mixed with effective amounts of p277, analogs derivatives and salts thereof. Effective amounts are anticipated to vary according to the formulation employed and other factors, as is known to one skilled in the art.

The amount of the p277, analogs derivatives and salts thereof in a pharmaceutical composition for enteral or mucosal administration without an adjuvant, which will be effective in the treatment of a particular disorder or condition, will depend on the nature of the disorder or condition, and can be determined by standard clinical techniques. In addition, in vitro assays may optionally be employed to help identify optimal dosage ranges. Suitable dosage ranges are between 5 ng and 1000 mg per day. The precise dose to be employed in the formulation will also depend on the route of administration, and the seriousness of the disease or disorder, and should be decided according to the judgment of the practitioner and each patient's circumstances. For example, for formulation administered by inhalation, the effective amount is likely to be less than that of the oral dose. This amount can be further refined by well-known methods, such as establishing a matrix of dosages and frequencies of administration. For sustained release formulations, the dose is determined such that the effective dose in the serum will be between about 1 and 100 ng/ml. Such determination is well within the abilities of the skilled artisan.

In various embodiments, compositions according to the invention can be delivered by a variety of means including intravenous, intramuscularly, infusion, oral, intranasal, intraperitoneal, subcutaneous, rectal, topical, buccal, transmucosal, transnasal, enteral, bronchial, or intrapulmonary or into other regions, such as into synovial fluids. Delivery of the composition transdermally is also contemplated, such by diffusion via a transdermal patch. For oral ingestion it is possible to prepare peptide analogs or specific peptide formulations having improved oral bioavailability and enhanced resistance to degradation as are known in the art.

The composition is administered in a manner compatible with the dosage formulation, and in a therapeutically effective amount. The quantity to be administered depends on the subject to be treated, capacity of the subject's blood hemostatic system to utilize the active ingredient. Precise amounts of active ingredient required to be administered depend on the judgment of the practitioner and are peculiar to each individual.

In order to treat a subject with a disease, a pharmaceutical composition of the present invention is administered to the subject in an effective manner such that the composition is capable of treating that subject from disease. According to the present invention, treatment of a disease refers to alleviating a disease and/or preventing the development of a secondary disease resulting from the occurrence of a primary disease. An effective administration protocol (i.e., administering a pharmaceutical composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease.

In accordance with the present invention, a suitable single dose size is a dose that is capable of treating a subject with disease when administered one or more times over a suitable time period. Doses can vary depending upon the disease being treated. Doses of a pharmaceutical composition of the present invention suitable for use with direct injection techniques can be used by one of skill in the art to determine appropriate single dose sizes for systemic administration based on the size of a subject.

A suitable single dose of a composition according to the invention is a sufficient amount of the active ingredient to reduce, and preferably eliminate, the T-cell mediated disorder, or the symptoms thereof. For example, a suitable single dose of a pharmaceutical composition comprising HSP60 or a HSP60 fragment is a sufficient amount of the HSP60 or HSP60 fragment to reduce, and preferably eliminate, a T-cell mediated hepatic disorder. A preferred single dose of HSP60 or HSP60 fragment for the treatment of hepatitis or preventing liver damage is between 5 ng and 50 µg, and preferably between 50 ng and 5 µg.

The pharmaceutical compositions of the invention may be used alone or in combination with one or more therapeutic agents. For example, a pharmaceutical compositions for the treatment of hepatitis according to the invention may be administered in combination with a drug including, but not limited to: interferon, ribavirin, or one or more other agents known in the art for the treatment or prevention of hepatitis, all of which administered together or separately, e.g., prior to, concurrently with or following the administration of the pharmaceutical compositions the invention.

Nucleic Acid-Based Compositions and Methods

According to another aspect, the present invention is directed to the use of a pharmaceutical composition comprising a recombinant construct comprising a nucleic acid sequence encoding a peptide selected from: p277 (SEQ ID NO:1), analogs and variants thereof, the nucleic acid sequence being operably linked to one or more transcription control sequences, and a pharmaceutically acceptable carrier, for the treatment and prevention of T cell mediated pathologies.

In one embodiment, the nucleic acid molecule encodes a p277 analog, in which at least one of the cysteine residues in positions 6 and 11 of p277 has been substituted. In one preferred embodiment, the encoded peptide is the p277 analog p277(Val$^6$Val$^{11}$) (SEQ ID NO:2). In another preferred embodiment, the encoded peptide is the p277 analog p277 (Ser$^6$Ser$^{11}$) (SEQ ID NO:3). In another embodiment, said construct comprises a nucleic acid sequence as set forth in any one of:

```
gtt ttg gga ggg ggt tgt gcc ctc ctt cga tgc att cca gcc ttg gac tca ttg act cca gct aat gaa gat (encoding p277, SEQ ID NO: 5);

gtt ttg gga ggg ggt gtt gcc ctc ctt cga gtc att cca gcc ttg gac tca ttg act cca gct aat gaa gat (encoding p277(Val⁶Val¹¹), SEQ ID NO: 6);
and gtt ttg gga ggg ggt tct gcc ctc ctt cga tcc att cca gcc ttg gac tca ttg act cca gct aat gaa gat (encoding p277(Ser⁶Ser¹¹), SEQ ID NO: 7).
```

In another aspect, the invention is directed to the use of a recombinant construct comprising a nucleic acid sequence encoding a peptide selected from: p277 (SEQ ID NO:1), analogs and variants thereof, the nucleic acid sequence being operably linked to one or more transcription control sequences for the preparation of a pharmaceutical composition for the treatment and prevention of T cell mediated pathologies or symptoms associated therewith.

In another aspect, the present invention provides a method of treating a T cell mediated pathology other than insulin-dependent diabetes mellitus and graft rejection in a subject in need thereof, comprising administering to the subject a therapeutically-effective amount of a pharmaceutical composition comprising a recombinant construct comprising a nucleic acid sequence encoding a peptide selected from: p277 (SEQ ID NO:1), analogs and variants thereof, the nucleic acid sequence being operably linked to one or more transcription control sequences; and a pharmaceutically acceptable carrier.

In another aspect, the present invention provides methods of preventing a T cell mediated pathology other than insulin-dependent diabetes mellitus and graft rejection in a subject in need thereof, comprising administering to the subject a therapeutically-effective amount of a pharmaceutical composition comprising a recombinant construct comprising a nucleic acid sequence encoding a peptide selected from: p277 (SEQ ID NO:1), analogs and variants thereof, the nucleic acid sequence being operably linked to one or more transcription control sequences; and a pharmaceutically acceptable carrier.

In another aspect, the present invention provides methods of treating or preventing a T cell mediated pathology other than insulin-dependent diabetes mellitus and graft rejection in a subject in need thereof, comprising administering to the subject a therapeutically-effective amount of a pharmaceutical composition comprising a recombinant construct comprising a nucleic acid sequence encoding a peptide selected from: p277 (SEQ ID NO:1), analogs and variants thereof, the nucleic acid sequence being operably linked to one or more transcription control sequences; and a pharmaceutically acceptable carrier.

According to another aspect, the present invention is directed to the use of a pharmaceutical composition comprising a recombinant construct, the recombinant construct comprising a nucleic acid sequence encoding a polypeptide or peptide selected from a group consisting of: HSP60 protein, an active fragment thereof, and analogs and variants thereof, the nucleic acid sequence being operably linked to one or more transcription control sequences, and a pharmaceutically acceptable carrier, for the treatment of hepatitis.

In one embodiment, the HSP60 protein is selected from the group consisting of: human HSP60, mammalian HSP60 and bacterial HSP60. In another embodiment, the HSP60 protein has an amino acid sequence as set forth in any one of SEQ ID NOS:4 and 11. In another embodiment, the HSP60 protein has an amino acid sequence as set forth in SEQ ID NO:9. In another particular embodiment, the HSP60 fragment is the p277 peptide, having an amino acid sequence as set forth in SEQ ID NO:1. In another embodiment, the HSP60 fragment analog has an amino acid sequence as set forth in SEQ ID NO:2. In yet another embodiment, the HSP60 fragment analog has an amino acid sequence as set forth in SEQ ID NO:3. In another embodiment, said construct comprises a nucleic acid sequence as set forth in any one of SEQ ID NOS:5-7. In another embodiment, the HSP60 protein is encoded by a nucleic acid sequence as set forth in SEQ ID NO:8 (encoding human HSP60, accession number M34664).

According to another aspect, the present invention is directed to the use of a pharmaceutical composition comprising a recombinant construct, the recombinant construct comprising a nucleic acid sequence encoding a polypeptide or peptide selected from a group consisting of: HSP60 protein, an active fragment thereof, and analogs and variants thereof, the nucleic acid sequence being operably linked to one or more transcription control sequences, and a pharmaceutically acceptable carrier, for preventing liver damage.

According to another aspect, the present invention is directed to the use of a recombinant construct comprising a nucleic acid sequence encoding a polypeptide selected from a group consisting of: HSP60 protein, an active fragment thereof, and analogs and variants thereof, the nucleic acid sequence being operably linked to one or more transcription control sequences for the preparation of a pharmaceutical composition useful for the treatment of hepatitis and/or prevention of liver damage.

In another aspect, the invention provides a method of treating hepatitis, comprising administering to a subject in need thereof a therapeutically effective amount of a pharmaceutical composition comprising as an active ingredient a recombinant construct, the recombinant construct comprising a nucleic acid sequence encoding a polypeptide selected from a group consisting of: HSP60 protein, an active fragment thereof, and analogs and variants thereof, wherein the nucleic acid sequence is operably linked to one or more transcription control sequences, thereby treating hepatitis.

The invention provides, in another aspect, a method of treating or preventing liver damage, comprising administering to a subject in need thereof a therapeutically effective amount of a pharmaceutical composition comprising as an active ingredient a recombinant construct, the recombinant construct comprising an isolated nucleic acid sequence encoding a polypeptide selected from a group consisting of: HSP60 protein, an active fragment thereof, and analogs and variants thereof, wherein the nucleic acid sequence is operably linked to one or more transcription control sequences, thereby treating or preventing liver damage.

In another aspect, there are provided methods of treating hepatitis and/or treating or preventing liver damage comprising the steps of (a) obtaining cells from a subject; (b) introducing a recombinant construct into the cells ex vivo, the construct comprising an isolated nucleic acid sequence encoding a polypeptide selected from a group consisting of: HSP60 protein, an active fragment thereof, and analogs and variants thereof, wherein the nucleic acid sequence is operably linked to one or more transcription control sequences; and (c) reintroducing said treated cells to the subject; wherein the HSP60 or fragment, analog or variant thereof is expressed in vivo in said treated cells in an amount sufficient to treat hepatitis.

The nucleic acid sequence corresponding to mammalian heat shock proteins may include DNA, RNA, or derivatives of either DNA or RNA. An isolated nucleic acid sequence encoding heat shock proteins can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologues thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional heat shock protein or an active fragment or peptide of the invention.

A nucleic acid molecule homolog can be produced using a number of methods known to those skilled in the art (see, for example, Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the peptide encoded by the nucleic acid. Techniques to screen for HSP60 and p277 activity are known to those of skill in the art (several non-limitative examples of these methods are described in the Examples below).

A polynucleotide or oligonucleotide sequence can be deduced from the genetic code of a protein, however, the degeneracy of the code must be taken into account. Nucleic acid sequences of the invention include sequences, which are degenerate as a result of the genetic code, which sequences may be readily determined by those of ordinary skill in the art.

The oligonucleotides or polynucleotides of the invention may contain a modified internucleoside phosphate backbone to improve the bioavailability and hybridization properties of the oligonucleotide or polynucleotide. Linkages are selected from the group consisting of phosphodiester, phosphotriester, methylphosphonate, phosphoroselenoate, phosphorodiselenoate, phosphoroanilothioate, phosphoroanilidate, phosphoramidate, phosphorothioate, phosphorodithioate or combinations thereof.

Additional nuclease linkages include alkylphosphotriester such as methyl- and ethylphosphotriester, carbonate such as carboxymethyl ester, carbamate, morpholino carbamate, 3'-thioformacetal, silyl such as dialkyl (C1-C6)- or diphenylsilyl, sulfamate ester, and the like. Such linkages and methods for introducing them into oligonucleotides are described in many references, e.g. reviewed generally by Peyman and Ulmann, Chemical Reviews, 90:1543-584 (1990).

The present invention includes a nucleic acid sequence of the present invention operably linked to one or more transcription control sequences to form a recombinant molecule. The phrase "operably linked" refers to linking a nucleic acid sequence to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, insect cells, and preferably in animal cells. More preferred transcription control sequences include, but are not limited to RSV control sequences, CMV control sequences, retroviral LTR sequences, SV-40 control sequences and β-actin control sequences as well as other sequences capable of controlling gene expression in eukaryotic cells. Additional suitable transcription control sequences include tissue-specific promoters and enhancers (e.g., T cell-specific and liver specific enhancers and promoters). Transcription control sequences of the present invention can also include naturally occurring transcription control sequences naturally associated with a gene encoding HSP60.

According to still further features in the described preferred embodiments the recombinant construct is a eukaryotic expression vector.

According to still further features in the described preferred embodiments the expression vector is selected from the group consisting of pcDNA3, pcDNA3.1 (+/−), pZeoSV2 (+/−), pSecTag2, pDisplay, pEF/myc/cyto, pCMV/myc/cyto, pCR3.1, pCI, pBK-RSV, pBK-CMV, pTRES and their derivatives.

According to the present invention, a host cell can be transfected in vivo (i.e., in an animal) or in vitro (i.e., outside of an animal, such as in tissue culture). Transfection of a nucleic acid molecule into a host cell can be accomplished by any method by which a nucleic acid molecule can be inserted into the cell. Transfection techniques include, but are not limited to, transfection, electroporation, microinjection, lipofection, adsorption, and protoplast fusion. Preferred methods to transfect host cells in vivo include lipofection and adsorption.

A recombinant cell of the present invention comprises a cell transfected with a nucleic acid molecule that encodes HSP60, p277 or an analog, fragment or variant thereof.

It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operably linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts. The activity of an expressed recombinant peptide of the present invention may be improved by fragmenting, modifying, or derivatizing nucleic acid molecules encoding such a peptide.

The pharmaceutical composition of the invention is administered to a subject in need of said treatment in a therapeutically effective amount. According to the present invention, a "therapeutically effective amount" is an amount that when administered to a patient is sufficient to inhibit, preferably to eradicate, a T cell mediated pathology, or in other embodiments, the T-cell mediated hepatic disorder or symptoms thereof. In a preferred embodiment, the subject is human.

In another embodiment of the present invention, a therapeutic composition further comprises a pharmaceutically acceptable carrier. As used herein, a "carrier" refers to any substance suitable as a vehicle for delivering a nucleic acid molecule of the present invention to a suitable in vivo or in vitro site. As such, carriers can act as a pharmaceutically acceptable excipient of a therapeutic composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in a subject or a specific cell (i.e., targeting earners). Examples of non-targeting carriers include, but are not limited to, water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a subject, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as "delivery vehicles". Delivery vehicles of the present invention are capable of delivering a therapeutic composition of the present invention to a target site in a subject. A "target site" refers to a site in a subject to which one desires to deliver a therapeutic composition. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a target cell can be introduced to the outer surface of a liposome delivery vehicle so as to target the delivery vehicle to the target cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

A preferred delivery vehicle of the present invention is a liposome. A liposome is capable of remaining stable in a subject for a sufficient amount of time to deliver a nucleic acid molecule of the present invention to a preferred site in the subject. A liposome of the present invention is preferably stable in the subject into which it has been administered for at least about 30 minutes, more preferably for at least about 1 hour and even more preferably for at least about 24 hours.

A liposome of the present invention comprises a lipid composition that is capable of targeting a nucleic acid molecule of the present invention to a particular, or selected, site in a subject. Preferably, the lipid composition of the liposome is capable of targeting to any organ of a subject, more preferably to the lung, liver, spleen, heart brain, lymph nodes and skin of a subject.

A liposome of the present invention comprises a lipid composition that is capable of fusing with the plasma membrane of the targeted cell to deliver a nucleic acid molecule into a cell. Preferably, the transfection efficiency of a liposome of the present invention is about 0.5 microgram (µg) of DNA per 16 nanomole (nmol) of liposome delivered to about $10^6$ cells, more preferably about 1.0 µg of DNA per 16 nmol of liposome delivered to about $10^6$ cells, and even more preferably about 2.0 µg of DNA per 16 nmol of liposome delivered to about $10^6$ cells.

A preferred liposome of the present invention is between about 100 and 500 nanometers (nm), more preferably between about 150 and 450 nm and even more preferably between about 200 and 400 nm in diameter.

Suitable liposomes for use with the present invention include any liposome. Preferred liposomes of the present invention include those liposomes standardly used in, for example, gene delivery methods known to those of skill in the art. More preferred liposomes comprise liposomes having a polycationic lipid composition and/or liposomes having a cholesterol backbone conjugated to polyethylene glycol.

Complexing a liposome with a nucleic acid molecule of the present invention can be achieved using methods standard in the art. A suitable concentration of a nucleic acid molecule of the present invention to add to a liposome includes a concentration effective for delivering a sufficient amount of nucleic acid molecule to a cell such that the cell can produce sufficient therapeutic protein or peptide to regulate effector cell immunity in a desired manner. Preferably, from about 0.1 µg to about 10 µg of nucleic acid molecule of the present invention is combined with about 8 nmol liposomes, more preferably from about 0.5 µg to about 5 µg of nucleic acid molecule is combined with about 8 nmol liposomes, and even more preferably about 1.0 µg of nucleic acid molecule is combined with about 8 nmol liposomes.

Another preferred delivery vehicle comprises a recombinant virus particle vaccine. A recombinant virus particle vaccine of the present invention includes a therapeutic composition of the present invention, in which the recombinant molecules contained in the composition are packaged in a viral coat that allows entrance of DNA into a cell so that the DNA is expressed in the cell. A number of recombinant virus particles can be used, including, but not limited to, those based on alphaviruses, poxviruses, adenoviruses, herpesviruses, arena virus and retroviruses.

In order to treat a subject with disease, a therapeutic composition of the present invention is administered to the subject in an effective manner such that the composition is capable of treating that subject from disease. For example, a recombinant molecule, when administered to a subject in an effective manner, is able to stimulate effector cell immunity in a manner that is sufficient to alleviate the disease afflicting the subject. According to the present invention, treatment of a disease refers to alleviating a disease and/or preventing the development of a secondary disease resulting from the occurrence of a primary disease. An effective administration protocol (i.e., administering a therapeutic composition in an effective manner) comprises suitable dose parameters and modes of administration that result in treatment of a disease. Effective dose parameters and modes of administration can be determined using methods standard in the ail for a particular disease. Such methods include, for example, determination of survival rates, side effects (i.e., toxicity) and progression or regression of disease.

In accordance with the present invention, a suitable single dose size is a dose that is capable of treating a subject with disease when administered one or more times over a suitable time period. Doses can vary depending upon the disease being treated. Doses of a therapeutic composition of the present invention suitable for use with direct injection techniques can be used by one of skill in the art to determine appropriate single dose sizes for systemic administration based on the size of a subject. A suitable single dose of a therapeutic composition to treat a T-cell mediated pathology is a sufficient amount of recombinant sequence to reduce, and preferably eliminate, the T-cell mediated pathology following transfection of the recombinant molecules into cells. A preferred single dose of HSP60, p277 or fragments and analogs thereof-encoding recombinant molecule is an amount that, when transfected into a target cell population leads to the production of from about 250 femtograms (fg) to about 1 µg, preferably from about 500 fg to about 500 picogram (pg), and more preferably from about 1 pg to about 100 pg of p277 per transfected cell.

A preferred single dose of HSP60, p277 or fragments and analogs thereof-encoding recombinant molecule complexed with liposomes, is from about 100 ug of total DNA per 800 nmol of liposome to about 2 mg of total recombinant molecules per 16 micromole (µmol) of liposome, more preferably from about 150 µg per 1.2 µmol of liposome to about 1 mg of total recombinant molecules per 8 µmol of liposome, and even more preferably from about 200 µg per 2 µmol of liposome to about 400 ug of total recombinant molecules per 3.2 µmol of liposome.

A preferred single dose of HSP60, p277 or fragments and analogs thereof-encoding recombinant molecule in a non-targeting carrier to administer to a subject, is from about 12.5 µg to about 30 mg of total recombinant molecules per kg body weight, more preferably from about 25 µg to about 10 mg of total recombinant molecules per kg body weight, and even more preferably from about 125 µg to about 3 mg of total recombinant molecules per kg body weight.

It will be obvious to one of skill in the art that the number of doses administered to a subject is dependent upon the extent of the disease and the response of an individual patient to the treatment. Thus, it is within the scope of the present invention that a suitable number of doses includes any number required to cause regression of a disease. A preferred protocol is monthly administrations of single doses (as described above) for up to about 1 year. A preferred number of doses of a therapeutic composition comprising a recombinant molecule of the invention in a non-targeting carrier or complexed with liposomes is from about 1 to about 10 administrations per patient, preferably from about 2 to about 8 administrations per patient, and even more preferably from about 3 to about 5 administrations per person. Preferably, such administrations are given once every 2 weeks until signs of remission appear, then once a month until the disease is gone.

A therapeutic composition is administered to a subject in a fashion to enable expression of the administered recombinant molecule of the present invention into a curative protein in the subject to be treated for disease. A therapeutic composition can be administered to a subject in a variety of methods including, but not limited to, local administration of the composition into a site in a subject, and systemic administration.

Therapeutic compositions to be delivered by local administration include: (a) recombinant molecules of the present invention in a non-targeting carrier (e.g., as "naked" DNA molecules, such as is taught, for example in Wolff et al., 1990); and (b) recombinant molecules of the present invention complexed to a delivery vehicle of the present invention. Suitable delivery vehicles for local administration comprise liposomes. Delivery vehicles for local administration can further comprise ligands for targeting the vehicle to a particular site.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site. Systemic administration is particularly advantageous when organs, in particular difficult to reach organs (e.g., heart, spleen, lung or liver) are the targeted sites of treatment.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., 1992, which is incorporated herein by reference in its entirety). Oral delivery can be performed by complexing a therapeutic composition of the present invention to a carrier capable of withstanding degradation by digestive enzymes in the gut of a subject. Examples of such carriers include plastic capsules or tablets, such as those known in the art. Topical delivery can be performed by mixing a therapeutic composition of the present invention with a lipophilic reagent (e.g., DMSO) that is capable of passing into the skin.

T Cell Vaccination

In another aspect, the invention provides a pharmaceutical composition comprising attenuated activated T cells exposed ex vivo to a compound selected from a group consisting of:

p277 (SEQ ID NO:1), analogs, variants, derivatives and salts thereof.

In certain embodiments, at least one of the cysteine residues in positions 6 and 11 of p277 has been substituted. In another embodiment, the p277 analog is p277(Val$^6$Val$^{11}$) (SEQ ID NO:2). In another embodiment, the p277 analog is p277(Ser$^6$Ser$^{11}$) (SEQ ID NO:3).

According to this aspect, such T cell vaccines (TCV) preferably include cell vaccines in which allogeneic (i.e., cells derived from a source other than a patient, but that are histocompatible with the patient) or autologous (i.e., cells isolated from a patient) cells are activated in vitro to induce Major Histocompatibility Complex (MHC) II expression, exposed to p277 or analogs, variants, derivatives and salts thereof contained in a therapeutic composition, attenuated and administered to a patient by, for example, intradermal, intravenous or subcutaneous injection. In one embodiment, the patient is human.

Suitable antigen-nonspecific agents capable of activating T cells are known in the art and include, but are not limited to, mitogens such as concanavalin A, phytohemagglutinin, and pokeweed mitogen. Additional activating agents are antibodies to T cell-surface structures, including but not limited to, antibodies to the CD3 cell-surface molecule, antibodies to the CD2 cell-surface molecule, antibodies to the CD28 cell-surface molecule, and the natural ligands of CD2 or CD28. Other activating agents include phorbol esters, such as phorbol myristate acetate, or a combination of a phorbol ester and a calcium ionophore, such as ionomycin. Also intended as T cell activating agents are antibodies to the T cell receptor chains. Upon activation by such agents, T cells up regulate various surface markers, including, but not limited to major histocompatibility complex (MHC) II, and may express p277 epitopes in the context of MHC II, as disclosed herein.

The T lymphocyte activation step of the present invention may or may not include the addition of T cell growth factors or stimulatory factors, such as, for example, IL-1, IL-2 or IL-4, to the culture medium for part or all of the activation interval.

Treatment to attenuate the T lymphocytes, may include, but is not limited to, gamma- or X-irradiation, or treatment with mitomycin C, by methods well known in the art, may also be used according to the invention (Ben-Nun, et al., 1987, Holoshitz et al., 1983). In one particular embodiment, the cells are attenuated by exposure to gamma irradiation (2000-10000 rads).

In another aspect, the invention provides methods of treating or preventing a T cell mediated pathology in a subject in need thereof, comprising: (a) isolating T cells from the subject or from a donor histocompatible with said subject; (b) activating the T cells ex vivo to induce Major Histocompatibility Complex (MHC) II expression; (c) exposing said activated cells to a compound selected from a group consisting of: p277 (SEQ ID NO:1), analogs, variants, derivatives and salts thereof; (d) attenuating said T cells; and (e) introducing said cells into the subject in an amount sufficient to induce an anti-ergotypic response in said subject.

In certain embodiments, at least one of the cysteine residues in positions 6 and 11 of p277 has been substituted. In another embodiment, the p277 analog is p277(Val$^6$Val$^{11}$) (SEQ ID NO:2). In another embodiment, the p277 analog is p277(Ser$^6$Ser$^{11}$) (SEQ ID NO:3).

Effective amounts of cells to be introduced into the subject may be extrapolated from animal model test bioassays or systems. Suitable amounts of attenuated p277-loaded T cells are preferably between $10^6$-$10^8$ cells per administration.

In other aspects, the invention provides T cell vaccine compositions and methods thereof using adoptive transfer of p277-specific anti-ergotypic cells.

The generation of antigen-specific cell lines is within the abilities of those of skill in the art, and is currently being applied for the development of therapeutic TCV (see, for example, Achiron et al., 2004). For the generation of p277-specific anti-ergotypic cells suitable for adoptive transfer TCV, a first population of T cells is activated by incubation in the presence of a second population of p277-loaded attenuated activated T cells as described above. Such attenuated T cells may be incubated with p277 or analogs, variants, derivatives and salts thereof prior to incubation with the first T cell population, or alternatively be incubated with the first T cell population in the presence of p277 or analogs, variants, derivatives and salts thereof. p277-specific anti-ergotypic T cells present in the first population recognize p277 epitopes presented on MHC II molecules of the second activated T cell population. It is to be understood, therefore, that both T cell populations used are histiotype compatible (histocompatible) with each other as well as with the subject in need of said treatment. Advantageously, this activation step is repeated at least once (and is typically performed 2-3 times), in order to enrich the resulting T cell population for the desired p277-specific anti-ergotypic T cells. The method may optionally further comprise one or more steps of expanding the resulting p277-specific anti-ergotypic-enriched T cell population, e.g. by culturing in the presence of IL-2. The resulting T cell population is then administered to said subject in an amount sufficient to induce an anti-ergotypic response in said subject. Suitable amounts of p277 specific anti-ergotypic-enriched T cells are preferably between $10^7$-$3\times 10^7$ cells per administration.

In one embodiment, T cells are the majority of the cells used to produce the T cell vaccines according to the invention. In some embodiments, the T cells are substantially pure of other antigen presenting cells. In various embodiments, the T cell populations used in accordance with the present invention contain at least 90%, preferably at least 95% and more preferably at least 97% T cells of the total cell population.

The use of HSP60, active fragments thereof, p277, analogs, variants, derivatives and salts thereof for the preparation of a T cell vaccine for the treatment of hepatitis or liver damage associated therewith is further disclosed by the present invention.

In another aspect, the invention provides methods of treating hepatitis or liver damage associated therewith in a subject in need thereof, comprising: (a) isolating T cells from the subject or from a donor histocompatible with said subject; (b) activating the T cells ex vivo to induce Major Histocompatibility Complex (MHC) II expression; (c) exposing said activated cells to a compound selected from a group consisting of: HSP60, an active fragment thereof, p277 (SEQ ID NO:1), analogs, variants, derivatives and salts thereof; (d) attenuating said T cells; and (e) introducing said T cells into the subject in an amount sufficient to induce an anti-ergotypic response in said subject.

In another aspect, the invention provides methods of treating hepatitis or liver damage associated therewith in a subject in need thereof, comprising: (a) isolating a first population of T cells from the subject or from a donor histocompatible with said subject; (b) culturing the first population of T cells in the presence of a second population of histocompatible attenuated activated T cells and a compound selected from a group consisting of: HSP60, an active fragment thereof, p277 (SEQ ID NO:1), analogs, variants, derivatives and salts thereof; and (C) introducing said first population of T cells into the subject in an amount sufficient to induce an anti-ergotypic response in said subject.

It is to be noted that the compositions and methods of the present invention do not include the obligatory presence of a second peptide capable of eliciting a reaction via a T cell receptor conjugated to p277 to form a "dual-effect ligand", as disclosed in WO 03/070761.

The following examples are presented in order to more fully illustrate some embodiments of the invention. They should, in no way be construed, however, as limiting the broad scope of the invention.

EXAMPLES

A. p277 is Presented by Activated T Cells to Anti-Ergotypic Regulatory T Cells

Rats. Female Lewis rats were raised and maintained under pathogen-free conditions in the Animal Breeding Center of this institute. Experiments were carried out under the supervision and guidelines of the Animal Welfare Committee. The rats were 1-2 months old at the start of the experiments.

Antigens, peptides, antibodies and adjuvants. *M. tuberculosis* (Mt) strain H37Ra was obtained from Difco (Detroit, Mich., USA). Mt purified protein derivative (PPD) was provided by the Statens Seruminstitut (Copenhagen, Denmark). Recombinant mycobaterial 65 kDa HSP (HSP65) was kindly provided by Dr. Ruurd van der Zee (Institute of Infectious Diseases and Immunology, Faculty of Veterinary Medicine, Utrecht, The Netherlands). Recombinant HSP60 was prepared as described (Quintana et al., 2000). Guinea pig myelin basic protein (MBP) was purchased from Sigma (Rehovot, Israel). Two HSP65 peptides were used: MU76-190 (aa 176-190) EESNTFGLQLELTEG (Anderton et al., 1994, SEQ ID NO:14) and Mt3 (aa 5-24) AYDEEARRGLERGLNALADA (Quintana et al., 2003, SEQ ID NO:15). The Mt176-90 peptide used in this work includes the 180-188 epitope (van Eden et al., 1988). Two peptides derived from HSP60 were used in Examples 1-8: p277 (aa 437-460) VLGGGCALLRCIPALD-SLTPANED (SEQ ID NO:1) and Hu3 (aa 31-50) KFGADA-RALMLQGVDLLADA (SEQ ID NO:16). Peptides were synthesized by a standard Fmoc procedure, purified by reverse-phase HPLC and their compositions confirmed by aa analysis. Concanavalin A (Con A) was purchased from Sigma. Incomplete Freund's Adjuvant (IFA) was purchased from Difco.

A monoclonal antibody reactive to rat TCR (clone R73) was purified by us from the hybridoma. Monoclonal antibodies to MHC class-I (MHC-I), MHC class-II RT1.B (MHC-II/RT1.B), MHC class-II RT1.D (MHC-II/RT1.D), CD28, CD80 and CD86 were purchased from Serotec (Oxford, UK). Purified rabbit anti-human HSP60 polyclonal IgG antibodies were provided by Dr Gabriel Nussbaum (Department of Immunology, The Weizmann Institute of Science, Israel).

T-cell lines and clones T-cell lines were raised and expanded using antigen presenting cells (APC) and antigens or peptides as described (Mor et al., 1992). Three Lewis rat T-cell lines were used in our experiments: Anti-HSP60, raised against recombinant human HSP60 (human HSP60 is 97% identical to rat HSP60 at the aa level); Anti-p277, raised against the p277 peptide of human HSP60 (96% identical its rat counterpart at the aa level) and Anti-MBP, raised against guinea pig MBP. For ergotypic stimulation, the A2b T-cell clone, specific for the 180-188 epitope of HSP65 (van Eden et al., 1988) was used; similar results were obtained when other rat T-cell clones were used as targets. A2b expresses MHC-I molecules constitutively and CD80, CD86 and MHC-II molecules upon activation, and can present peptide epitopes to T cells. Activated A2b cells were used on day 3 of their stimulation, and resting A2b cells were used on day 14-16 of their rest cycle, unless stated otherwise.

DNA and peptide vaccination. The vectors containing the full-length cDNA of the human hsp60 gene (pHSP60) or the cDNA corresponding to aa 1-140 (pI) or aa 130-260 (pII) have been previously described (Quintana et al., 2002, Quintana et al., 2002b, Quintana et al., 2003, Quintana et al., 2000). The vector coding for mycobacterial HSP65 (pHSP65) was kindly provided by Dr. Douglas Lowrie (Medical Research Council, London, UK) (Ragno et al., 1997). The empty vector pcDNA3 was used as a DNA vaccination control.

Plasmid DNA was prepared in large scale and injected after pretreatment with cardiotoxin (Sigma) as previously described (Quintana et al., 2002b). Briefly, rats were vaccinated in the quadriceps three times (on days −40, −26-12 relative to AA induction) with 150 µg of pcDNA3, pHSP65 or pHSP60. Endotoxin levels were checked by the *Limulus* amoebocyte lysate assay and found always to be under acceptable levels for in vivo use (less than 0.02 EU/µg DNA).

Female Lewis rats were immunized intraperitoneally (ip) with a single dose of 100 µg of peptide emulsified in IFA. AA was induced 12 days after the completion of vaccination with DNA or peptide.

AA Induction and Assessment. AA was induced using heat-killed Mt strain H37Ra (Difco) suspended in IFA, as described (Quintana et al., 2002b). The day of AA induction was designated as day 0. Disease severity was assessed by direct observation of all 4 limbs in each animal. A relative score between 0 and 4 was assigned to each limb, based on the degree of joint inflammation, redness and deformity; thus the maximum possible score for an individual animal was 16. Arthritis was also quantified by measuring hind limb diameter with a caliper. Measurements were taken on the day of the induction of AA and 26 days later, at the peak of AA (Quintana et al., 2002b); the results are presented as the mean±SEM of the difference between the values for hind limb diameter taken on days 0 and 26.

Anti-ergotypic T-cell proliferation assay. T-cell lines or lymph node cells (LNC, prepared from inguinal and popliteal lymph nodes) were cultured in quadruplicates, $2.5 \times 10^5$ per well, in round-bottom microtiter wells (Nunc, Roskilde, Denmark). Activated or resting A2b stimulator cells were irradiated (5000 R) and added to the test cultures in 2-fold dilutions, starting from $10^5$ cells per well, with no other APC. Con A (1.25 µg/ml) was used as a positive control for T-cell proliferation, and in some experiments the cells were activated with immobilized anti-TCR antibodies as described (Wang et al., 2002). Monoclonal antibodies, 10 µg/ml, were added where indicated to test for MHC restrictions or co-stimulation requirements of the anti-ergotypic T cells. Cultures were incubated for 72 hr at 37° C. in 7% $CO_2$, and pulsed for the last 16 hr with 1 µCi/well of [methyl-$^3$H]-thymidine (Amersham, Buckinghamshire, UK). The cultures were harvested and cpm were determined using a beta counter. The ΔCPM was computed as the difference between the mean cpm of wells containing activated or resting A2b stimulator cells to control wells cultured with medium alone.

Cytokine assays. Supernatants were collected after 72 hr of stimulation with test antigens or stimulator cells. Pharmingen's OPTEIA IL-10, IL-4 and IFNγ kits (Pharmingen, San Diego, USA) and the TGFβ1 $E_{max}$® ImmunoAssay System (Promega, Madison, USA) were used to quantify cytokine release to culture supernatants, as previously described (Quintana et al., 2002b). The lower limits of detection for the experiments described in this paper were 15 pg/ml for TGFβ1, IL-10, IL-4 and IFNγ.

Western blotting. Cell lysates of resting or activated T cells were prepared by treatment for 15 minutes in the following lysis buffer: NP40 1%, NaCl 0.9%, Tris 50 mM, EDTA 1 mM, PMSF 0.4 mM, pepstatin A 4 µg/ml, leupeptin 4 µg/ml and aprotinin 4 µg/ml. The lysates were centrifuged for 15 min at 14000 rpm and the protein concentration in the supernatant was determined using a BCA protein assay kit (Pierce, Rockford, Ill., USA). The lysates were subjected to PAGE-SDS using a mini-gel apparatus (Bio-Rad Laboratories, Hercules, Calif.); 100 µg of each sample were loaded per well. Two identical gels were run each time in parallel: one gel was stained with Coomassie Brilliant Blue R-250 according to the manufacturer's protocol (Bio-Rad) and the other was electrotransferred to nitrocellulose membranes (Schleicher and Schuell, Dassel, Germany).

The nitrocellulose membranes were washed with PBS and then blocked for 1 hr with 2% bovine serum albumin (Sigma), 2.5% milk powder (Bio-Rad), Tris (Sigma) pH 7.5 10 mM, NaCl 150 mM and 0.02% thimerosal (Sigma). After washing with PBS/Tween 20 (PBST; 0.02%, Sigma), the membranes were incubated in blocking solution for 2 hr with HSP60-specific polyclonal antibodies. The membranes were washed with PBST and incubated with a peroxidase-conjugated goat anti-rabbit IgG (Jackson Immuno-Research, West Grove, Pa.) at a 1/10000 dilution in blocking solution for 1 hr. Finally, the membranes were developed using the Western Blotting Luminol Reagent (Santa Cruz Biotechnology Inc., Santa Cruz, Calif., USA), exposed to X-ray film and quantified using the NIH Image 1.63 program (National Institutes of Health, USA). Size was determined using pre-stained broad-range protein standard markers (Bio-Rad).

Adoptive transfer of anti-ergotypic T cells. Anti-p277 or Anti-MBP T cells were activated for 3 days in culture. Blast cells were isolated using a LymphoPrep gradient (Nycomed, Oslo, Norway), washed, and $5 \times 10^6$ cells per rat were injected ip. Three days later, AA was induced.

Statistical significance. The InStat 2.01 program was used for statistical analysis. Student's t-test and the Mann-Whitney test were carried out to assay significant differences between the different experimental groups.

Example 1

DNA Vaccination with pHSP60 Activates Anti-Ergotypic Responses

Figure 1B:
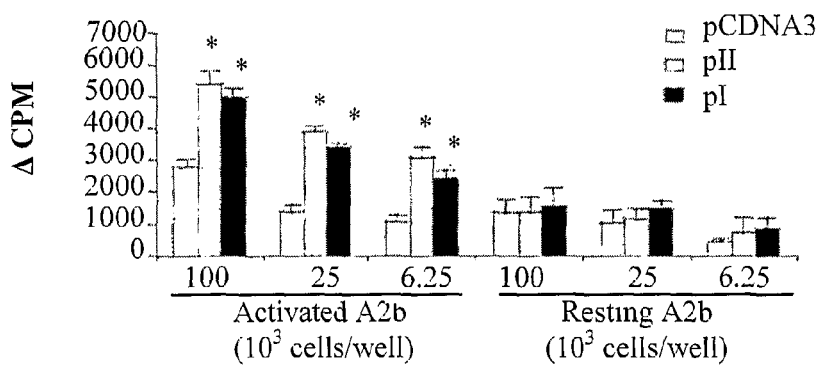
Figure 1C:
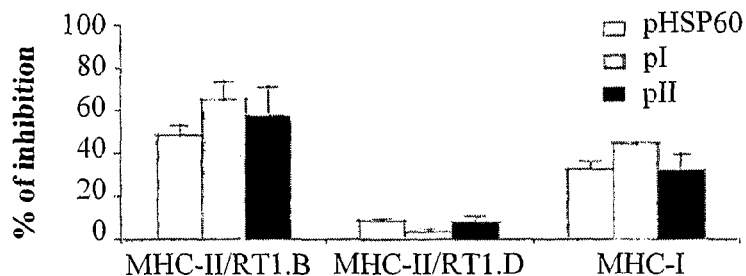

The inventors have reported that DNA vaccination with the hsp60 gene (pHSP60) or with its N-terminal fragments—constructs pI or pII—induced HSP60-specific T cells and inhibited the development of AA (Quintana et al., 2002b, Quintana et al., 2003). DNA vaccination with mycobacterial HSP65 (pHSP65) also protected rats against AA (Ragno et al., 1997), but this vaccination was significantly less effective than was vaccination with self-HSP60 (Quintana et al., 2002b). Does protective HSP60 vaccination activate anti-ergotypic reactivity? To approach this question, the anti-ergotypic T-cell responses in rats vaccinated with pHSP60, pI, pII, pHSP65 or pcDNA3, 26 days after the induction of AA, were studied. Lymph node cells (LNC) of the vaccinated rats were incubated with irradiated activated or resting A2b T cells, and proliferative responses were measured to different numbers of A2b stimulator cells. FIG. 1A shows that vaccination with pHSP60 induced a proliferative anti-ergotypic T-cell response, which was significantly ($p<0.05$) higher than that induced by pHSP65; control vaccination with pcDNA3 was least effective. Moreover, vaccination with the pI or pII constructs of HSP60 also induced a significant ($p<0.05$) anti-ergotypic response compared to pcDNA3 (FIG. 1B). Using neutralizing antibodies, the inventors found that the anti-ergotypic response induced by DNA vaccination included both MHC-II (RT1.B) and MHC-I restricted T cells (FIG. 1C).

Figure 1D:
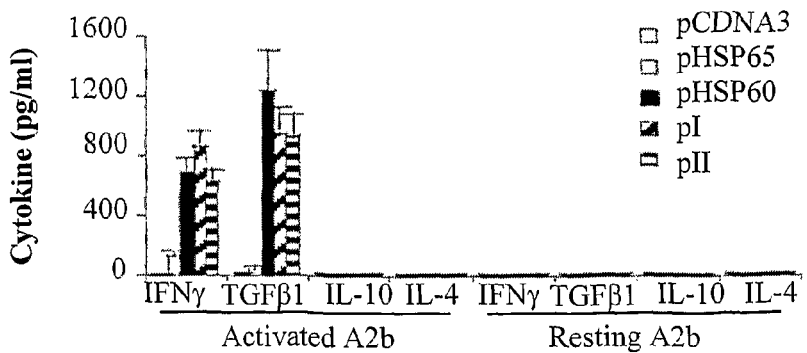

Note that the pHSP60 DNA vaccine also increased the response to resting A2b T cells, but to a lower extent than to activated A2b T cells (FIG. 1A). However, only activated A2b T cells induced cytokine secretion—characterized by secretion of IFN$\gamma$ and TGF$\beta$1, but not of IL-10 or IL-4 (FIG. 1D).

Example 2

Peptide Hu3 of HSP60 Activates an Anti-Ergotypic Response

Figure 2A:
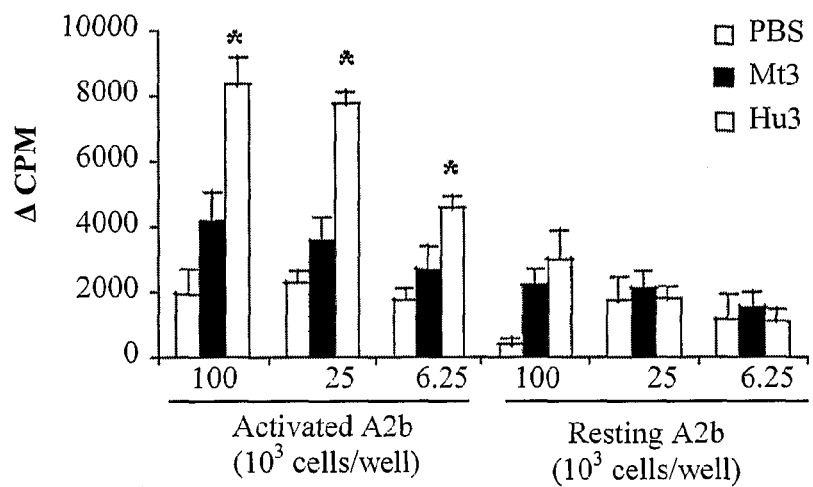
FIG. 2. Vaccination with HSP60 peptide Hu3 induces anti-ergotypic T cells. A. Anti-ergotypic proliferative response of LNC from rats vaccinated with PBS, Mt3 or Hu3 in IF A, taken 26 days after AA induction. Proliferative responses are presented as the ΔCPM±SEM of quadruplicate cultures. * $p<0.05$ compared to the Mt3 group. B. Monoclonal antibodies to MHC-II/RT1.B, MHC-II/RT1.D or MHC-I were assayed for their ability to block the anti-ergotypic proliferative response. Results are presented as the percent of inhibition of proliferation±SEM of quadruplicate cultures. C. Anti-ergotypic cytokine response of LNC taken from rats vaccinated with PBS, Mt3 or Hu3 in IF A, 26 days after AA induction. IFNγ, TGFβ1, IL-10 and IL-4 were quantified in the culture supernatants after 72 hr of stimulation with $10^5$ activated or resting, irradiated, A2b cells per well. The results are presented as pg/ml±SEM of triplicate cultures. Three independent experiments produced similar results.
Figure 2B:
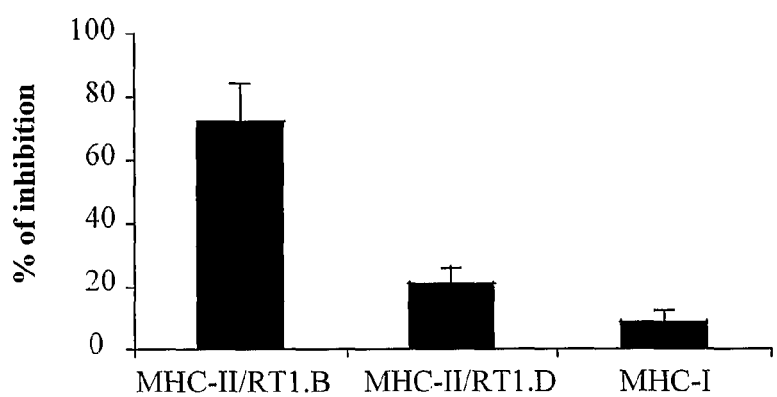
Figure 2C:
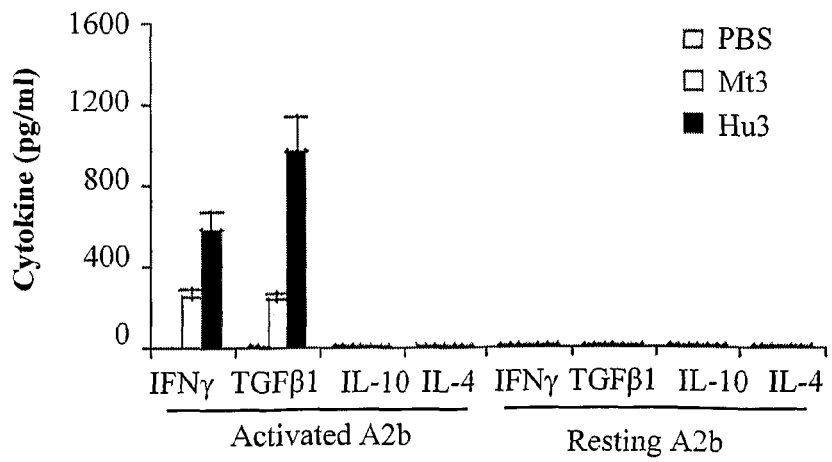

Vaccination with the HSP60 peptide Hu3 (aa 31-50) can also inhibit AA (Quintana et al., 2003). Does effective HSP60-peptide vaccination also induce an anti-ergotypic response? FIG. 2A shows that vaccination with peptide Hu3 was significantly ($p<0.05$) more effective in inducing an anti-ergotypic proliferative response than was vaccination with the homologous, immunogenic Mt3 peptide from mycobacterial HSP65. The anti-ergotypic proliferative response induced by peptide Hu3 was also more focused in its MHC-II restriction (FIG. 2B); recall that HSP60 DNA vaccination led to anti-ergotypic proliferative responses that included both MHC-I and MHC-II restricted T cells (FIG. 1C). The anti-ergotypic T cells induced by Hu3 peptide vaccination secreted IFN$\gamma$ and TGF$\beta$1, but not IL-10 or IL-4 in response to activated A2b T cells (FIG. 2C).

Example 3

T-Cell Activation Up-Regulates HSP60 Expression

Figure 3A:
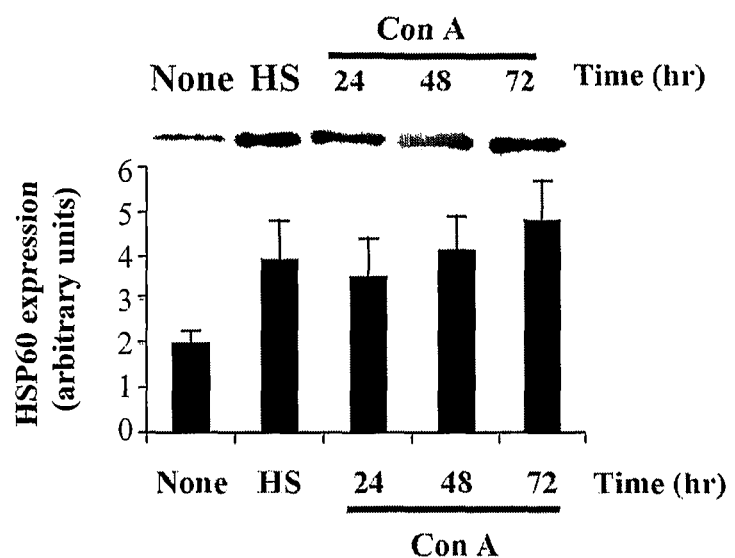
FIG. 3. T-cell activation up-regulates cellular levels of HSP60. A. LNC were stimulated with Con A for 24, 48 or 72 hr, subjected to a 30 minutes 42° C. heat shock (HS) or kept at 37° C. (None). Cell lysates were prepared and HSP60 expression was analyzed by western blot with specific antibodies, and quantified (in arbitrary units). B. A2b T-cells were stimulated with various concentrations of the target peptide Mt176-90, a control peptide (Mt3) for 72 hr, or with medium alone (None). Cell lysates were prepared and HSP60 expression was analyzed by western blot with specific antibodies, and quantified (in arbitrary units). Two independent experiments produced similar results.

The above results (FIGS. 1 and 2) indicated that the inhibition of AA by HSP60 DNA or peptide vaccination was associated with the induction of anti-ergotypic proliferative and cytokine responses to activated, syngeneic T cells; but do epitopes of HSP60 function as ergotopes? Is HSP60 up-regulated and presented on activated T cells to anti-ergotypic T cells? To study this question, the inventors compared the expression of HSP60 in activated or resting T cells by western blot. LNC were incubated for 1, 2 or 3 days with the T-cell mitogen Con A, or left untreated. Cell lysates were prepared at the end of the incubation, standardized by protein content, and analyzed by western blot for the expression of HSP60. As a positive control for the induction of HSP60, LNC were also heat shocked for 30 minutes at 42° C. and allowed to recover for 4 hr at 37° C. FIG. 3A shows that T-cell activation with Con A or heat shock triggered a similar increase in the expression levels of HSP60. No differences in total protein content were seen when the different samples were analyzed by PAGE-SDS.

Figure 3B:
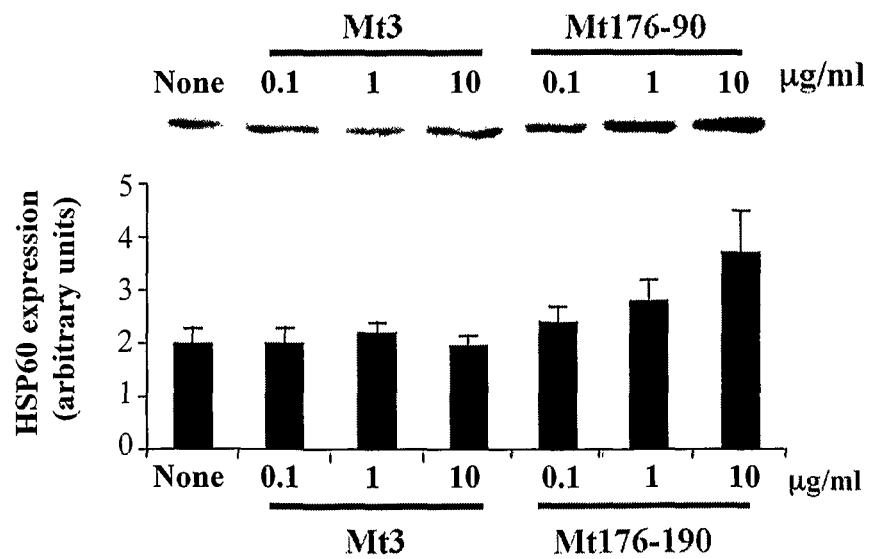

The inventors also detected up-regulation of HSP60 following activation of the T-cell clone A2b by its target peptide epitope Mt176-90 but not by the control peptide Mt3 (FIG. 3B); no differences in total protein were seen when the samples were analyzed by PAGE-SDS. The up-regulation of HSP60 protein is in agreement with previous studies done at the level of mRNA expression (Ferris et al., 1988), and demonstrates that T-cell activation by specific antigen leads to the up-regulation of cellular HSP60.

Example 4

Activated T Cells Stimulate HSP60-Specific and p277-Specific T Cells

Figure 4A:
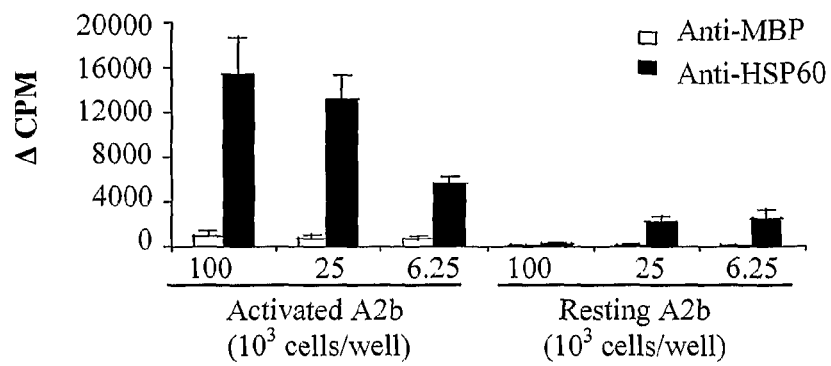
FIG. 4. MHC class II-restricted recognition of activated T cells by HSP60-specific T-cells. A. Anti-ergotypic proliferative response of Anti-HSP60 or Anti-MBP T cell lines. Proliferative responses are presented as the ACPM±SEM of quadruplicate cultures. B. Anti-ergotypic proliferative response of Anti-p277 or Anti-MBP T cell lines. Proliferative responses are presented as the ΔCPM±SEM of quadruplicate cultures. C. Monoclonal antibodies to MHC-II/RT1.B, MHC- II/RT1.D or MHC-I were assayed for their ability to block the anti-ergotypic proliferative response of the Anti-HSP60 and the Anti-p277 T cell lines. Results are presented as the percent of inhibition of proliferation±SEM of quadruplicate cultures. D. IFNγ, TGFβ1, IL-10 and IL-4 were quantified in the culture supernatants after 72 hr of stimulation of the Anti-MBP, Anti-p277 or Anti-HSP60 T cell lines with $10^5$ activated or resting, irradiated, A2b cells per well. The results are presented as pg/ml±SEM of triplicate cultures. Three to five independent experiments produced similar results.
Figure 4B:
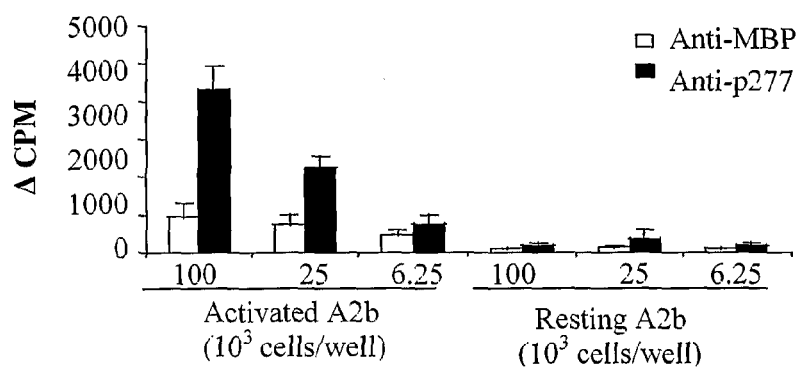
Figure 4C:
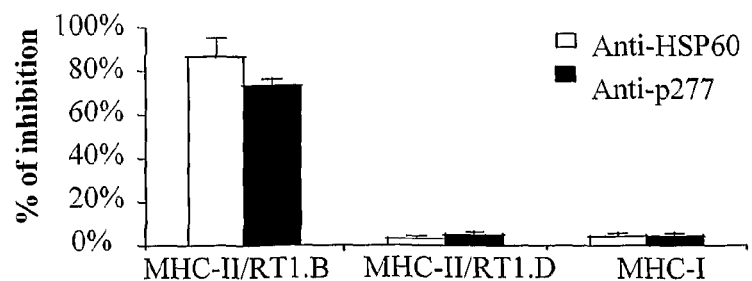

Are HSP60 epitopes actually presented by activated T cells? The inventors studied this question using HSP60-specific T-cell lines as probes for HSP60-epitope presentation, and a control T-cell line specific for MBP. Activated or resting A2b T cells were irradiated to inhibit their proliferation, and their presentation of HSP60 epitopes was probed with the test T-cell lines. FIG. 4A shows that the Anti-HSP60 T cells proliferated upon incubation with activated A2b; the response to resting A2b T-cells was marginal. The reaction to HSP60 was specific; the Anti-MBP T cells failed to respond to the A2b T cells, irrespective of their state of activation. Thus, only the activated A2b T cells presented HSP60 epitopes recognizable by the Anti-HSP60 line. The proliferation of the Anti-HSP60 line was restricted through the MHC-II/RT1.B molecule (FIG. 4C).

The 437-60 region of HSP60 (contained in the HSP60 peptide designated p277) is an immunodominant T-cell epitope in the Lewis rat (Reizis et al., 1996). The inventors could therefore use an Anti-p277 T-cell line to investigate whether activated A2b T cells presented the defined HSP60 peptide epitope p277. Although less than the Anti-HSP60 T-cell line (compare FIGS. 4A and 4B), the Anti-p277 T cells showed a significant proliferation upon incubation with activated A2b T cells (FIG. 4B), but not with resting A2b T cells. This anti-ergotypic proliferative response was MHC-II/RT1.B restricted (FIG. 4C). Thus, activated T cells can present a specific epitope of their up-regulated HSP60 molecules; that this occurs in the absence of any other APC, suggests that activated T cells can process and present epitopes of their own HSP60. Thus, T-cell presentation of HSP60 can reveal the state of activity of a T cell.

Figure 4D:
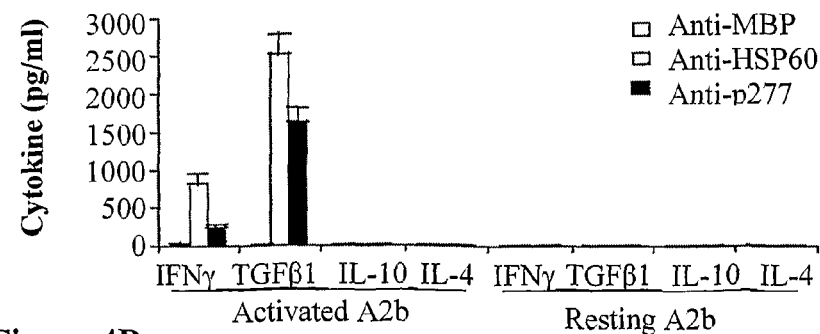

To investigate how the anti-ergotypic response to HSP60 might function, the inventors analyzed the cytokines produced by Anti-HSP60 and Anti-p277 T cells in response to either activated or resting A2b T cells. FIG. 4D shows that both the Anti-HSP60 and Anti-p277 T-cells secreted relatively small amounts of IFNγ and relatively high amounts of TGFβ1 upon stimulation with activated A2b T cells only. The T cells did not secrete IL-10 or IL-4.

Example 5

The Activation of HSP60-Specific Anti-Ergotypic T Cells Requires Co-Stimulation

Figure 5:
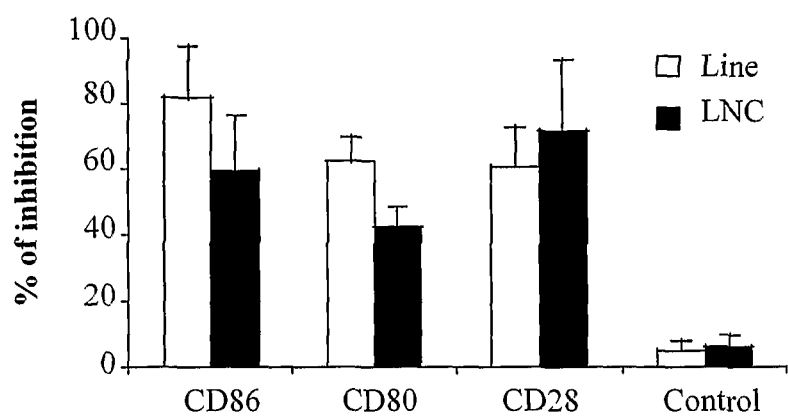
FIG. 5. The activation HSP60-specific anti-ergotypic T cells requires co-stimulation. Monoclonal antibodies to CD28, CD80 or CD86, or a control IgG (Control), were assayed for their ability to block the anti-ergotypic proliferative response of Anti-HSP60 T-cells (Line) or of LNC prepared from pHSP60-vaccinated rats (LNC). Results are presented as the percent of inhibition of proliferation±SEM of quadruplicate cultures. Three independent experiments produced similar results.

Complete T-cell activation is achieved when TCR-mediated signaling is reinforced by signals originating from co-stimulatory molecules such as CD28. CD28 interacts with CD80 and CD86 molecules displayed on the surface the APC. Activated T cells and activated A2b express CD80 and CD86 molecules on their surface. The inventors therefore studied the need for CD80, CD86 and CD28 in the activation of HSP60-specific T cells by activated T cells. LNC prepared from pHSP60 vaccinated rats, or Anti-HSP60 T cells, were stimulated with irradiated A2b T cells in the presence of blocking antibodies to CD80, CD86 or CD28. FIG. 5 shows that incubation with each one of these antibodies produced a significant inhibition in the anti-ergotypic response of HSP60-specific T cells. Hence, co-stimulation by way of CD80, CD86 and CD28 appears to be required for the activation of anti-ergotypic HSP60-specific T cells by activated T cells.

Example 6 p277-Specific Anti-Ergotypic T Cells Ameliorate AA

Figure 6A:
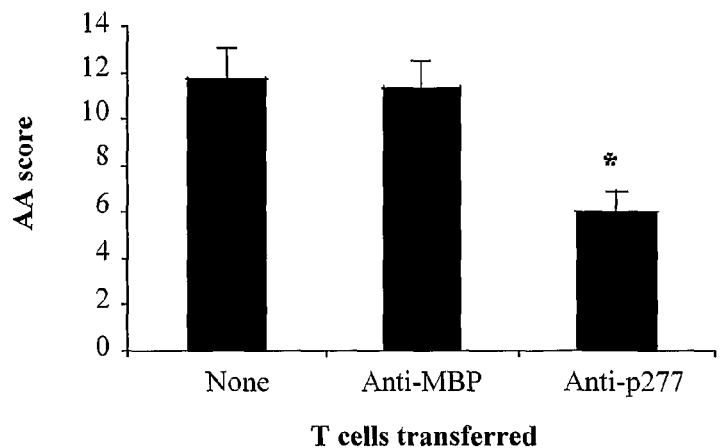
FIG. 6. p277-specific anti-ergotypic T-cells control arthritogenic T-cells in vivo. A and B. Anti-MBP or Anti-p277 T cells were injected ip into naïve Lewis rats and three days later AA was induced. Twenty-six days after AA induction, at the peak of AA, the AA clinical score (A) and the hind paw diameter (B) were determined. The bars represent the mean values±SEM for each group of 8 rats. C. LNC were collected on day 26 after AA induction and the secretion of IFNγ upon stimulation with Mt176-90 was studied. The results are presented as pg/ml±SEM of triplicate cultures. Three independent experiments produced similar results. * p<0.05 and ** p<0.005 compared to the Anti-MBP group.
Figure 6B:
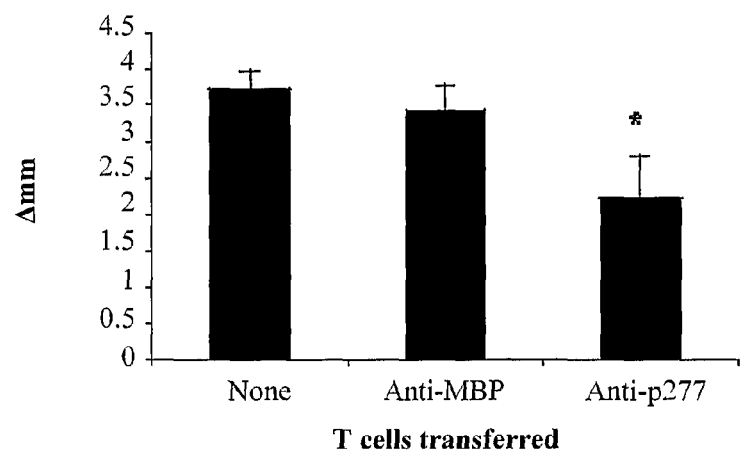

If HSP60-specific anti-ergotypic T cells are indeed regulatory, then it should be possible to inhibit inflammatory disease by adoptively transferring them. The inventors tested the effects of Anti-p277 T cells on AA by transferring $10^7$ cells to rats 3 days before the active induction of AA. As a control, the Anti-MBP T-cell line was used. The rats were scored for signs of arthritis, and the hind paw diameter was measured with a caliper on day 26, the peak of AA (Quintana et al., 2002b). FIG. 6 shows that the recipients of the Anti-p277 cells showed a significant reduction in the signs of AA, both in terms of arthritis score and of limb swelling. The Anti-MBP T cells had no effect on the progression of AA (FIG. 6).

Figure 6C:
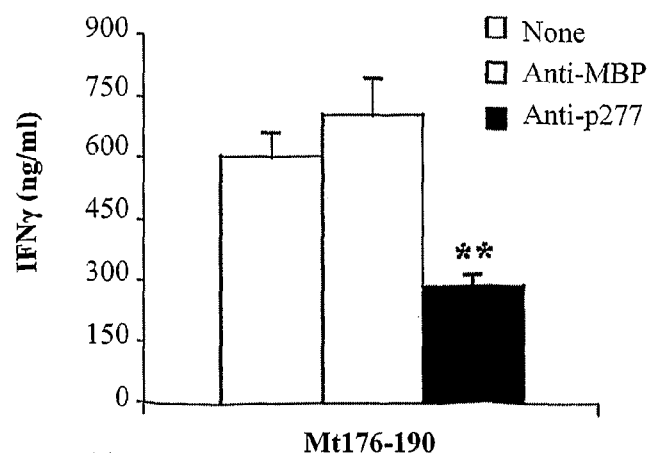

The arthritogenic T cells that drive AA have a Th1 phenotype. Accordingly, lymph node T cells from rats suffering from AA secrete high levels of IFNγ in response to in vitro stimulation with the Mt176-90 peptide (Quintana et al., 2002b), containing the pathogenic 180-88 T-cell epitope of the mycobacterial 65 kDa HSP (van Eden et al., 1988). The inhibition of AA achieved by vaccination with HSP60 or its peptides is reported to be associated with a reduction in INFγ production induced by Mt176-90 (Quintana et al., 2002b, Quintana et al., 2003). The inventors therefore isolated LNC from rats adoptively transferred with Anti-p277 or Anti-MBP T cells, and studied the secretion of IFNγ upon stimulation with Mt176-90. FIG. 6C shows that the transfer of Anti-p277 T cells led to a significant reduction in the secretion of IFNγ in response to the AA target peptide Mt176-190. Thus, HSP60-specific T cells, demonstrating anti-ergotype activity, down-regulate IFNγ secretion by the candidate pathogenic T cells at the time they adoptively down-regulate AA.

Example 7 p277-Specific Anti-Ergotypic T Cells Modulate Effector T-Cells In Vitro

Figure 7A:
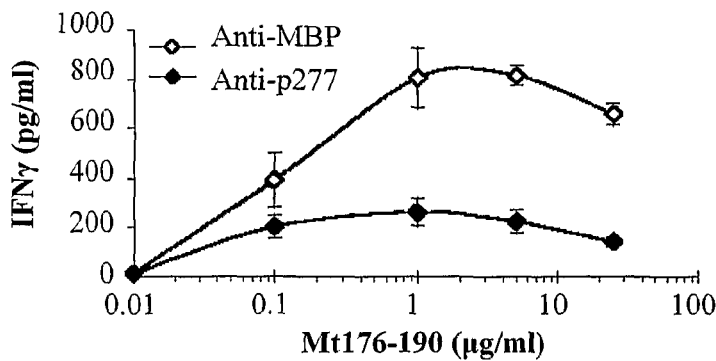
FIG. 7. HSP60-specific Anti-ergotypic T-cells control arthritogenic T-cells in vitro. A. LNC from Mt immunized rats ($2.5 \times 10^5$ per well) were activated with Mt176-90 for 72 hr in the presence of Anti-p277 or Anti-MBP T-cells ($5 \times 10^4$ per well). The secretion of IFNγ was determined by ELISA, the results are presented as pg/ml±SEM of triplicate cultures. The differences between the groups were significant (p<0.05) for antigen concentrations higher than 0.1 µg/ml. Three independent experiments produced similar results. B-D. anti MBP or anti-p277 lines were injected ip into naïve Lewis rats three days before the induction of AA. Twenty-six days later LNC were collected and the proliferative responses to PPD, HSP65, Mt176-90 (B); HSP60, p277 or Hu3 (C) or antiergotypic (D) were studied.
Figure 7B:
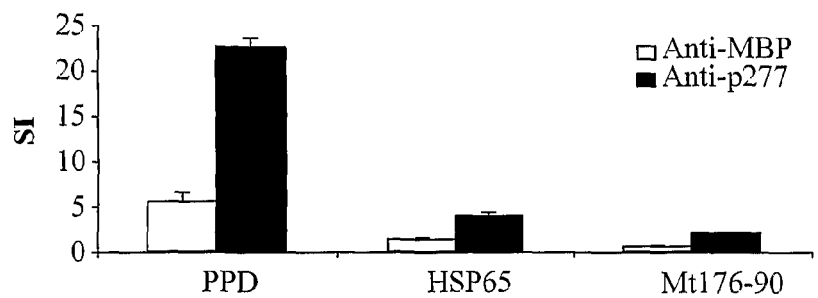
Figure 7C:
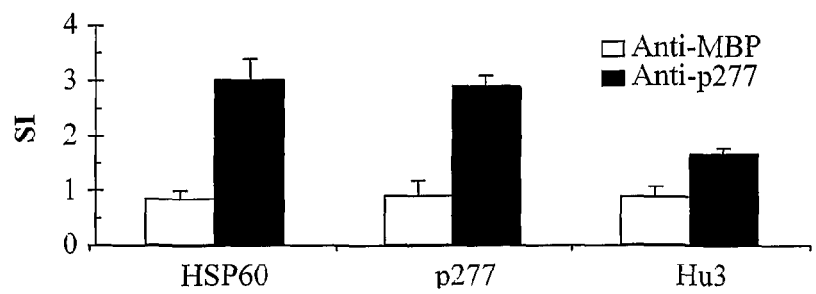
Figure 7D:
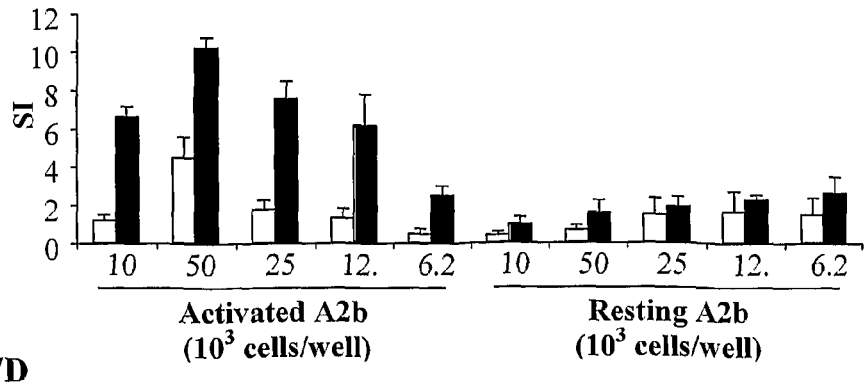

The results obtained in the AA model demonstrated that anti-ergotypic HSP60-specific T-cells can control effector T cells by adoptive transfer in vivo. To further investigate the effect of HSP60-specific anti-ergotypic T cells, the inventors tested whether these T cells might be able to directly regulate in vitro the IFNγ secretion of LNC taken from rats on day 26, at the peak of AA. LNC of rats with actively induced AA were prepared and activated with Mt176-90 in the presence of the Anti-p277 anti-ergotypic T-cell line, or in the presence of the control Anti-MBP T-cell line. T cells reactive with Mt176-90 have been shown to transfer AA to irradiated naïve Lewis rats. Co-incubation with the Anti-p277 line, but not with the Anti-MBP line, led to a significant decrease in the secretion of IFNγ (FIG. 7A). The inventors did not detect a concomitant induction of IL-10 (not shown). Thus, anti-ergotypic T cells can directly control in vitro the arthritogenic T-cell IFNγ cytokine response.

FIG. 7 further shows that the decrease in the clinical signs of AA was associated with an increased reactivity against Mt-derived antigens. $5 \times 10^6$ T cells of anti MBP or anti-p277 lines were injected ip into naïve Lewis rats three days before the induction of AA. Twenty-six days later LNC were collected and the proliferative responses to PPD, HSP65, Mt176-90 (B); HSP60, p277 or Hu3 (C) or antiergotypic (D) were studied. The results are expressed as the mean±SEM stimulation index of quadruplicate cultures. Three independent experiments produced similar results.

An increase in the T-cell response to HSP60 (FIG. 7C) and to activated A2b (anti-ergotypic response, FIG. 7D), could also detected. Thus, the decrease in the clinical signs of AA induced by the transfer of the anti-p277 specific T-cell line is associated with changes in the T-cell responses to Mt-derived antigens and to HSP60.

Example 8

Figure 8A:
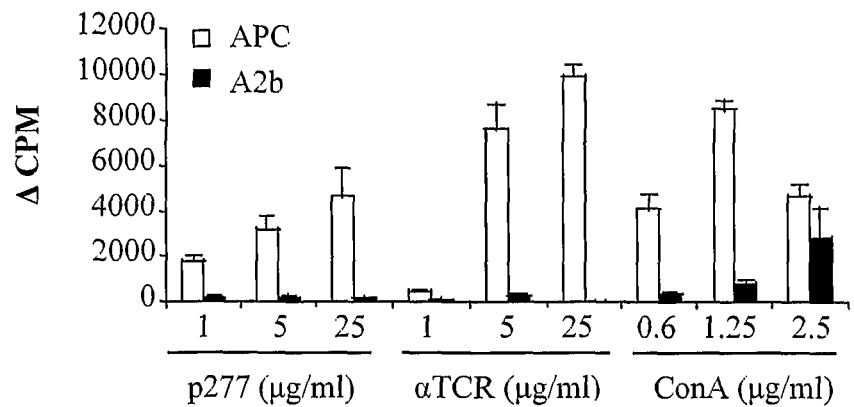
FIG. 8. Anti-ergotypic HSP60-specific T cells become anergic after interacting with activated T cells. Anti-ergotypic Anti-p277 T cells were stimulated for 3 days with irradiated, activated A2b cells (A2b) or with irradiated APC fed with the p277 peptide (APC). The Anti-p277 T cells were maintained for 4 additional days in culture, and stimulated with APC and p277 peptide, Con A or immobilized anti-TCR (αTCR) antibodies. T-cell proliferation (A) and IFNγ (B) release were measured after 3 days. The proliferative responses are presented as the ΔCPM (±SEM) (A), and the IFNγ as pg/ml±SEM (B) of triplicate cultures. Three to five independent experiments produced similar results.
Figure 8B:
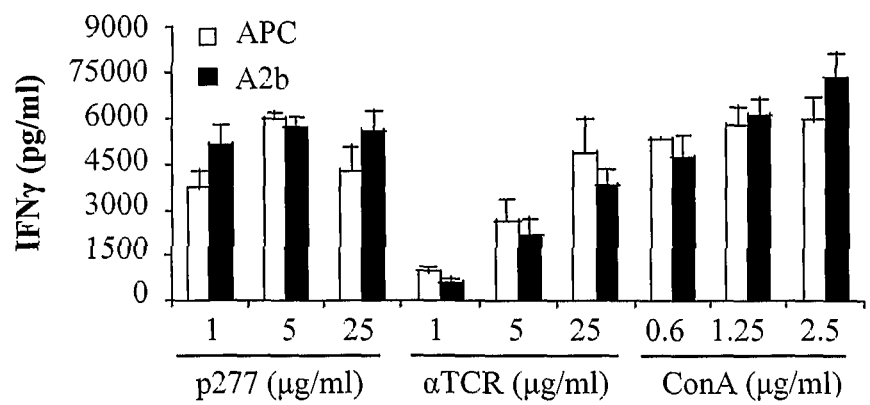

HSP60-Specific Regulators Become Anergic Following their Regulation of Activated T Cells The inventors have shown in the previous Examples that HSP60-specific anti ergotypic T cells can recognize and down-regulate arthritogenic T cells, in vitro and in vivo. However, any regulatory mechanism has to be regulated; uncontrolled down-regulation of immunity would be as detrimental to the organism as uncontrolled autoimmunity. The inventors therefore studied whether the stimulation of HSP60-specific anti-ergotypic T cells by activated T cells might itself affect the regulators. In other words, might the anti-ergotypic HSP60-specific T-cell lines be affected differently by seeing their HSP60 epitopes presented by activated T cells compared to recognizing HSP60 presented by classical APC? To study this possibility, the Anti-p277 line was incubated for 3 days with either irradiated APC and p277 peptide or with irradiated, activated A2b T cells. The Anti-p277 T cells were then recovered from the cultures, maintained for 4 additional days in culture without APC or A2b T cells, and then stimulated with APC and p277 peptide, with mitogenic Con A or immobilized anti-TCR. FIG. 8 presents the outcome. It can be seen that culturing the Anti-p277 line with activated A2b T cells rendered the Anti-p277 line anergic; the line now failed to proliferate in response to APC and p277 or to either of the two mitogens (FIG. 8A). FIG. 8B shows that the Anti-p277 T cells could still secrete IFNγ (but not TGFβ1, IL-10 or IL-4; not shown), despite their failure to proliferate. The Anti-p277 line cells, however, went on to die in vitro after their exposure to the activated A2b T cells. Thus, it appears that the interaction of anti-ergotypic T-cell lines with their target activated effector T cells leads to anergy and eventual loss of the anti-ergotypic T cells; activated effector T cells and regulator T cells can down-regulate each other. In contrast, as known in the art, anti-ergotypic T cells can be readily maintained in culture by APC and specific peptide antigen.

B. p277 Activates Cytokine-Associated Negative Regulator SOCS3 in T Cells

Reagents. The following reagents and chemicals were purchased as indicated: recombinant HSP60 (StressGen Biotechnologies; Victoria, BC, Canada); RPMI-1640 (Gibco BRL; Paisley, UK); FCS, antibiotics, sodium pyruvate (Biological Industries; Kibbutz Beit-Haemek, Israel); fibronectin (FN; Chemicon; Temecula, Calif.); SDF-1α, (R&D Systems; Minneapolis, Minn.), phosphatase inhibitor cocktail, PMB and PMB-agarose beads (Sigma-Aldrich; Rehovot, Israel); AG9 and AG490 (Calbiochem; San-Diego, Calif.), and $Na_2^{51}[Cr]O_4$ (Amersham Pharmacia Biotech; Little Chalfont, UK). Monoclonal antibodies (mAb): anti-human CXCR4 (clone 12G5; R&D Systems; MN); anti-SOCS3 (H-103; Santa-Cruz Biotech); anti-TLR2 and TLR4 (eBioscience; San-Diego, Calif.), and anti-human recombinant HSP60 (designated clone P5, IgM fraction; kindly provided by F. Quintana, The Weizmann Institute of Science). Antibodies anti-phosphorylated Pyk2 (clone py881) and anti-phosphorylated ERK½ (Biosource; Camarillo, Calif.); anti-total Pyk2 (clone N-19), anti-phosphorylated MLC (pMLC) and Ab anti-MLC (FL-172), anti-phosphorylated STAT3 (B7), and anti-total STAT3 (H-190) (Santa-Cruz Biotech; Santa-Cruz, Calif.); and anti-total ERK½ (Sigma); anti-phosphorylated AKT (pAKT) and anti-AKT (Cell Signaling Technology, Beverly Mass.). The recombinant HSP60 (StressGen Biotechnologies; Victoria, BC, Canada) used in this study contained less than 0.001 EU/ml (0.1 pg/ml) of bacterial endotoxin, as determined using a kinetic-turbidimetric LAL test method (Biological Industries, Kibutz Beit-Haemek, Israel). The peptides used in this study were prepared using standard FMOC chemistry as previously described (Raz et al., 2001). The sequence of p277 that was used in the following Examples 9-15 is VLGGGVALLRVIPALDSLTPANED (p277(Val$^6$Val$^{11}$), SEQ ID NO:2). The sequence of p30 is FNEETVSFWLRVP-KVSASHLE, residue 947-967 of Tetanus toxoid (SEQ ID NO:12).

Human cells. T cells were purified from the peripheral blood of healthy human donors (Blood Bank; Tel-Hashomer Hospital, Israel) as previously described (Zanin-Zhorov et al., 2003b). Whole blood was incubated (20 min, 22° C.) with RosetteSep™ human T-cell enrichment cocktail (StemCell Technologies, Vencouver, BC, Canada). After which, unsedimented cells were loaded onto Lymphocyte Separation Medium (ICN Biomedicals; Belgium), T cells were isolated by density centrifugation, and washed with PBS. Purified cells (>97% CD3$^+$ T cells) thus obtained were cultured in RPMI containing antibiotics and 10% heat-inactivated FCS. Human umbilical cord vein endothelial cells (HUVEC) were isolated from umbilical cord veins and cultured as described (Ponomaryov et al., 2000). Primary cultures were serially passaged, and passages 2 and 3 were taken for experiments.

Mice and mouse T cells. Female C57BL/6J were obtained from Harlan Olac (Bicester, U.K.). TLR2-knockout mice on the C57BL/6J background were kindly provided by Dr. S. Akira (Osaka University, Osaka, Japan). CD3$^+$ T cells were isolated by negative selection with anti-mouse antibody cocktail (Pan T cell kit; Miltenyi Biotec; CITY Germany). The labeled cells were then passed through separation columns (MidiMACS columns, Miltenyi Biotec). The purified cells (>97% T cells) were untreated or treated with HSP60 as described. Similarly, T cells were purified from the lymph nodes of BALB/c mice (females, 1.5 months of age).

T-cell migration assay. Migration of $^{51}$[Cr]-labeled human and mouse T cells through FN or endothelial cells to recombinant human SDF-1α was examined in 48-well Transwell chemotaxis apparatus (5-μm pore filters, 6.5-mm diameter; Corning, N.Y.), as previously described (Zanin-Zhorov et al., 2003b). For transendothelial migration assays, 2×10$^4$ cells of HUVEC were layered on the filters and grown in 10% FCS M199 for 2 days before the performance of each assay. Then, HUVEC were stimulated with TNF-α (50 ng/ml) for 24 hr and washed.

Western blotting of T-cell lysates. T cells were incubated (24 hr, 37° C.) in starvation medium (RPMI medium without serum). Aliquots (5×10$^6$/sample) of the starved cells were preincubated (for various intervals) with different concentrations of HSP60 prior to exposure to SDF-1α (100 ng/ml, 10 min, 37° C., tissue culture conditions). These reactions were terminated by freezing the plates (−70° C., 10 min). The plates were thawed, and the cells solubilized by incubating (60 min, 4° C.) in lysis buffer [EDTA (0.5 mM), NaCL (150 mM), NaF (10 nM), Tris pH 7.5 (25 mM), Triton X-100 (1%), PMSF (200 pg/ml), and phosphatase inhibitor cocktail (1%)]. Lysates were cleared by centrifugation (30 min, 14×10$^3$ rpm, 4° C.), and the resulting supernatants analyzed for protein content. Sample buffer was added, the samples were boiled, and equal amounts of proteins were separated by 10% SDS-PAGE and transferred to nitrocellulose membranes. The membranes were blocked with TBST buffer [Tris pH 7.5 (20 mM), NaCl (135 mM) and Tween 20 (0.1%)] containing low-fat milk (5%), and probed with the following mAb in the same buffer: anti-phosphorylated (p) ERK (0.2 μg/ml), anti-total (t) ERK (diluted 1:20,000), anti-pPyk2 (1.5 μg/ml), anti-tPyk2 (0.2 μg/ml), anti-pAKT (diluted 1:1000), anti-tAKT (diluted 1:1000), anti-pMLC (diluted 1:250), and anti-tMLC (diluted 1:1000), anti-pSTAT3 (diluted 1:250), and anti-STAT3 (diluted 1:500). Immunoreactive protein bands were visualized using a horseradish peroxidase-conjugated goat anti-mouse Ab and the enhanced ECL system. Phosphorylation levels of the 3-5 independent experiments were estimated by densitometry, and an average percentage of phosphorylation±SD was calculated as OD of pERK/tERK, or pPyk2/tPyk2, or pAKT/tAKT, pMLC/tMLC, or pSTAT3/tSTAT3×100%.

Cell morphology. T cells (3×10$^6$ cells/ml) were seeded in flat-bottom, 24-well plates in 500 μl of RPMI on coverslips coated with FN (25 μg/ml). Some T cells were pretreated (1 hr, 37° C., in a 7.5% CO$_2$ humidified atmosphere) with anti-TLRs mAb (20 μg/ml), and then with HSP60 (1 hr). After which, SDF-1α (200 ng/ml) was added, and the cells allowed to adhere (30 min, 37° C., in a 7.5% CO$_2$ humidified atmosphere). The cells were then fixed in 3.7% paraformaldehyde and permeabilized (5 min, room temperature) with 0.5% TritonX-100. For actin visualization, cells were stained with rhodamine-labeled phalloidin (diluted 1/100), and examined with a laser-scanning confocal microscope (LSM510, Zeiss).

In vivo homing assay. Purified human T cells were incubated (1 hr, tissue culture conditions) with HSP60 (1 μg/ml) in tissue culture conditions. The cells were then washed with PBS, and, where indicated, further incubated (30 min, 4° C.) with mouse anti-human CXCR4 mAb (10 μg/3×10$^6$ cells), anti-human TLR2 or anti-TLR4 mAb (each at 20 μg/ml). The cells were then washed and injected (5×10$^6$ cells/0.5 ml per mouse) i.v. into the tails of irradiated (375 cGY from a $^{60}$[Co] source), 8-week-old NOD/SCID mice, and the entrance of human T cells into the bone marrow of recipient mice was evaluated as previously described (Kollet et al., 2001). Each tested sample contained 1.5×10$^6$ cells.

DTH assays. BALB/c mice (females; 1.5 months of age) were sensitized by painting of their shaved abdominal walls with Oxazolone (2%) emulsified in 100 µl of acetone/olive oil (Sigma-Aldrich). On day 5, mice were sacrificed, their draining (inguinal, mesenteric, and cervical) lymph nodes were collected, and a single cell suspension was prepared. The cells were treated with HSP60 (1 µg/ml; 1 hr; tissue culture conditions), washed, and injected ($5 \times 10^7$ cells per mouse) i.v. into the tails of naive mice (at least 6 mice per group). Painting of the earlobes with oxazolone (10 µl of 0.5% in acetone/olive oil), which generates a DTH response, was performed immediately after cell inoculation. The area of the ears that was painted was measured before challenge and 24 hr later with a micrometer. Changes in earlobe thickness are indicative of DTH reactivity. All animal studies were performed in compliance with and were approved by laws and animal welfare guidelines of The Weizmann Institute of Science (IACUC).

RNA interference. The inventors synthesized a silent RNA (siRNA) sequence targeting SOCS3 position 80-101 relative to the start codon: 5'-AAGAGCGAGTACCAGCTGGTG-3' (SEQ ID NO:13); a double-stranded RNA targeting luciferase (GL-2) was used as control (Dharmacon Research). Transfections of freshly purified T cells were performed using the Human T cell Nucleofector™ kit (Amaxa Biosystems, Cologne, Germany). In brief, $5 \times 10^6$ CD3$^+$ T cell were resuspended in 100 µl of Human T Cell Nucleofector solution, mixed with a total of 3 µg of siRNA duplex, and pulsed using the Nucleofector program U-14. Transfected cells were cultured in RPMI containing 10% heat-inactivated FCS and 10 ng/ml of IL-2. Cell migration was evaluated as described 48 h after transfection. Transfection efficiency was controlled by evaluating SOCS3 levels by Western Blotting.

Example 9

Figure 9A:
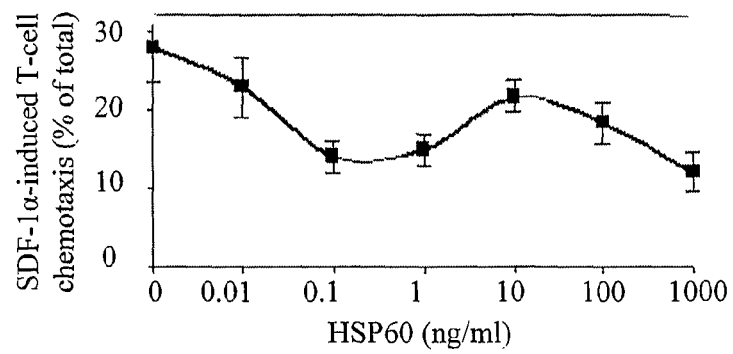
FIG. 9. HSP60 inhibits SDF-1α-induced chemotaxis through fibronectin (A) and endothelial cells (B) of human T cells, and homing of such cells into the bone marrows of NOD/SCID mice in a TLR2-dependent manner (C and D). A. and B. Human T cells were incubated with indicated concentrations of HSP60 for 1 hr (A), or with 1 ng/ml of HSP60 for 1 hr (B), radioactively labeled, and T-cell migration assays through FN-coated (A), or through TNF-α-activated HUVEC monolayer (B) were performed (3 hr, 37° C.) in Transwell apparati in the presence or absence of SDF-1α (100 ng/ml). Results are expressed as the percent of T-cells migrating towards SDF-1α. The average values±SD of five experiments are depicted. C and D. Human T cells, some of which were pretreated with mouse anti-human CXCR4, TLR2, or anti-TLR4 mAb, were treated with HSP60 (1 µg/ml, 1 hr) and injected into naïve NOD/SCID mice. T-cell homing to the bone marrows of mice was evaluated 16 hr later by flow cytometry. The results are expressed as the number (see right hand corner of the panels) of homing human cells per $10^6$ acquired cells (C), and percent of control (D). Combined data from five experiments is depicted. *P<0.05.
Figure 9B:
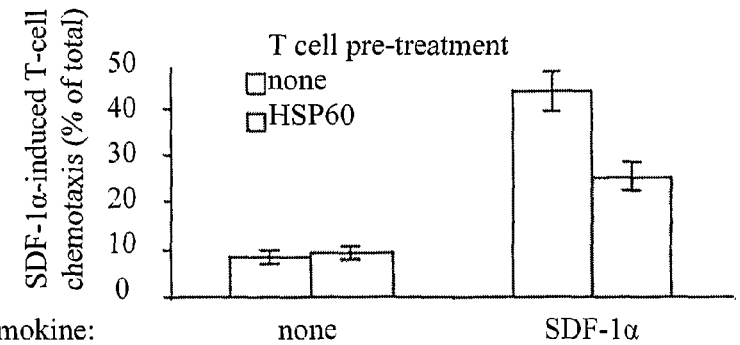

Exposure of T Cells to HSP60 for 1 hr Inhibits SDF-1α-Induced Chemotaxis Through Fibronectin and Endothelial Cells Purified human T cells were incubated with various concentrations of HSP60 for 1 hour and assayed the effect on chemotaxis. The inventors observed a significant inhibition of T-cell chemotaxis toward SDF-1α both through fibronectin (FIG. 9A) and through TNF-α-activated endothelial cells (FIG. 9B). These findings suggested that HSP60 might decrease the migration of T cells towards SDF-1α in vivo.

Example 10

HSP60 Decreases SDF-1α-Mediated Homing of Human T Cells to the Bone Marrow of NOD/SCID Mice Migration of T human cells in NOD/SCID mice is regulated primarily by interactions of SDF-1α with CXCR4; following exposure to sub-lethal doses of irradiation, the bone marrow of these mice express high levels of SDF-1α (Kollet et al., 2001). Therefore, the inventors examined the homing of HSP60-treated human T cells into the bone marrow of irradiated NOD/SCID mice. T cells were pretreated with HSP60 (1 µg/ml for 1 hr) and/or anti-CXCR4, anti-TLR2, or anti-TLR4 mAb, and then the T cells were injected into irradiated NOD/SCID mice. After 16 hr, homing of the T cells to the bone marrow of the mice was determined by assessing the expression of human CD45 and CXCR4 on bone marrow cells.

Figure 9C:
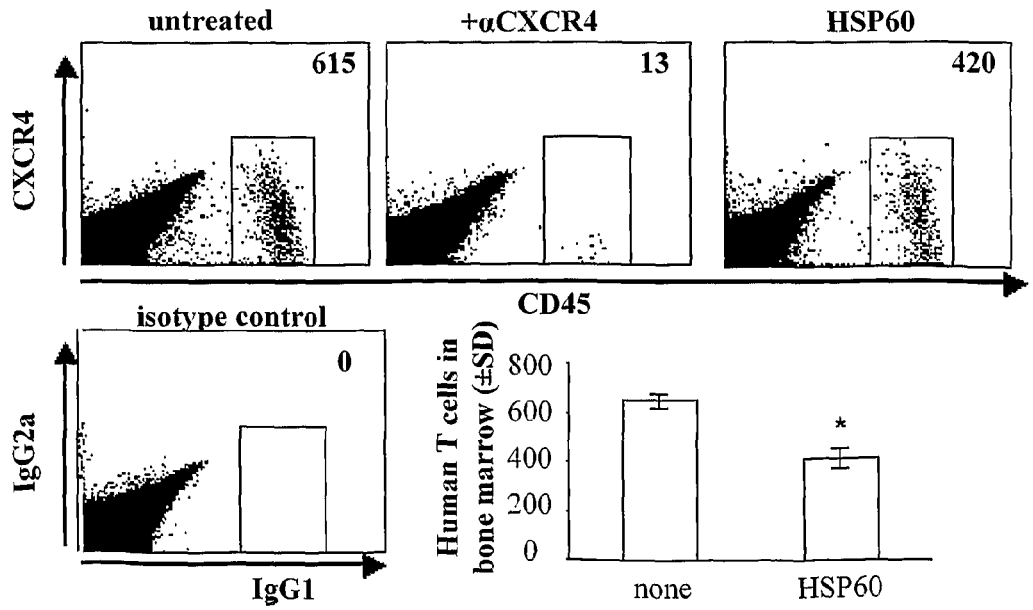
Figure 9D:
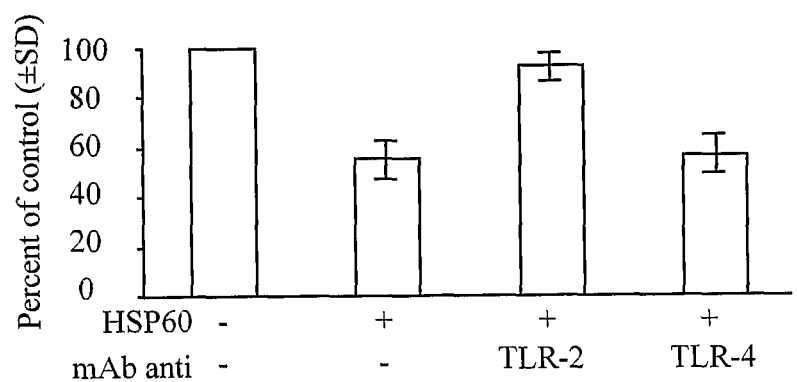

T-cell homing into mouse bone marrow was significantly abrogated by pre-treatment with anti-CXCR4 mAb (FIG. 9C); this indicates that CXCR4-SDF-1α interactions are indeed involved in the navigation of human T cells into this organ in vivo. Exposure of T cells to HSP60 for 1 hr significantly ($P<0.05$) decreased their homing to the bone marrow (FIG. 9C). Pre-treatment of human T cells with neutralizing anti-TLR2 mAb, but not anti-TLR4 mAb (both are mouse IgG2a antibodies), abrogated the inhibitory effect of HSP60 on T-cell homing into recipient bone marrow (FIG. 9D). Thus, the down-regulation of SDF-1α-induced human T-cell chemotaxis and homing by HSP60 requires functional TLR2.

Example 11

HSP60 Inhibits SDF-1α-Induced Mouse T-Cell Chemotaxis In Vitro and DTH In Vivo

Figure 10A:
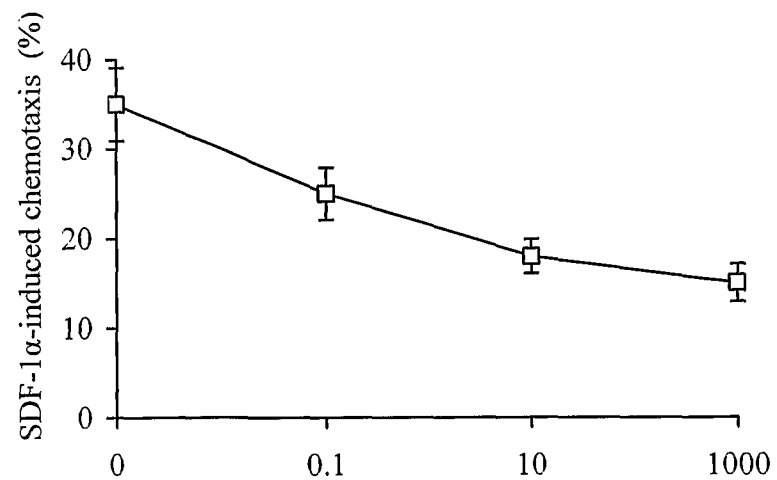
FIG. 10. HSP60 inhibits SDF-1α-induced mouse T-cell chemotaxis in vitro and DTH in vivo. A. Lymph node cells of BALB/c mice pre-sensitized to oxazolone were incubated in vitro with HSP60 (1 hr), washed, and their SDF-1α-mediated chemotaxis was determined. B. HSP60-treated mouse lymph node cells from oxazolone-sensitized mice were injected i.v. into naïve recipients whose earlobes were then painted with oxazolone. DTH reactivity (ear swelling, $10^{-2}$ mm±SD) was measured 24 hr later. DTH index: 1–[(treated cells mice–control cells)]×100. * P<0.05. One experiment representative of 3 is depicted.
Figure 10B:
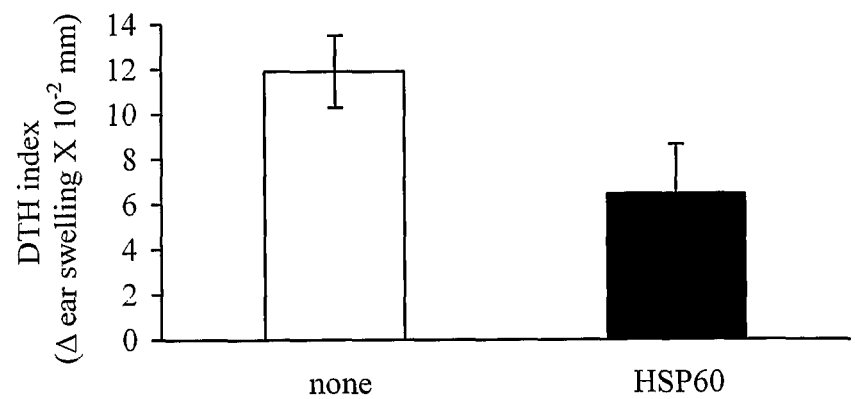
Figure 11A:
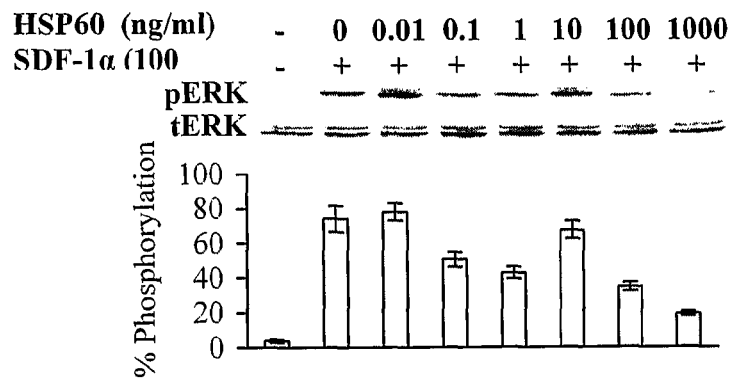
FIG. 11. HSP60 inhibits SDF-1α-induced ERK (A-C), Pyk2 (D, E), and AKT phosphorylation (F).
Figure 11B:
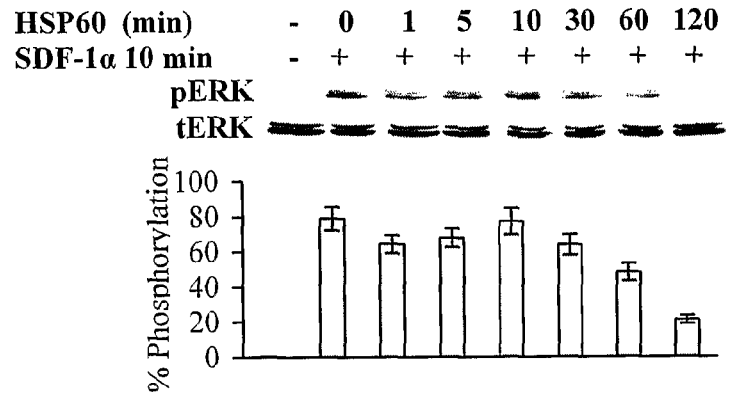
Figure 11C:
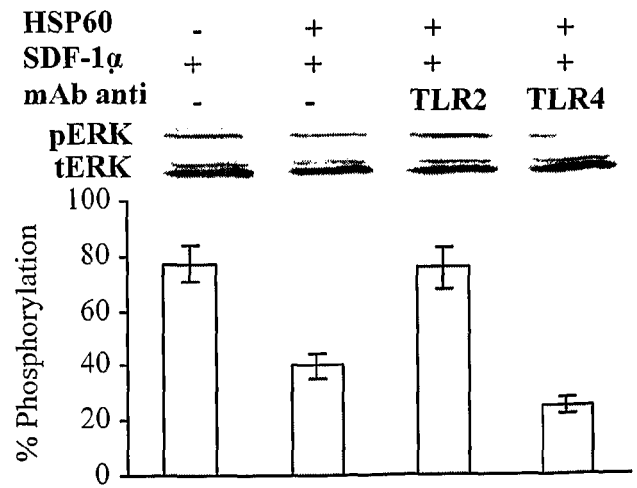
Figure 11D:
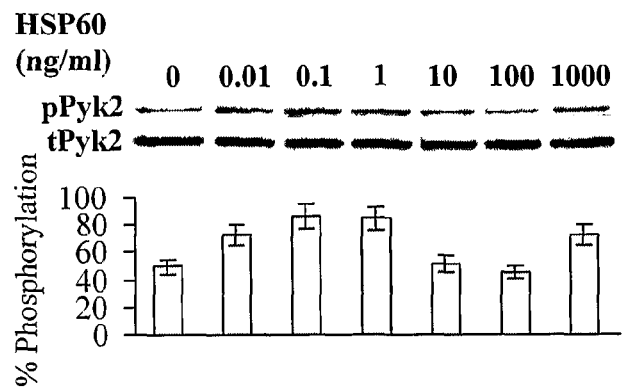
Figure 11E:
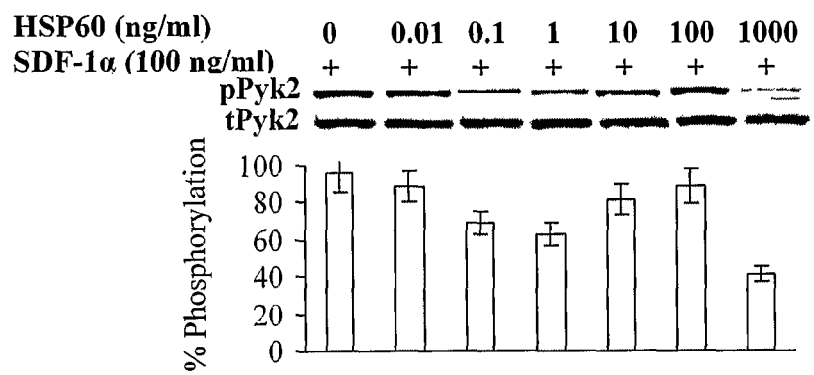
Figure 11F:
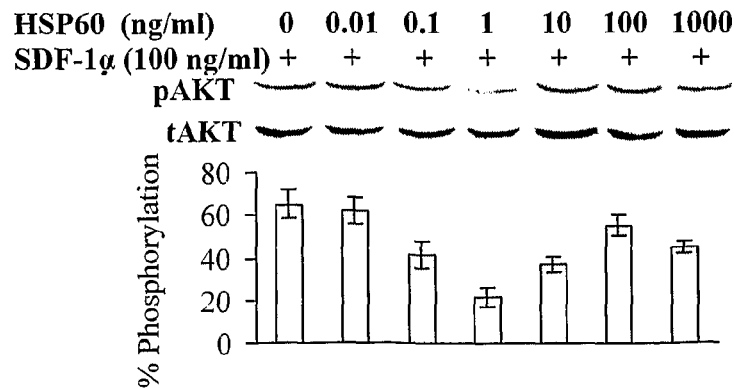

Recently, SDF-1α was shown to be involved in the recruitment of antigen-specific CD4$^+$ T cells to sites of DTH reactions in mice. Therefore, the inventors examined whether HSP60 can inhibit chemotaxis of mouse T cells in vitro and a T cell-dependent DTH response in vivo. The effect of human HSP60 on SDF-1α-mediated chemotaxis of BALB/c lymph node-cells in vitro was similar to that on human T cells: HSP60 inhibited migration of mouse lymph node cells towards SDF-1α (FIG. 10A). The inventors also studied the effect of human HSP60 on DTH in mice. Exposure in vitro of oxazolone-reactive mouse lymph node cells to HSP60 (1 µg/ml for 1 hr) inhibited by 50% their ability to adoptively transfer DTH in vivo (FIG. 10B). Thus, HSP60, which inhibits SDF-1α-induced T-cell chemotaxis, appears capable of down-regulating T-cell homing to and function at inflammatory sites in vivo.

Example 12

HSP60 Effects on T Cell Signal Transduction

As can be seen in FIG. 11, HSP60 inhibits SDF-1α-induced ERK (A-C), Pyk2 (D, E), and AKT phosphorylation (F). Human T cells were exposed to HSP60 for 1 hr (A, C-F) or to 1 ng of HSP60/ml for 0-120 min (B), washed and then treated with SDF-1α (100 ng/ml, 10 min) (A-C, E, F) or not (D). Lysates of these cells were immunoblotted with antibodies: anti-phospho-ERK (pERK) and anti-total ERK (tERK) (A-C), anti-pPyk2 and anti-tPyk2 (D, E) or with anti-pAKT and anti-tAKT (F). C. T cells pretreated with mAb anti-TLR2 or anti-TLR4 mAb (20 µg/ml, 30 min) were then incubated with HSP60 (1 ng/ml, 1 hr), and washed followed by SDF-1α (100 ng/ml, 10 min). The blot of 1 experiment representative of three (A, B) or five (C-F) is presented. Phosphorylation levels of the experiments were estimated by densitometry, and an average percentage of phosphorylation±SD was calculated as OD of pERK/tERK, or pPyk2/tPyk2, or pAKT/tAKT×100%.

Figure 12A:
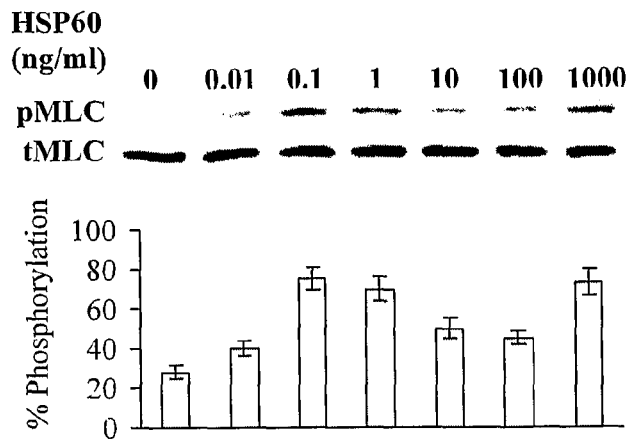
FIG. 12. HSP60 induces phosphorylation of MLC (A), inhibits SDF-1α-induced phosphorylation of MLC (B) and polarized morphology (C) in T cells.
Figure 12B:
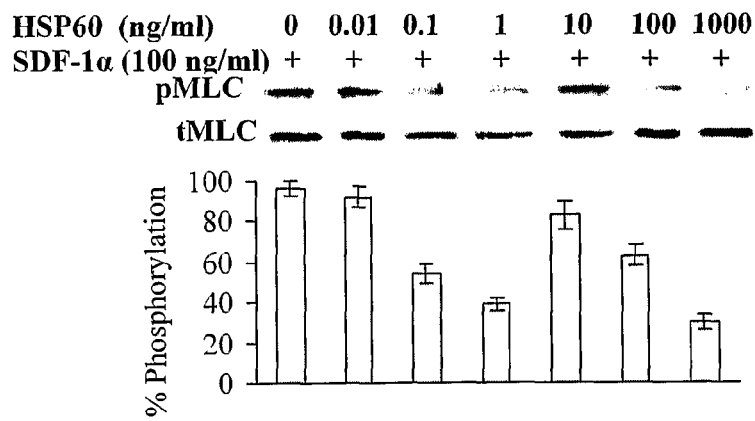
Figure 12C:
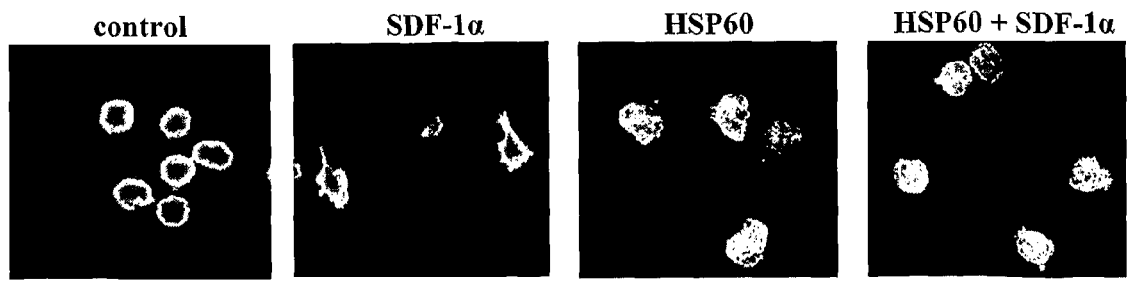

As can be seen in FIG. 12, HSP60 induces phosphorylation of MLC (A), inhibits SDF-1α-induced phosphorylation of MLC (B) and polarized morphology (C) in T cells. Human T cells were treated with HSP60 (1 hr; A) followed by SDF-1α (100 ng/ml, 10 min; B). Cell lysates were immunoblotted with anti-pMLC and anti-tMLC Ab. Phosphorylation levels of the five experiments were estimated by densitometry, and an average percentage of phosphorylation was calculated as the OD of pMLC/tMLC×100%. C. T cells were plated onto FN-coated coverslips in the absence or presence of HSP60 (1 µg/ml). After 1 hr, some of the cells were exposed to SDF-1α

(100 ng/ml). Immunofluorescent staining for actin in one experiment representative of 4 is shown.

Thus, inhibition by HSP60 of SDF-1α-induced intracellular phosphorylation of signaling elements involved in T-cell activation and chemotaxis is accompanied by an inhibition of the morphological changes required for T-cell adhesion and migration Example 13

HSP60 Inhibits SDF-1α-Induced Activation and Migration of T Cells by Up-Regulation of SOCS3

Figure 13A:
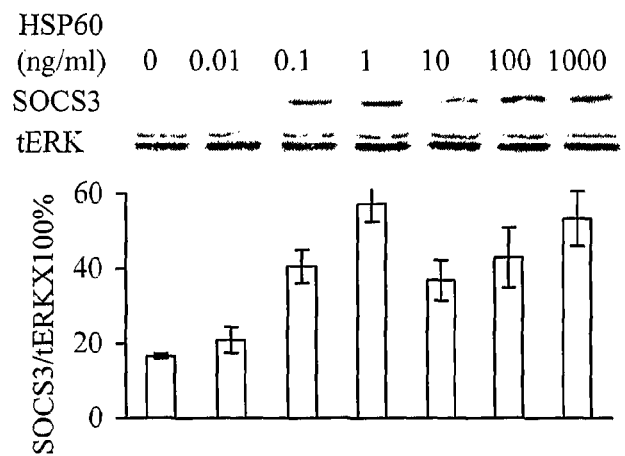
FIG. 13. Activation by HSP60 of SOCS3 expression in T cells via TLR2 signaling and STAT3 activation mediates the down-regulation of SDF-1α-induced chemotaxis. Human T cells (A, D, F, G, H), mouse lymph node lymphocytes (B) or mouse purified T cells (E) were incubated with HSP60 at 0.01-1000 ng/ml for 1 hr, or at 1 ng/ml for 0-120 min (C). Some cells were pre-treated with anti-TLR2 or anti-TLR4 mAb (D), the JAK/STAT inhibitor AG490 or control inhibitor AG9 (18 hr; F). E. Purified T cells from wild type C57BL/6J and TLR2-knockout mice incubated with HSP60 1 ng/ml for 1 hr. H and I, T cells were transfected with siRNA targeting SOCS3, or with control siRNA, and exposed to HSP60 (2 hr). Cell lysates were immunoblotted with anti-SOCS3 and anti-total ERK [tERK; evaluation of total tERK served as a control (A-F, H)], or with anti-pSTAT3 and anti-STAT3 (G). The levels of SOCS3, tERK, pSTAT3, and tSTAT3 were estimated by densitometry and the average percentage (±SD) of the three experiments was calculated by OD of SOCS3/tERK (pSTAT3/tSTAT3)×100. H, cells were $^{51}$[Cr]-labeled, washed, and their ability to migrate in response to SDF-1α was examined. Averages±SD of three different experiments are shown.
Figure 13B:
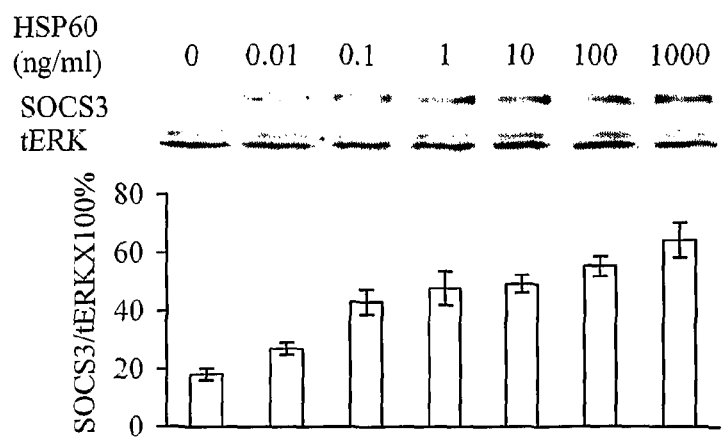

SOCS family proteins have been identified as negative feedback regulators of cytokine-induced JAK/STAT activation, through their binding to JAK kinases. Chemokine activation too, has been shown to be regulated by SOCS proteins; up-regulation of SOCS3 inhibited CXCR4 signaling and blocked chemotaxis to SDF-1α. Since T-cell responses to SDF-1α are also attenuated by HSP60, the inventors tested whether HSP60 too might induce SOCS3 activation. T cells were incubated (1 hr) with HSP60 (0-1000 ng/ml) and intracellular activation of SOCS3 and tERK, which is constitutively expressed, were determined by Western blotting. FIG. 13A shows that HSP60 activated the expression of SOCS3 ($P<0.05$). The effects of human HSP60 are not restricted to human T cells: HSP60 also induced the expression of SOCS3 in BALB/c lymph node cells (FIG. 13B). These effects were also dose-dependent, like the HSP60-induced expression of SOCS3 in human T cells (FIG. 13A). This effect of HSP60 on SOCS3 expression in BALB/c lymphocytes also explains the suppression of mouse T-cell chemotaxis to SDF-1α noted above in vitro (FIG. 10A) and in vivo (induction of DTH; FIG. 10B).

Figure 13C:
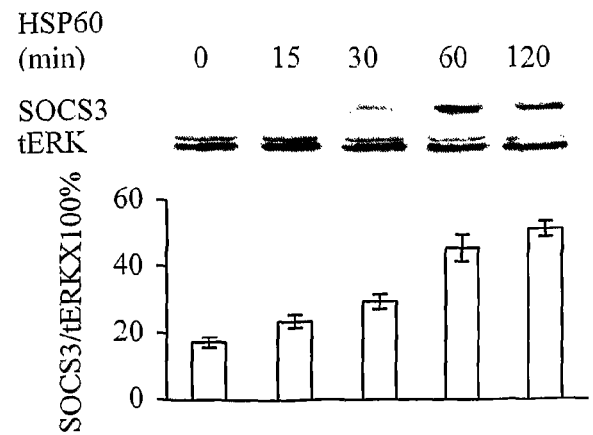

The dose-response curve of the activation of SOCS3 in human T cells was biphasic, displaying maximal activities at HSP60 concentrations of 1 ng/ml and 1 μg/ml. With 1 ng/ml of HSP60, activation was already apparent after 30 min and peaked at 1 to 2 hr (FIG. 13C).

Figure 13D:
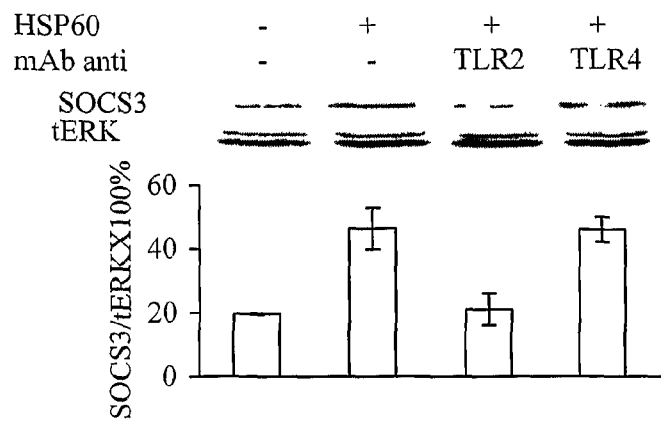
Figure 13E:
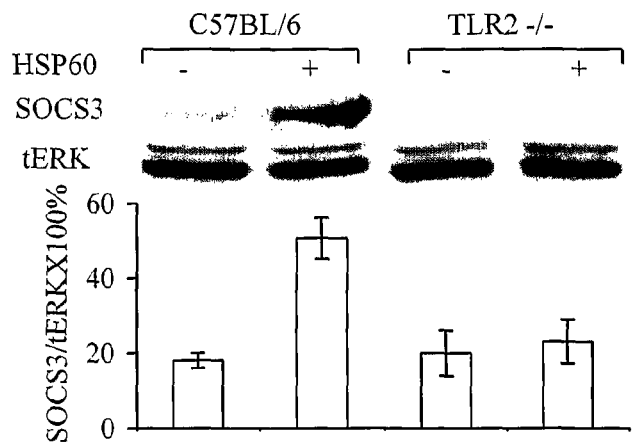

To test whether TLR2 or TLR4 might be functionally involved in the activation of SOCS3 by HSP60, the inventors assayed the effect of pre-incubating T cells with blocking antibodies to the TLR molecules. FIG. 13D shows that this activation of SOCS3 was TLR2-dependent, since anti-TLR2 abrogated the activation by HSP60. Moreover, the involvement of TLR2 was confirmed by using T cells purified from TLR2-knockout and wild type C57BL/6J mice. FIG. 13E shows that, as expected, treatment of wild type C57BL/6J-derived T cells with HSP60 (1 ng/ml, 1 hr) induced SOCS3 expression at levels similar to those induced by HSP60 in human T cells. In contrast, SOCS3 expression remained at the low levels of untreated cells when T cells from TLR2-knockout mice were treated with HSP60. Thus, HSP60 induces SOCS3 expression in T cells via signaling through TLR2.

Figure 13F:
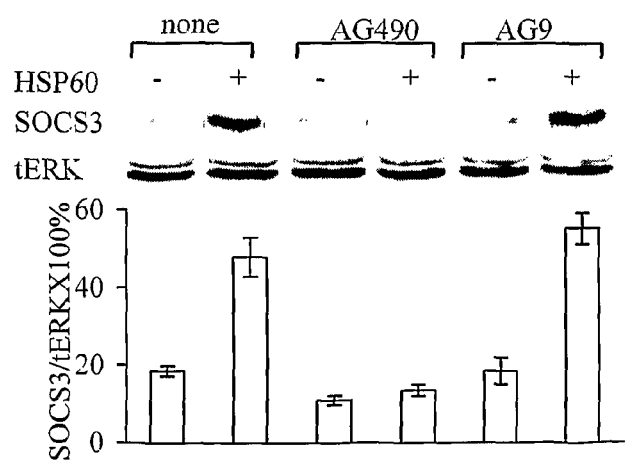
Figure 13G:
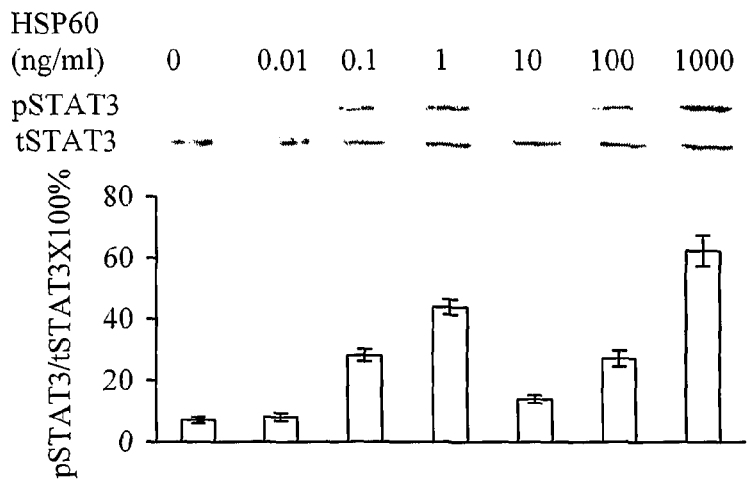

Up-regulation of SOCS3 expression requires prior activation of the JAK7STAT pathway. Therefore, the inventors tested the effect of a specific blocker of JAK/STAT activation, AG490, on HSP60-induced up-regulation of SOCS3 in human T cells. Pretreatment (18 hr) of T cells with AG490 (10 nM), but not with its control counterpart AG9, abrogated the effect of HSP60 on SOCS3 expression (FIG. 13F), whereas pertussis toxin, a $G_{\alpha i}$ protein inhibitor, had no effect (not shown). Furthermore, HSP60 induced phosphorylation of STAT3 (FIG. 13G), which is essential for SOCS3 up-regulation (Alexander et al., 1999, Starr et al., 1997). The dose-response curve of induction of STAT3 phosphorylation (FIG. 13G) was very similar to that of activation of SOCS3 by HSP60 (FIG. 13A). Thus, HSP60 induced SOCS3 expression through activation of intracellular signaling involving up-regulation of STAT3 phosphorylation.

Example 14

Figure 13H:
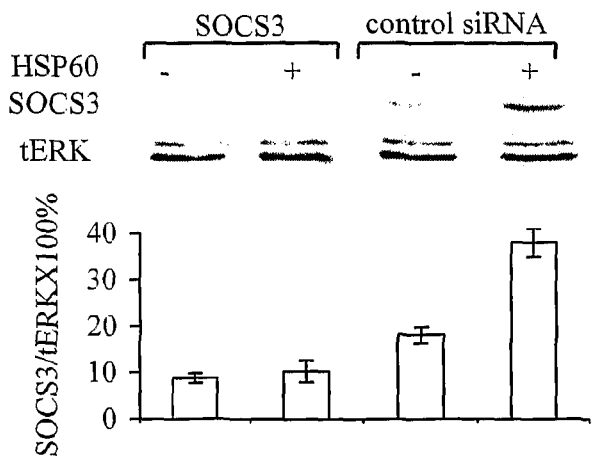
Figure 13I:
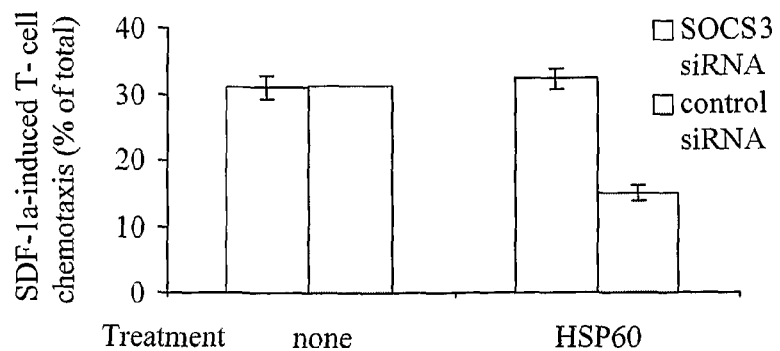

Inhibition of SDF-1α-Induced T-Cell Chemotaxis by HSP60 is Prevented by Silencing SOCS3 Gene Expression To confirm the conclusion that the inhibitory effect of HSP60 on SDF-1α-induced T-cell chemotaxis is mediated through SOCS3 up-regulation, SOCS3 gene expression was specifically silenced using RNA interference. This treatment abrogated the induction of SOCS3 expression by HSP60; transfection with control siRNA had no effect (FIG. 13H). Moreover, the inhibitory effect of HSP60 on SDF-1α-induced T-cell chemotaxis was completely prevented by specifically silencing the SOCS3 gene (FIG. 13I).

Example 15

Effects of HSP60 on SOCS3 Expression are not Due to Contamination with LPS, and are Retained with p277

The LPS-TLR2 interaction results in intracellular signals, and several batches of recombinant human HSP were shown to contain minimal residual LPS and LPS-lipoproteins, which are biologically active on macrophages. Using a kinetic-turbidimetric test method, the inventors found that the recombinant human HSP60 used in this study contained less than 0.001 EU/μg protein (0.1 pg/μg) of bacterial endotoxin.

Figure 14A:
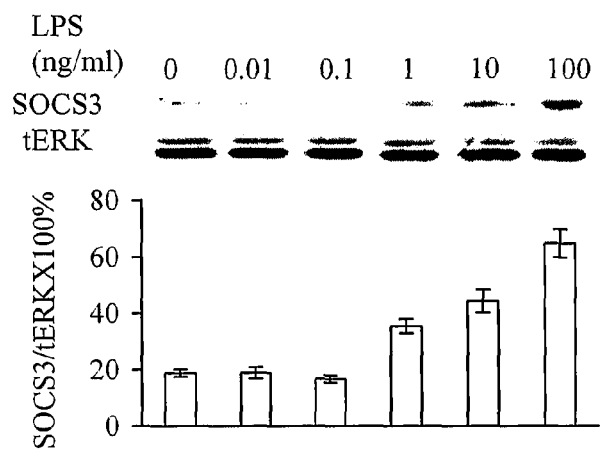
FIG. 14. Effects of HSP60 on SOCS3 expression are not due to contamination with LPS. Human T cells were treated (1 hr; 37° C.) with LPS (different concentrations in A, 100 ng/ml in C), HSP60 (1 ng/ml, B), LPS or HSP60 (D), or p30 or p277 (E). SOCS3 activation in the T-cell lysates was measured by immunoblotting. B, T cells were pretreated (30 min) with anti-HSP60 mAb (20 µg/ml), isotype matched mAb (IgM), or PMB (1 pg/ml). Alternatively, HSP60 or LPS were boiled (100° C., 30 min) before their addition to the T-cell cultures. D. LPS and HSP60 were pre-incubated with PMB-conjugated agarose beads, the unbound material was collected, checked for protein amount, and used to pre-treat the cells. One experiment representative of five (A-C), or three (D, E) is shown.

The following studies were performed to exclude the possibility that such a minute amount of LPS could affect SOCS3 activation in T cells. First the inventors examined whether LPS alone can affect SOCS3 expression by exposing T cells to increasing concentrations of LPS. LPS up-regulates SOCS3 expression in human T cells, but only at concentrations of 10-100 ng/ml (FIG. 14A), which is 100-1000 fold higher than the amount of LPS in the HSP60 preparation used. Similarly, the inventors previously found that 1000 fold greater concentrations of LPS were needed to induce T-cell adhesion to fibronectin, an effect which was still less than that induced by human HSP60 (Zanin-Zhorov et al., 2003).

Figure 14B:
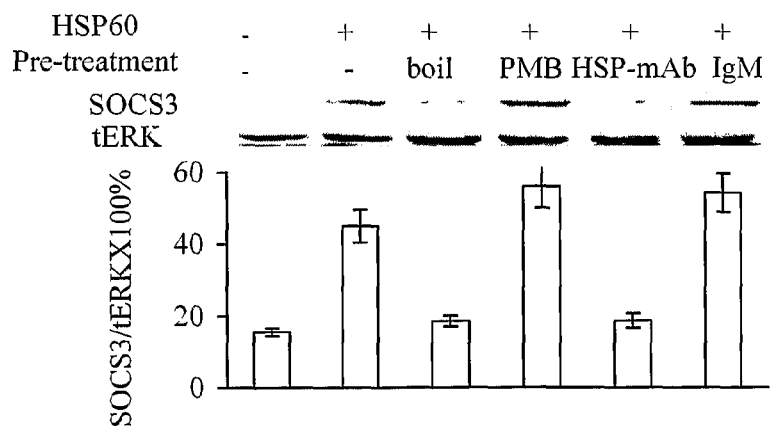
Figure 14C:
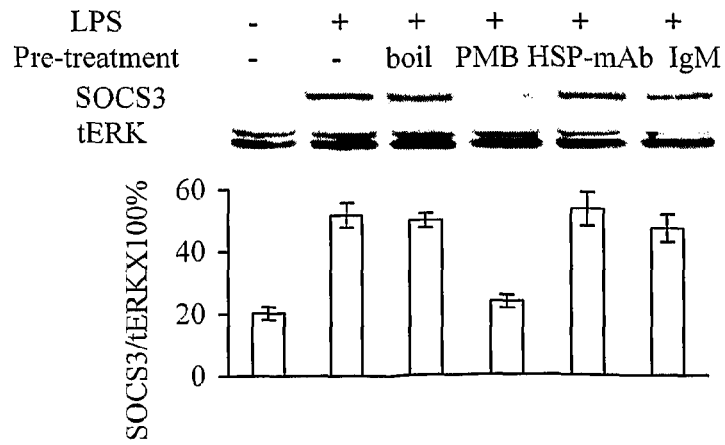

The exclusion of LPS in activation of SOCS3 by HSP60 was further confirmed by using anti-HSP60 mAb, by boiling (which denatures HSP60, but not LPS), and by using an LPS inhibitor, polymyxin B (PMB). The results, shown in FIG. 14, B and C, demonstrate that activation of SOCS3 by HSP60 (0.1 ng/ml; upper panel) was inhibited by boiling, but not by PMB (FIG. 14B), whereas activation of SOCS3 by LPS (100 ng/ml; lower panel) was inhibited by PMB, but not by boiling (FIG. 14C). Furthermore, anti-human HSP60 mAb inhibited the activation of SOCS3 by HSP60, but not the activation induced by LPS.

Figure 14D:
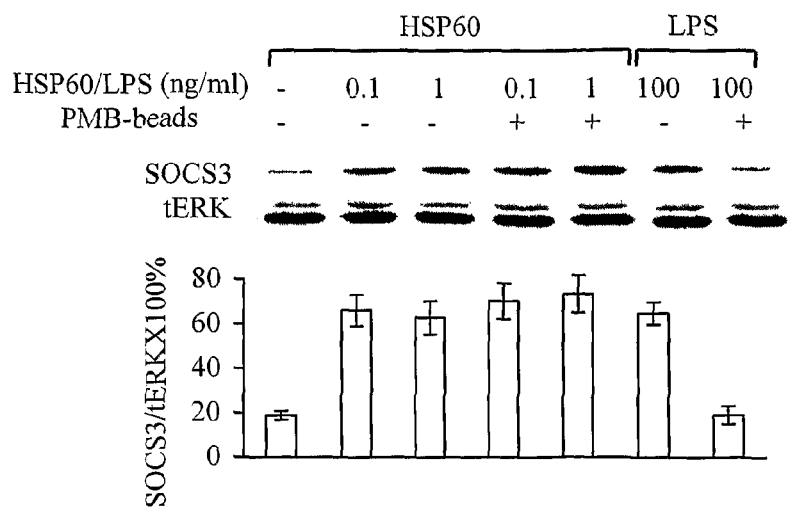

Recently, lipoproteins extracted from the LPS of *Escherichia coli* were shown to activate macrophages via TLR-2. These lipoproteins can be removed from LPS by passage through PMB-coupled agarose beads. Pre-incubation with PMB-conjugated agarose beads did not block the efficacy of our HSP60 preparation in inducing SOCS3 expression by T cells. In contrast, the efficacy of the LPS preparation was abolished (FIG. 14D).

Figure 14E:
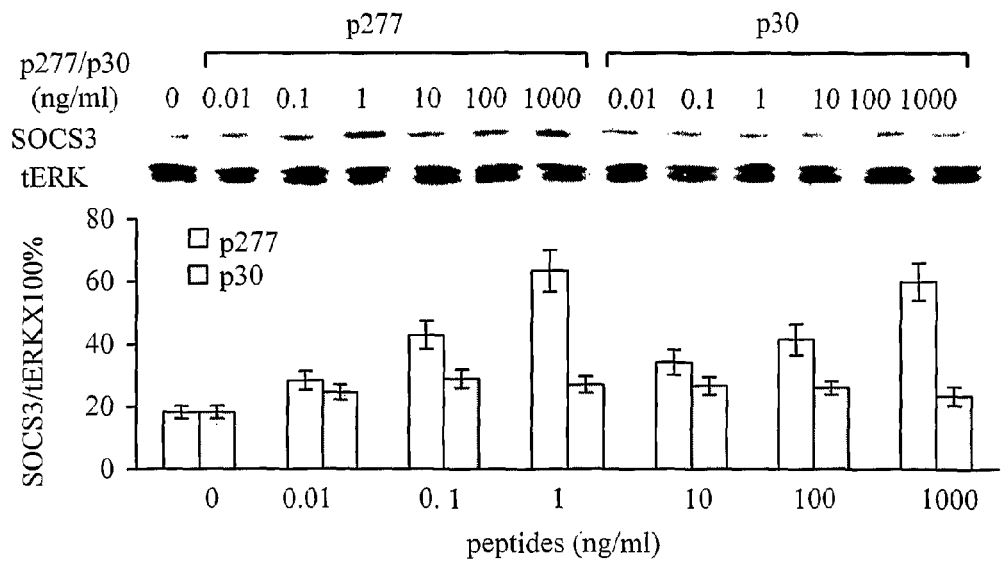

The inventors used p277 synthetic peptide to further rule out the possibility that the effects of HSP60 on SOCS3 expression could be due to contamination by LPS. Peptide p277 (1-1000 ng/ml), but not the control p30 peptide of Tetanus toxoid, induced a marked expression of activated SOCS3 in T cells (FIG. 14E). Thus, the effect of our HSP60 preparation on SOCS3 expression was not due to LPS.

C. p277 is a Co-Stimulator of CD4+CD25+ Regulatory T Cells

Reagents. The following reagents and chemicals were obtained as indicated: RPMI-1640 (Gibco BRL; Paisley, UK), FCS, HEPES buffer, antibiotics, sodium pyruvate (Biological Industries; Kibbutz Beit-Haemek, Israel); phosphatase inhibitor cocktail, LPS (Sigma-Aldrich, Rehovot, Israel). Monoclonal antibodies (mAb) directed to CD4 and CD45RO were obtained from Serotec (Oxford, UK); anti-CTLA4 (BNI3) was from BD Pharmingen (San Diego, Calif.), PE-conjugated anti-CD25 was from Miltenyi Biotec (Bergisch Gladbach, Germany). Monoclonal antibodies (mAb) anti-TLR2 and anti-TLR4 were purchased from eBioscience (San-Diego, Calif.). Antibodies anti-phosphorylated Pyk2 (clone py881), anti-phosphorylated p38, and anti-phosphorylated ERK½ were obtained from Biosource (Camarillo, Calif.); and anti-total ERK½ (Sigma); anti-phosphorylated AKT (pAKT) and anti-AKT (Cell Signaling Technology, Beverly Mass.). Polyclonal Ab anti-total ERK½ was obtained from Sigma (Rehovot, Israel); anti-NF-κB p65 (A), anti-T-bet (39D), anti-total Pyk2 (clone N-19), anti-total p38, and anti-Lamin B (C-20) were purchased from Santa-Cruz Biotech (Santa-Cruz, Calif.). The anti-Foxp3 antibody (clone Poly6238) was purchased from BioLegend (San-Diego, Calif.). The inhibitors of intracellular protein kinases: GF109203X, were from LC Laboratories (Woburn, Mass.); wortmanin, PD 98059, SB 203580, and Pertussis Toxin were from Calbiochem (La Jolla, Calif.). Neutralizing antibodies anti-IL-10 (clone 23738.11) and anti-TGF-β (clone 9016) were purchased from R&D Systems (Minneapolis, Minn.). The recombinant HSP60 (StressGen Biotechnologies; Victoria, BC, Canada) used in this study contained less than 0.001 EU/ml (0.1 pg/ml) of bacterial endotoxin, as determined using a kinetic-turbidimetric LAL test method (Biological Industries, Kibutz Beit-Haemek, Israel). The peptides used in this study were prepared using standard FMOC chemistry as previously described (Raz et al., 2001). The sequence of p277 that was used in the following Examples 16-25 is VLGGGVALLRVIPALDSLTPANED, (p277(Val$^6$Val$^{11}$), SEQ ID NO:2). The sequence of MTp277 is VAGGGVTLLQAAPTLDELKLEG of HSP65 of *Mycobacterium tuberculosis* (SEQ ID NO:10).

Purified T-cell populations. T cells were purified from the peripheral blood of healthy human donors (Blood Bank; Tel-Hashomer, Israel). The whole blood was incubated (20 min, 22° C.) with RosetteSep™ human T-cell enrichment cocktail (CD3+ T cells), or with RosetteSep™ human CD4+ and CD8+ T-cell enrichment cocktail, (StemCell Technologies, Vencouver, BC, Canada). The remaining un-sedimented cells were then loaded onto Lymphocyte Separation Medium (ICN Biomedicals; Belgium), isolated by density centrifugation, and washed with PBS. The purified cells (>97% CD3+ T cells, >95% CD4+ T cells, >95% CD8+ T cells) so obtained were cultured in RPMI containing antibiotics and 10% heat-inactivated FCS. In a second round of purification, CD4+ T cells were separated to CD25− and CD25+ populations with magnetically coupled mAb against human CD25 (Miltenyi Biotec; Bergisch Gladbach, Germany). The purified cells obtained (usually >90% CD4+CD25+ or >99% CD4+CD25− T cells) were cultured in RPMI containing antibiotics and 10% heat-inactivated FCS.

Cytokine secretion. Cytokine secretion was determined by ELISA as described in section D of the Examples herein, using the appropriate mAb, according to the manufacturer's instructions (Biosource; Camarillo, Calif.).

Flow cytometry. Indicated populations of T cells ($10^6$ cells per sample) were stained (30 min, 4° C.) with anti-CD25-PE, anti-CD4-FITC, or anti-CD45RO-PE, washed with PBS (containing 0.05% BSA and 0.05% sodium azide). For intracellular staining, cells were fixed with 3% paraformaldehyde (20 min, at 25° C.), and washed. Cell-membranes were permeabilizied with 0.5% TritonX-100 in PBS (10 min, at 25° C.), washed, and stained (30 min, 4° C.) with anti-CTLA4, anti-TLR2, or anti-TLR4 (20 μg/ml), washed, and incubated (30 min, 4° C.) with an FITC-conjugated goat anti-mouse IgG (Jackson ImmunoResearch Lab. Inc., West Grove, Pa.). After washing, T cell staining was analyzed using a Becton Dickinson FACSort (Mountain View, Calif.) using the Cell Quest software.

Co-culture and transwell analysis. In co-culture experiments, CD4+CD25+ T cells were incubated with HSP60 (1 ng/ml, 2 hr), washed, and added at different percentage (1%, 10%, and 25%) to CD4+CD25− T cells. The cells were co-cultured on anti-CD3 mAb pre-coated 24-well plates for 24 hr (cytokine secretion), or 24 and 96 hr (proliferation). In Transwell analysis, CD4+CD25− and CD4+CD25− T cells were cultured in Transwell plates (Costar, Corning, N.Y.). Both chambers of each Transwell were coated with anti-CD3 mAb (1 μg/ml). The supernatants for cytokine analysis were collected from both chambers after 24 hr.

CFSE labeling of CD4+CD25− T cells. CD4+CD25− T cells were labeled with Vybrant™ CFDA SE Cell Tracer Kit (Molecular Probes; Eugene, Oreg.) according to the manufacturer's instructions. Labeled CD4+CD25− T cells were co-cultured with CD4+CD25+ T cells on anti-CD3 mAb, as described above, for 6 hr. After co-culture, CD4+CD25− T cells were isolated by sorting using a Becton Dickinson FACSVantage (Mountain View, Calif.).

Proliferation assay. Proliferation was assessed by the 2,3 bis[2-Methoxy-4-nitro-5-sulfophenyl]-2H-tetrazolium-5-carboxanilide (XTT) assay (Mosmann, 1983).

Western blot analysis of T-cell lysates. Indicated populations of T cells ($5 \times 10^6$) were preincubated with 1 ng/ml of HSP60 for 10 min (37° C. in a 7% $CO_2$, humidified atmosphere). The cells were then washed and replated in the same concentration on anti-CD3 mAb pre-coated 24-well plates for 4 hr (37° C. in a 7% $CO_2$, humidified atmosphere). Total cell lysates, nuclear and cytoplasmic extracts were prepared as previously described (Zanin-Zhorov et al., 2003, section D of the Examples herein), analyzed for protein content. Sample buffer was then added and, after boiling, the samples, containing equal amounts of proteins, were separated on 10% SDS-PAGE gel and transferred to nitrocellulose membranes. The membranes were blocked and probed with the following mAb in the same buffer: anti-phosphorylated (p) ERK. (0.2 μg/ml), anti-total (t) ERK (diluted 1:20,000), anti-pPyk2 (1.5 μg/ml), anti-tPyk2 (0.2 μg/ml), anti-pAKT (diluted 1:1000), anti-tAKT (diluted 1:1000), anti-p38 (diluted 1:500), and anti-tp38 (diluted 1:1000), anti-Foxp3 (diluted 1:250), anti-NF-κB (diluted 1:1000), anti-T-bet (diluted 1:1000), and anti-Lamin B (diluted 1:1000). Immunoreactive protein bands were visualized using a horseradish peroxidase-conjugated goat anti-mouse Ab and the enhanced ECL system. Phosphorylation levels of the 3-5 independent experiments were estimated by densitometry.

Statistics, Data were analyzed by Student's t-test. P<0.05 was considered statistically significant.

Example 16

Figure 15A:
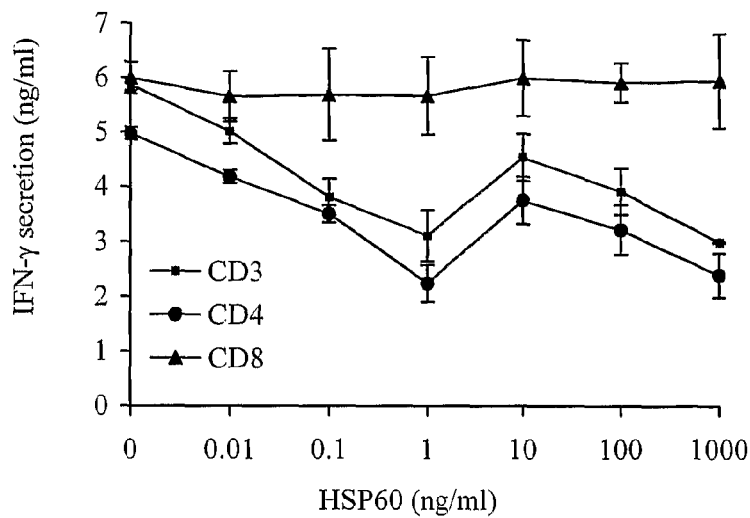
FIG. 15. HSP60 inhibits anti-CD3-induced IFN-γ (a) and TNF-α (b) secretion, and up-regulates IL-10 (c) secretion in CD3$^+$ T cells and CD4$^+$, but not in CD8$^+$ T cells. Purified CD3$^+$, CD4$^+$, and CD8$^+$ T cells were pre-incubated with the indicated concentrations of HSP60 for 2 hours, washed and transferred to 24-well plates coated with mAb anti-CD3 (OKT; 0.5 µg/ml) in serum-free medium. The supernatants were collected after 24 hr and analyzed for IFN-γ (A), TNF-α (B) and IL-10 (C) secretion. The means±SD of five different donors are shown. *P<0.05.
Figure 15B:
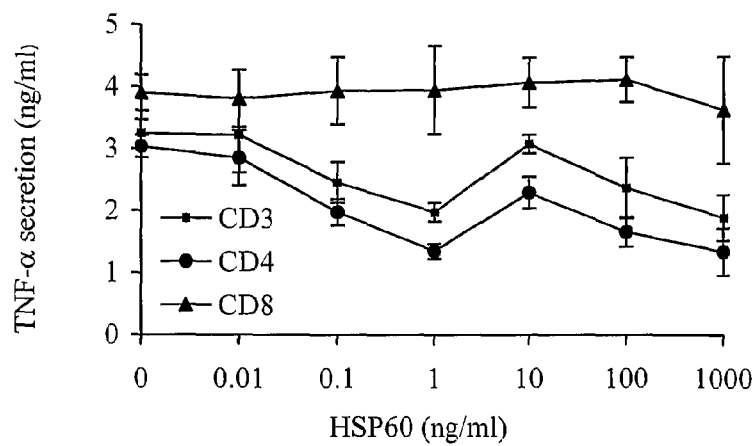
Figure 15C:
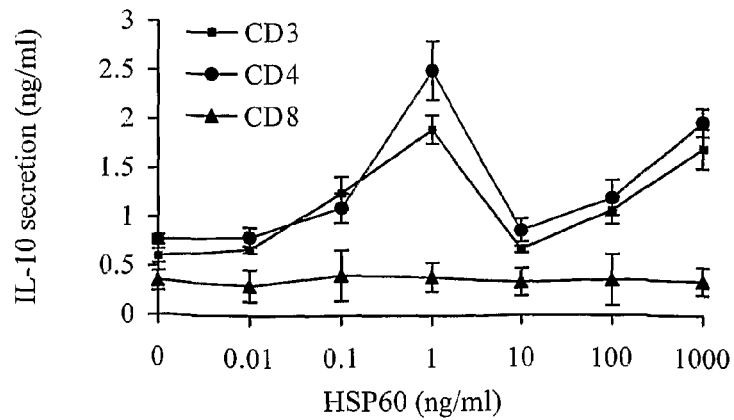

HSP60 Inhibits IFNγ and TNFα Secretion and Up-Regulates IL-10Secretion in CD3+ and in CD4+ T Cells, but not in CD8+ T Cells The inventors analyzed the effects of HSP60 on the cytokine secretion profile of freshly isolated and purified human CD3+, CD4+, and CD8+ T cells that were activated by mitogenic anti-CD3 mAb. HSP60 alone (at a range of concentrations of 0.01-1000 ng/ml) did not induce cytokine secretion by the T cells. However, when the CD3+ and CD4+ T cells were pre-treated with different concentrations of HSP60, washed and then activated by anti-CD3, the secretion of the Th1-related cytokines IFN-γ and TNF-α was inhibited by about 50% (FIGS. 15A and 15B), while IL-10 secretion was enhanced 2-3 fold (FIG. 15C). In contrast, CD8+ T cells were unresponsive to HSP60 at all concentrations tested (FIG. 15). Recently, the inventors reported that the biological effects of HSP60 on T cells manifested a bi-phasic bell-shaped dose-response curve (Zanin-Zhorov et al., 2003, Example 27 herein); here too the dose-response also manifested a bi-phasic bell-shaped. Significant effects were achieved with relatively low concentrations of HSP60 (0.1-1.0 ng/ml; $P<0.05$), while higher doses (in the order of 10 ng/ml) did not affect cytokine secretion. However, cytokine secretion was again affected significantly at higher concentrations of HSP60 (0.1-1 μpg/ml; $P<0.05$). Thus, HSP60 specifically affects cytokine secretion in CD3+ and CD4+, but not CD8+ T cells.

Example 17

Figure 16A:
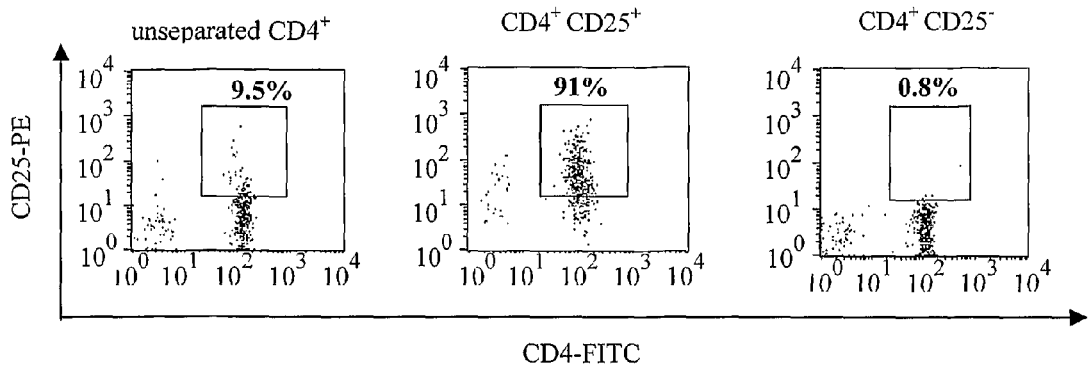
FIG. 16. HSP60 does not affect IFN-γ and TNF-α secretion by activated CD4+ CD25− T cells, but up-regulates IL-10 and TGF-β secretion by activated CD4+ CD25+ T cells. A. and B. Unseparated CD4+, CD4+ $^{CD}$25+, and CD4+ CD25− T cells were stained with 20 µg/ml PE-conjugated mAb anti-CD25, FITC-conjugated mAb anti-CD4, anti-CTLA4, or anti-CD45RO, followed by a secondary FITC-conjugated Ab. Marker expression was determined by FACScan analysis. Foxp3 levels were measured in cell lysates. One representative experiment of five is shown. C. Unseparated CD4+, CD4+ CD25+, and CD4+ CD25− T cells were incubated with HSP60 (1 ng/ml) for 2 hours, washed and transferred to 24-well plates coated with mAb anti-CD3 (OKT; 0.5 µg/ml) in serum-free medium. The supernatants were analyzed for IFN-γ, TNF-α, IL-10, and TGF-β secretion. The means±SD of five different donors are shown. *P<0.05.
Figure 16B:
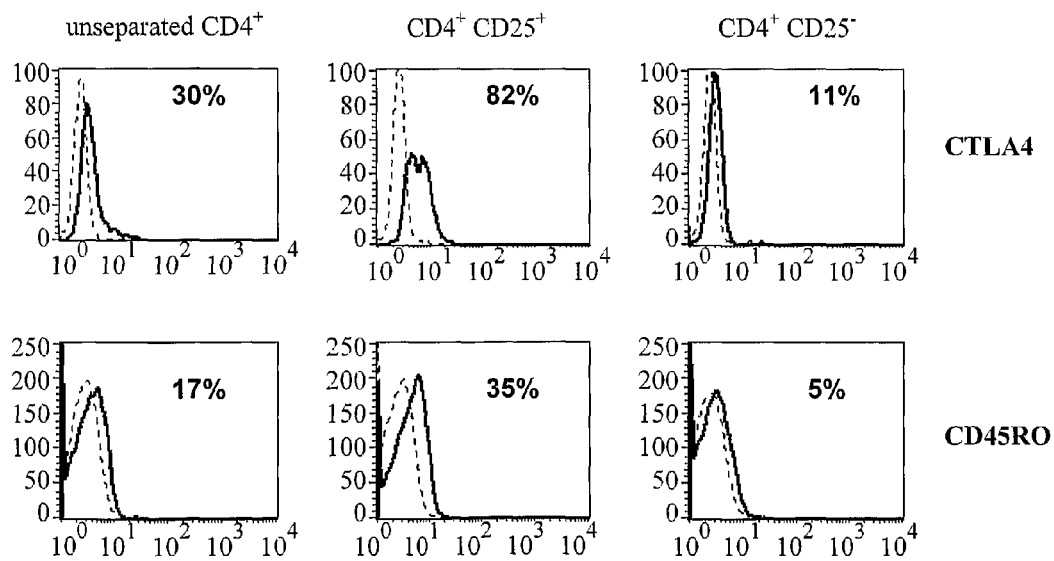
Figure 16B:
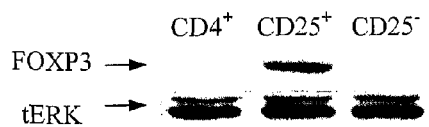
Figure 16C:
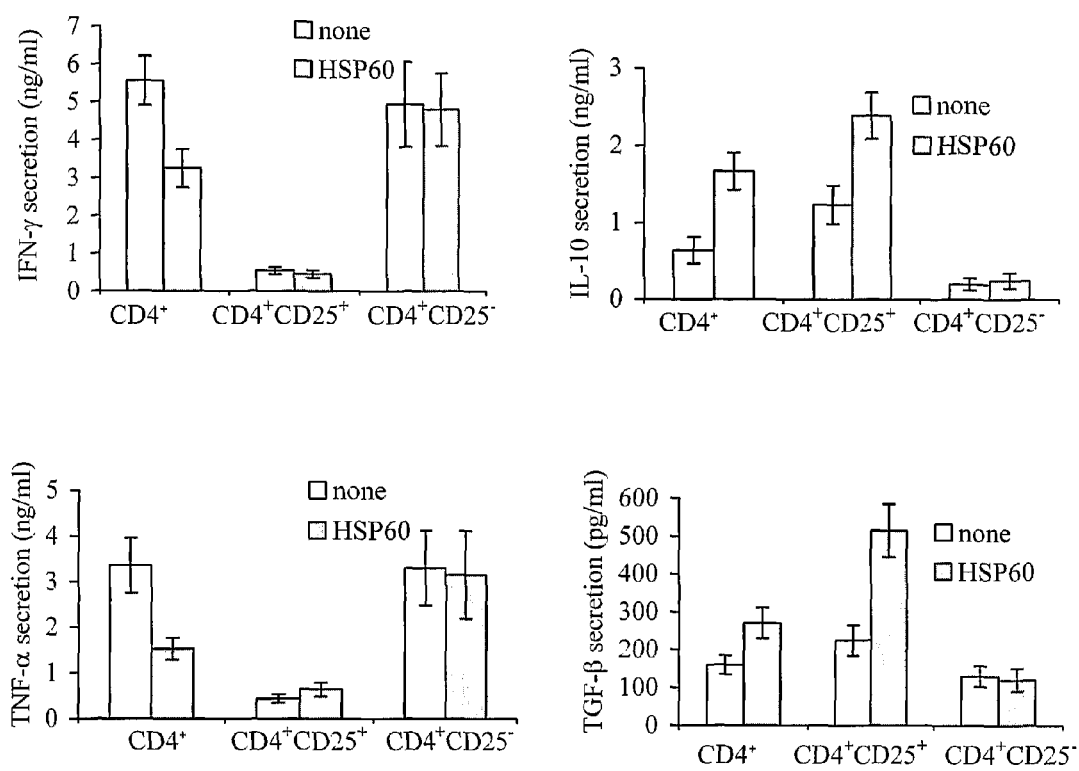

Depletion of CD4+CD25+ T Cells Prevents the Inhibitory Effect of HSP60 on IFN-γ and TNF-α Secretion in CD4+CD25− T Cells Cell surface staining of purified human CD4+ peripheral blood T cells revealed that about 10% of these cells expressed the CD25 marker (FIG. 16A). After purification, the CD4+CD25+ population expressed relatively high levels of intracellular CTLA4 and surface CD45RO markers, and transcription factor Foxp3 (FIG. 16B). To test whether CD4+CD25+ T cells are essential for the inhibitory effect of HSP60 on T-cell cytokine secretion, unseparated CD4+ T cells, purified CD4+CD25+T cells, or purified CD4+CD25− T cells were incubated with HSP60 (1 ng/ml, 2 hours), washed the cells, and then activated them using mitogenic anti-CD3 mAbs for 24 hours. Depletion of the CD4+CD25+ T cells completely prevented the inhibition of IFN-γ and TNF-α secretion by HSP60 treatment (FIG. 16C).

Example 18

HSP60 Induces IL-10 and TGF-β Secretion in CD4+CD25+, but not in CD4+CD25− T Cells Although the relative contribution of the immunosuppressive cytokines IL-10 and TGF-β in the function of Tregs is controversial, the supernatants described above were analyzed (FIGS. 16C) for levels of IL-10 and TGF-β. Treatment of un-separated CD4+ or CD4+CD25+, but not of CD4+CD25− T cells with HSP60 significantly up-regulated the secretion of IL-10 and TGF-β induced by mitogenic anti-CD3 (FIG. 16C).

Example 19

Figure 17A:
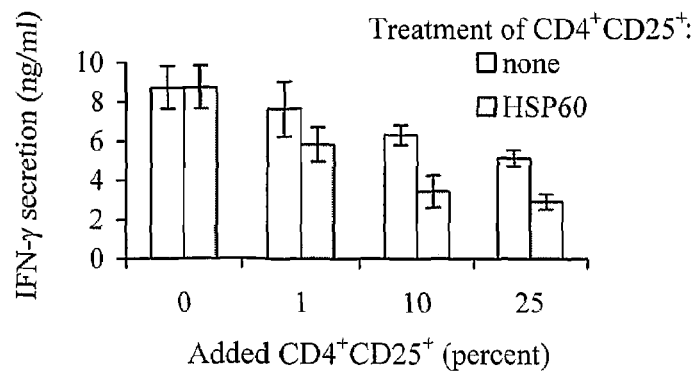
FIG. 17. Treatment of CD4+CD25+ T cells with HSP60 affects cytokine secretion and proliferation in co-culture with CD4+CD25− T cells. Purified CD4+CD25+ T cells were incubated with HSP60 (1 ng/ml) for 2 hours, washed, mixed in the indicated proportions with CD4+CD25− T cells, and transferred to 24-well plates coated with mAb anti-CD3 (OKT; 0.5 µg/ml) in serum-free medium. The supernatants were collected after 24 hr and analyzed for IFN-γ (A), TNF-α (B), IL-10 (C) and TGF-β (D). Cell proliferation was determined after 24 and 96 hr (E). The means±SD of six different donors are shown.
Figure 17B:
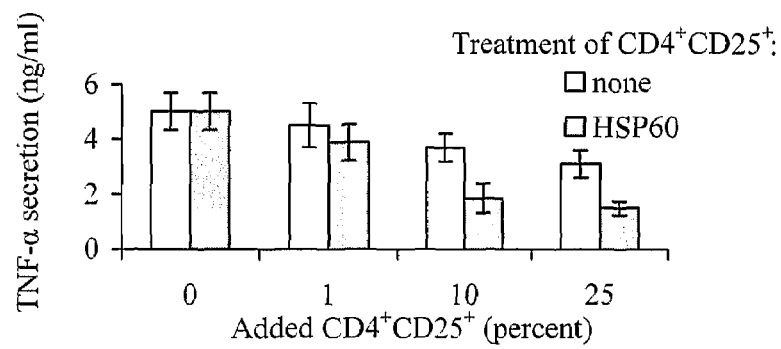
Figure 17C:
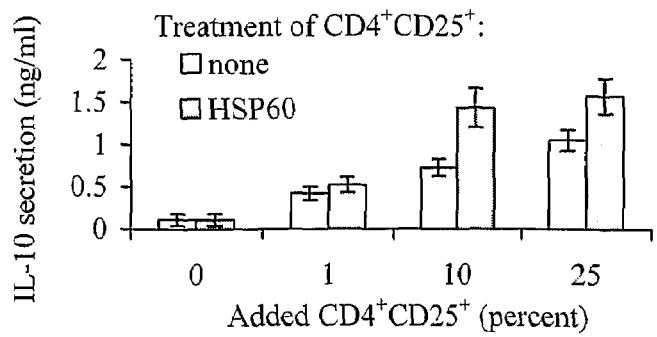
Figure 17D:
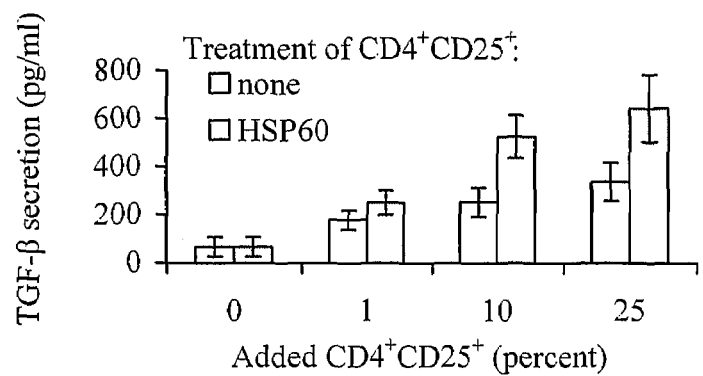

Treatment of CD4+CD25+ T Cells with HSP60 Affects Cytokine Secretion and Proliferation in Co-Culture with CD4+CD25− T Cells To confirm the involvement of CD4+CD25+ Tregs in the effects of HSP60 on cytokine secretion, the inventors incubated only this population with HSP60 and washed the cells. The HSP60-treated CD4+CD25+ T cells were then co-cultured with the CD4+CD25− T cells in different proportions on mitogenic anti-CD3 for 24 hr, and the cytokine levels were measured. FIGS. 17A and 17B show that the co-culture of untreated CD4+CD25+ T cells with the CD4+CD25− T cells resulted in a relatively moderate effect on cytokine secretion. However, HSP60 treatment of the CD4+CD25+ T cells significantly enhanced the down-regulation of secretion of IFN-γ and TNF-α secretion and up-regulated the secretion of IL-10 and TGF-β in the co-cultures (FIG. 17A-17D).

Example 20

Figure 17E:
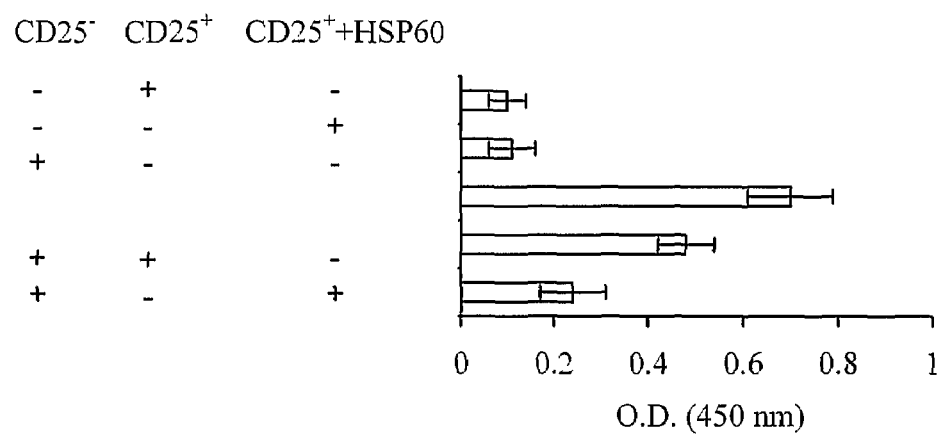

The Effects of HSP60 on T-Cell Proliferation were Measured in these Co-Cultures After 24 and 96 Hours HSP60 treatment of the CD4+CD25+ T cells did not suppress anti-CD3-induced proliferation of the CD4+CD25− T cells at 24 hours. However, at 96 hours there was a significant inhibition of proliferation of the CD4+CD25− T cells (FIG. 17E). Thus, HSP60 treatment of CD4+CD25+ T cells enhanced their ability to inhibit both cytokine secretion and proliferation in co-cultures with untreated CD4+CD25− T cells activated by mitogenic anti-CD3.

Example 21

Figure 18A:
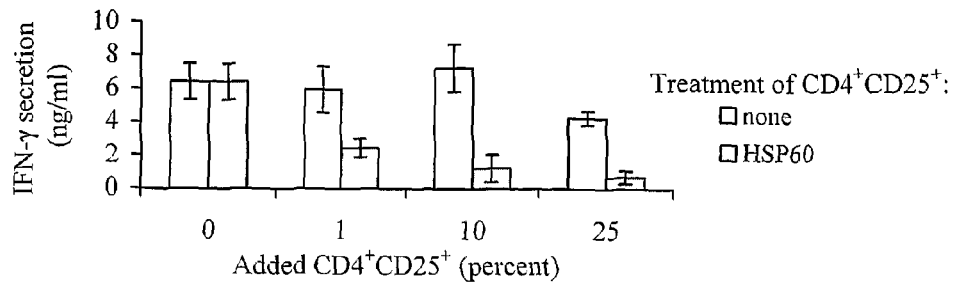
FIG. 18. Treatment of CD4+CD25+ T cells with HSP60 affects cytokine secretion in co-culture with CD8+ T cells. Purified CD4+CD25+ T cells were incubated with HSP60 (1 ng/ml) for 2 hours, washed, mixed in indicated proportions with CD8+ T cells, and transferred to 24-well plates coated with mAb anti-CD3 (OKT; 0.5 µg/ml) in serum-free medium. The supernatants were collected after 24 hr and analyzed for IFN-γ (A), TNF-α (B), IL-10 (C) and TGF-β (D). The means±SD of five different donors are shown.
Figure 18B:
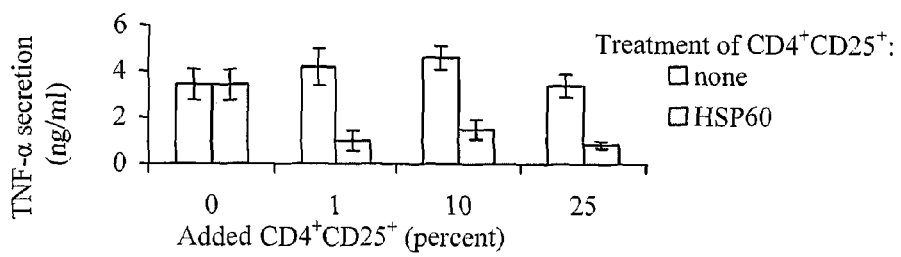
Figure 18C:
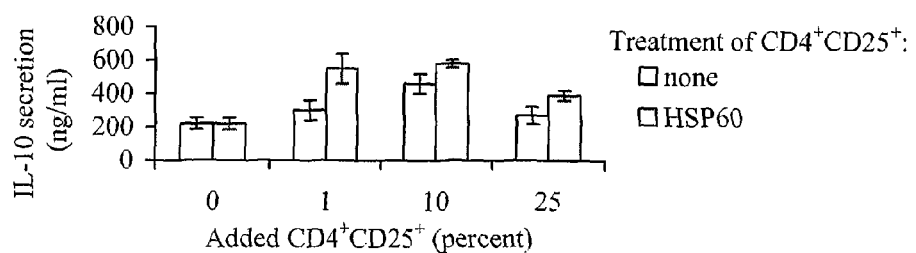
Figure 18D:
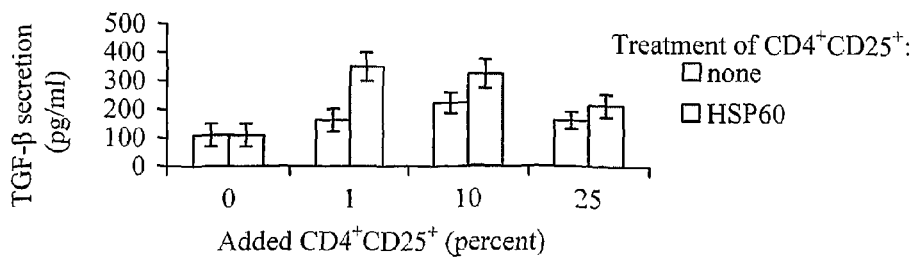

Treatment of CD4+CD25+ T Cells with HSP60 Affects Cytokine Secretion in Co-Culture with CD8+ T Cells The inventors found that HSP60 did not directly affect cytokine secretion in cultures of CD8+ T cells free of CD4+ T cells (FIG. 15). It has been reported, however, that CD4+CD25+ T cells can suppress CD8+ T cells as well as CD4+CD25− T cells. The inventors therefore co-cultured purified CD8+ T cells with HSP60-treated or untreated CD4+CD25+ T cells in different proportions on mitogenic anti-CD3 for 24 hr, and measured the cytokine levels. FIGS. 18A and 18B show that, in contrast to CD4+CD25− T cells (FIGS. 17A and 17B), co-culture of CD8+ T cells with untreated CD4+CD25+ T cells (in all proportions) did not affect IFN-γ or TNF-α secretion. However, the addition of 1% or more HSP60-treated CD4+CD25+ T cells led to inhibition of IFN-γ or TNF-α cytokine secretion by 3-4 fold (FIGS. 18A and 18B). In addition, the secretion of IL-10 and TGF-β was up-regulated in the co-culture of HSP60-treated CD4+CD25+ and CD8+ T cells. Thus, co-culture of untreated CD8+ T cells with HSP60-treated CD4+CD25+ T cells significantly modulated the cytokine secretion profile; HSP60 can affect CD8+ T cells indirectly through the activation of CD4+CD25+ Tregs. However, in the studies below of mechanisms and signal transduction events underling the effects of HSP60 treatment on CD4+CD25+ T cells, co-culture with the CD4+CD25− population was used as a read-out.

Example 22

The Effects of HSP60 on CD4+CD25+ T Cells Depend on TLR2Signaling

Figure 19A:
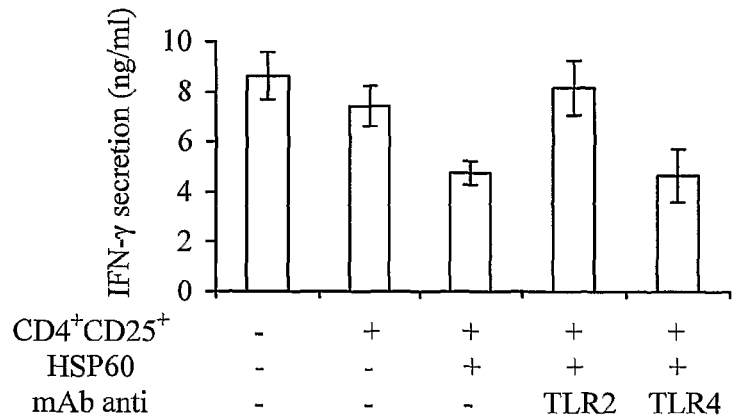
FIG. 19. The effects of HSP60 on CD4+CD25+ T cells depend on TLR2 signaling, and are not due to contaminating LPS. Purified CD4+CD25+ T cells were pretreated with monoclonal anti-TLR2 or anti-TLR4 (20 µg/ml, 30 min). Then, the cells were incubated with HSP60 (1 ng/ml, 2 hr), washed, and co-cultured with CD4+CD25− T cells (ratio 1:9) on anti-CD3 in serum-free medium (A-C). D. Unseparated CD4+, CD4+CD25+, and CD4+CD25− T cells were fixed, permeabilizied and stained with anti-TLR2, or anti-TLR4 (20 µg/ml). Receptor expression was determined by FACScan analysis; E-G. CD4+CD25+T cells were incubated (2 hr) with untreated, PMB-treated, or boiled (100° C., 30 min) HSP60 (1 ng/ml) and LPS (100 ng/ml). After washing, the CD4+ CD25+ T cells were co-cultured with CD4+CD25− T cells (ratio 1:9) on anti-CD3 in serum-free medium. The supernatants were collected after 24 hr and analyzed for IFN-γ (A, E), TNF-α (B, F) and IL-10 (C, G). The means±SD of four different donors are shown. *P<0.05.
Figure 19B:
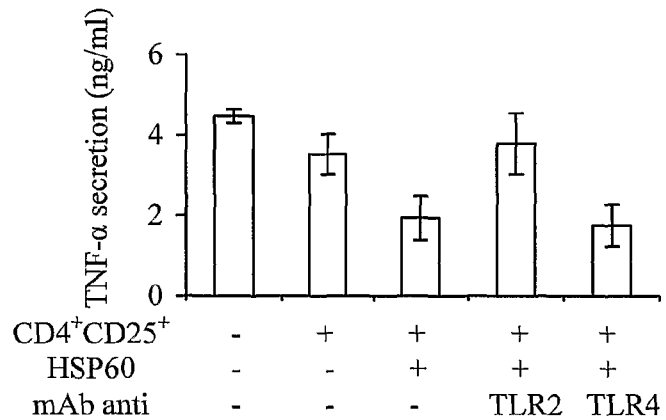
Figure 19C:
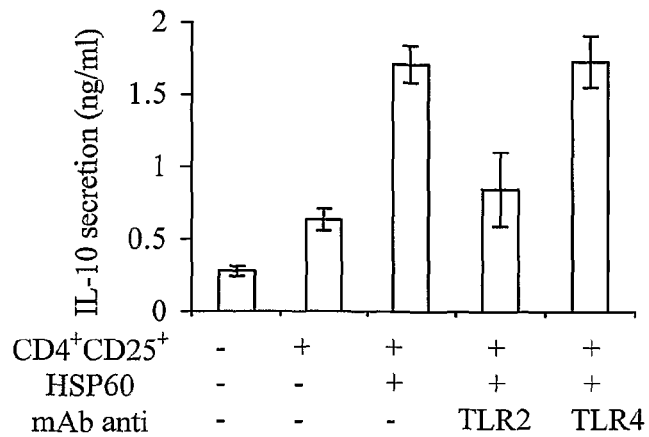

The inventors previously reported that HSP60 affects T-cell behavior innately via TLR2 signaling (Zanin-Zhorov et al., 2003, section D of the Examples herein). Here, whether TLR2 or TLR4 was functionally involved in the effects of HSP60 on CD4+CD25+ T cells was tested. CD4+CD25+ T cells were pre-incubated with anti-TLR2 or TLR4 mAb (both are mouse IgG2a antibodies) prior to activation with HSP60, and assayed the cytokine secretion profile induced by anti-CD3 in the co-culture (ratio 1:9) of the CD4+CD25+ T cells with untreated CD4+CD25- T cells. The inventors found that the mAb to TLR2, but not the mAb to TLR4, blocked the effects of HSP60 on the down-regulation of IFN-γ and TNF-α secretion (FIGS. 19A and 19B) and the up-regulation of IL-10 secretion (FIG. 19C). Thus, TLR2 appears to play a role in mediating the effects of HSP60 on CD4+CD25+ Treg cells.

The inventors tested whether the CD4+CD25+ population expresses higher levels of TLR2 than do CD4+CD25- T cells. In contrast to the results reported in mouse cells, the inventors found by intracellular FACS staining that CD4+CD25+ T cells were much richer in TLR2 than in TLR4. However, no significant differences were found in TLR2 levels between CD4+CD25+ and CD4+CD25- T cells (FIG. 19D).

Example 23

The Effects of HSP60 on CD4+CD25+ T Cells are not Due to Contaminating LPS

LPS-TLR2 interactions can transmit intracellular activation signals in various types of leukocytes. The following studies were performed to further exclude the possibility that even minute amounts of LPS or other lipoprotein contaminants from the *Escherichia coli* recombinant HSP60 might activate the CD4+CD25+ T cells. The inventors incubated the HSP60 with PMB-coupled agarose beads (Gao et al., 2003), collected the unbound material, assayed the protein content, and tested the effect of the PMB-treated HSP60 on CD4+CD25+ T cells. The inventors found that the effects of HSP60 on CD4+CD25+ T cells were completely inhibited by boiling (which denatures proteins, although not LPS), but not by the PMB-beads (FIG. 19E-19G). Pre-incubation with PMB-conjugated agarose beads completely abolished the efficacy of LPS on TNF-α secretion in macrophages. Most importantly, in contrast to its effects on mouse regulatory T cells (Caramalho et al., 2003), the present inventors found that purified LPS did not activate human CD4+CD25+ Treg cells (FIGS. 19E and 19F). Consequently, the effects of HSP60 on CD4+CD25+T cells could not be attributed to LPS.

Example 24

Figure 20A:
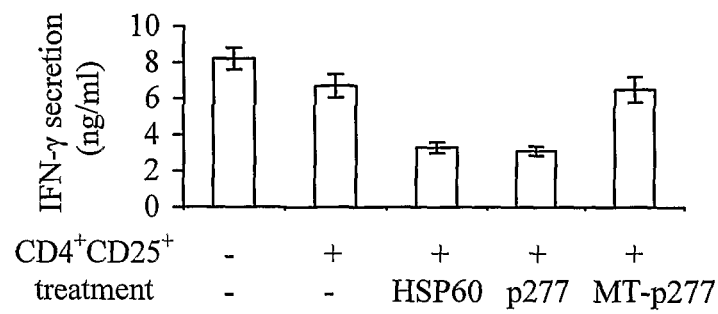
FIG. 20. Treatment of CD4+CD25+ T cells with HSP60 peptide p277 inhibits cytokine secretion and proliferation in co-culture with CD4+CD25− T cells. Purified CD4+CD25+ T cells were incubated with HSP60, p277, or MT-p277 (1 ng/ml) for 2 hours, washed, co-cultured with CD4+CD25− T cells (ratio 1:9) on anti-CD3 in serum-free medium. The supernatants were collected after 24 hr and analyzed for IFN-γ (A), TNF-α (B). Proliferation was determined after 96 hr (C). The means±SD of three different donors are shown.
Figure 20B:
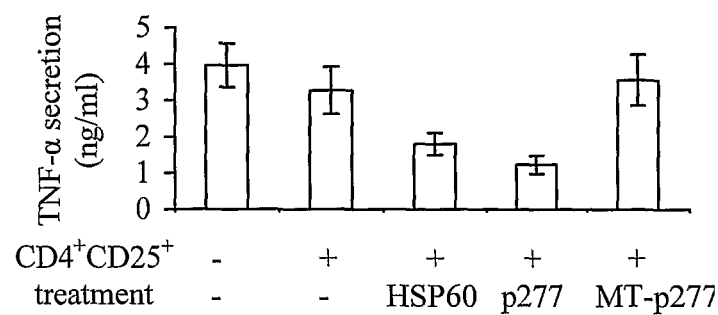
Figure 20C:
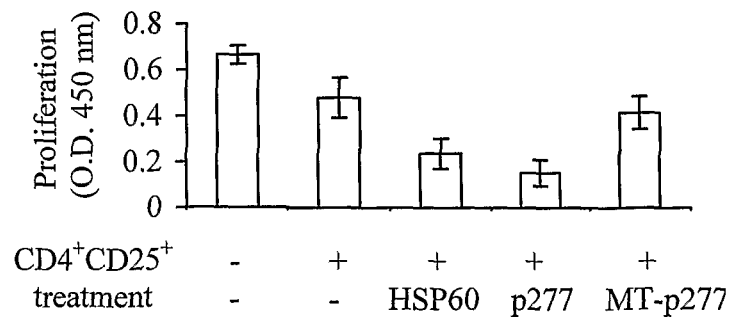

Treatment of CD4+CD25+ T Cells with HSP60-Derived Peptide p277Inhibits Cytokine Secretion and Proliferation in Co-Culture with CD4+CD25- T Cells A synthetic peptide derived from HSP60, amino acid sequence 437-460 called p277, was reported to arrest beta-cell destruction in type 1 diabetes in human patients and in mice (Elias et al., 1997, Raz et al., 2001). These observations suggested that peptide p277 might also enhance the immunomodulatory effects of Tregs. Treatment of CD4+CD25+ T cells with peptide p277 (1 ng/ml, 2 hours), but not with a partially homologous, immunogenic control peptide of *Mycobacterium Tuberculosis*, significantly inhibited IFN-γ and TNF-α secretion, and proliferation in co-culture of the treated CD4+CD25+ with untreated CD4+CD25' T cells (FIG. 20). Thus, peptide p277 too can function as a co-activator of Tregs. Moreover, these results using a synthetic peptide cannot easily be attributed to LPS.

Example 25

Figure 21A:
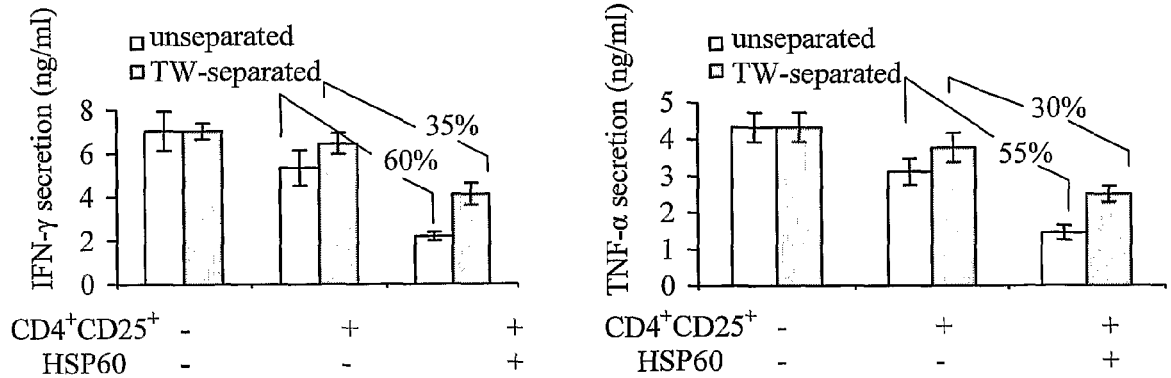
FIG. 21. HSP60-induced enhancement of CD4+CD25+ Treg function involves both contact-dependent and cytokine dependent mechanisms. A. Purified CD4+CD25+ T cells were incubated with HSP60 (1 ng/ml, 2 hr), washed, and co-cultured with CD4+CD25− T cells (ratio 1:9) on anti-CD3 in the same lower well or separately in the upper chamber of the Transwell. As indicated, some CD4+CD25+ T cells were pretreated with control or monoclonal anti-CTLA4 (20 µg/ml, 30 min), and washed (B), or blocking anti-IL-10, and anti-TGF-β (10 µg/ml) mAbs (D) were added to the co-culture. The supernatants were collected after 24 hr and analyzed for IFN-γ and TNF-α. The means±SD of five different donors are shown. C. Purified CD4+CD25+ T cells were incubated with HSP60 (1 ng/ml, 2 hr), washed, and plated on anti-CD3 for 24 hr in serum-free medium. Then, the supernatants were collected, and added to CD4+CD25− T cells in presence of anti-CD3 mAbs. The supernatants from CD4+CD25− T cells were collected after additional 24 hr and analyzed for IFN-γ and TNF-α. The means±SD of four different donors are shown.

HSP60-Induced Enhancement of CD4+CD25+ Treg Function Involves Both Contact-Dependent and Cytokine-Dependent Mechanisms Transwell experiments were performed to investigate whether cell-to-cell contact or soluble mediators were involved in the enhanced effects of HSP60 on the function of CD4+CD25+ Tregs. FIG. 21A demonstrates that separation of HSP60-treated CD4+CD25+ Treg cells from untreated CD4+CD25- T cells by a semi-permeable membrane in transwell chambers reduced the suppressive capacity of CD4+CD25+ T cells for cytokine secretion by about 50%.

Figure 21B:
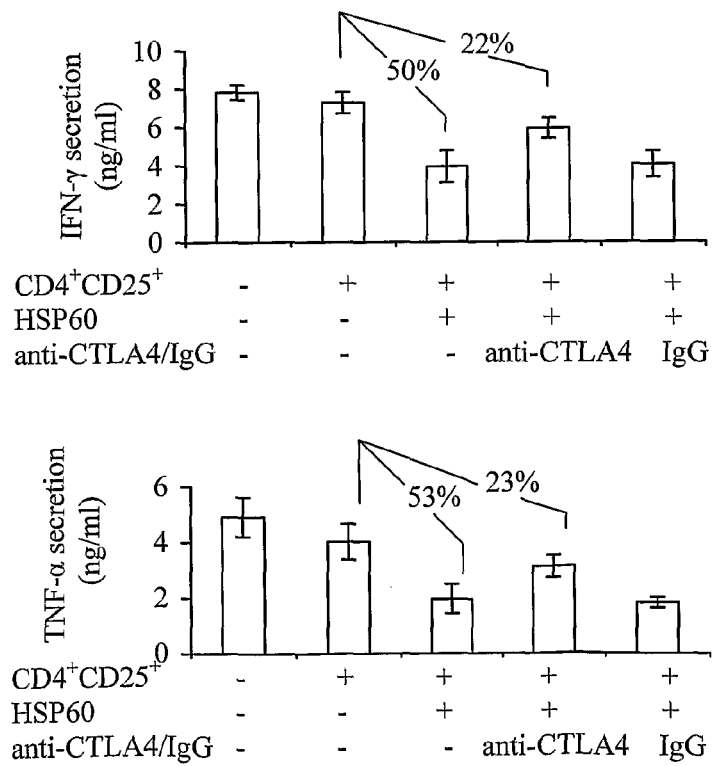

Recently it was reported that the CTLA4 molecule was involved in the suppression mediated by mouse and human CD4+CD25+ regulatory T cells. To clarify the role of CTLA4, CD4+CD25+ Treg cells were pre-incubated with blocking anti-CTLA4 mAb before exposure to HSP60. Then, the treated CD4+CD25+ T cells were co-cultured with CD4+CD25- T cells on mitogenic anti-CD3 mAb. FIG. 21B shows that the anti-CTLA4 mAb blocked by about 50% the ability of HSP60 treatment of the Tregs to inhibit cytokine secretion by the CD4+CD25- T cells. Thus, the affect of HSP60-treated CD4+CD25+ Tregs on CD4+CD25- T cells partially depends on cell contact and the CTLA4 molecule.

Figure 21C:
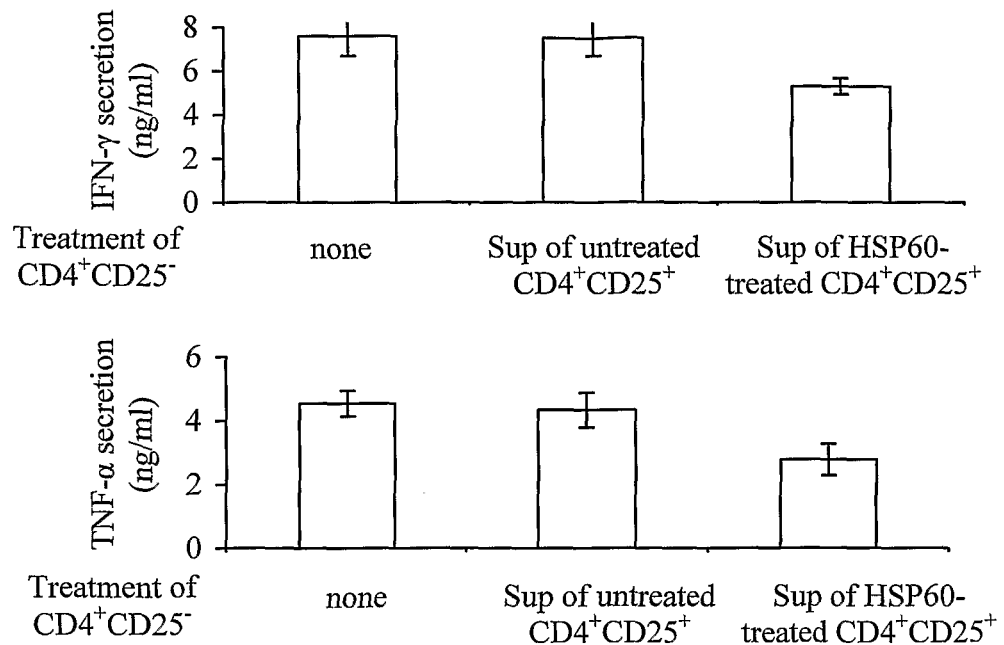
Figure 21D:
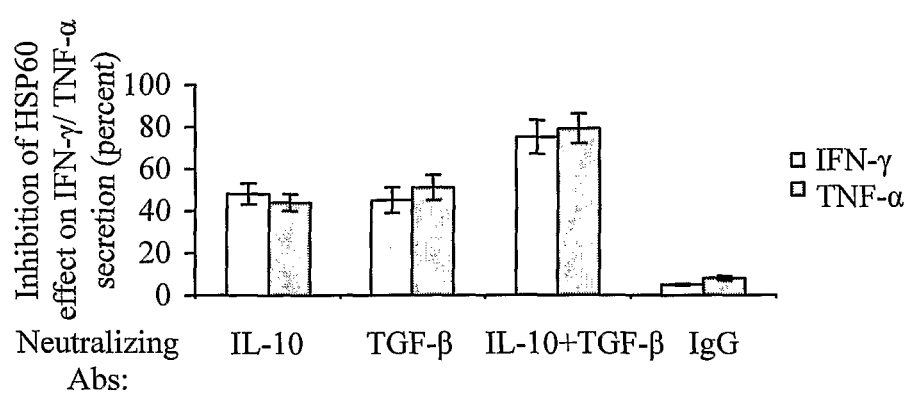
Figure 22A:
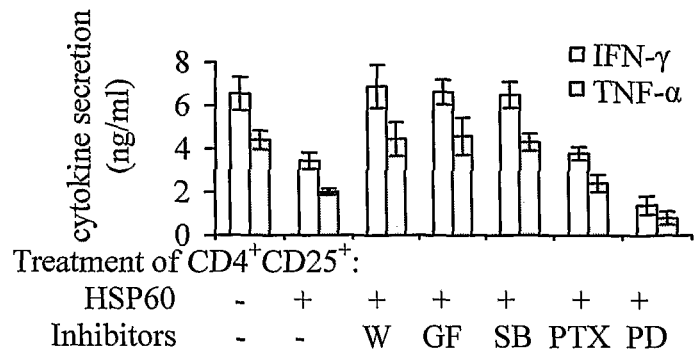
FIG. 22. HSP60 induces phosphorylation of AKT, Pyk-2, p38, and down-regulates anti-CD3-induced ERK-phosphorylation in activated CD4+CD25+ T cells. A. cytokine secretion; B. Akt phosphorylation; C. Pyk-2 phosphorylation; D. p38 phosphorylation; E. Erk phosphorylation.
Figure 22B:
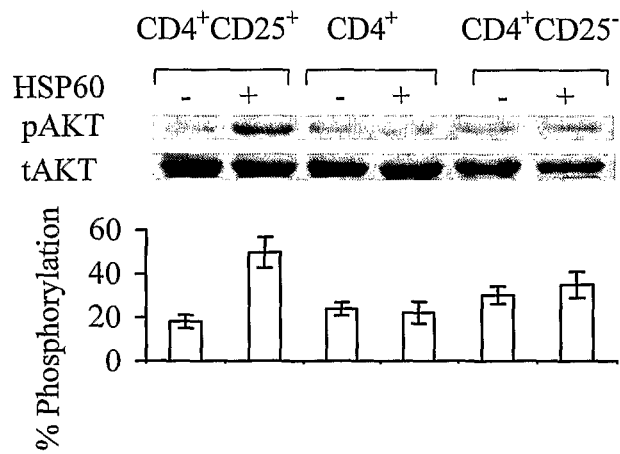
Figure 22C:
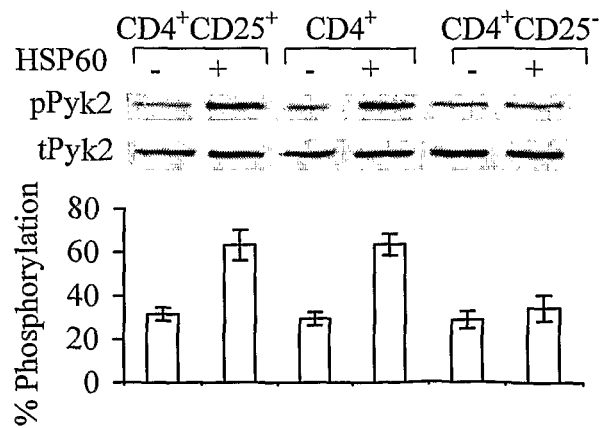
Figure 22D:
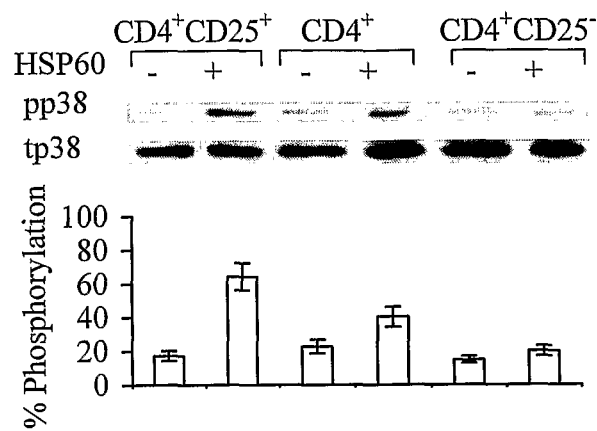
Figure 22E:
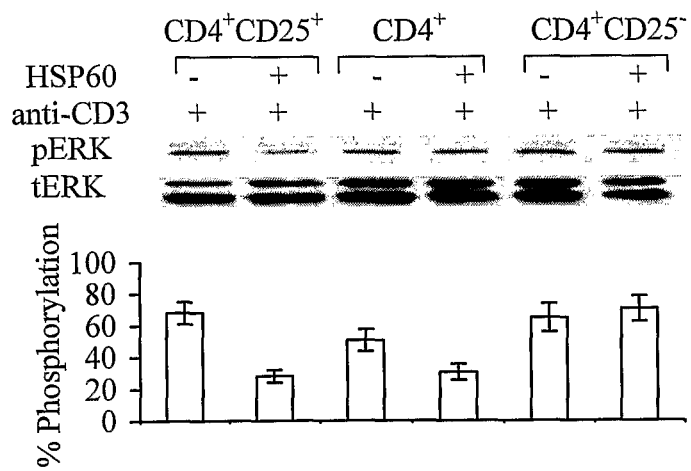

To study whether cytokines had any role, CD4+CD25+ T cells were incubated with or without HSP60 (1 ng/ml, 2 hr), washed, and activated on anti-CD3 mAbs for 24 hr. The supernatants from the CD4+CD25+ Treg cells were collected and added the supernatants to cultured CD4+CD25+ T cells for an additional 24 hr on anti-CD3 mAbs. The inventors assayed IFN-γ and TNF-α secreted by the activated CD4+CD25- T cells. The inventors found that the supernatants from anti-CD3-activated CD4+CD25+ Tregs untreated by HSP60 did not affect cytokine secretion by the CD4+CD25- T cells (FIG. 21C). However, HSP60 treatment of the CD4+CD25+ Treg cells induced them to secrete soluble factors that inhibited IFN-γ and TNF-α secretion by the CD4+CD25- T cells by about 30% (FIG. 21C). Thus, soluble factors account in part for the enhanced function of Tregs induced by HSP60 treatment.

Because HSP60 induced IL-10 and TGF-β secretion by CD4+CD25+ T cells (see FIG. 16C), neutralizing anti-IL-10 and anti-TGF-β mAb were used in the co-culture of CD4+CD25+ and CD4+CD25- T cell populations. Each antibody alone reversed HSP60-induced inhibition of IFN-γ and TNF-α secretion by about 40%; the isotype-matched control mAb did not. Furthermore, presence of both anti-IL-10 and anti-TGF-β antibodies in the co-culture markedly prevented the inhibitory effect on IFN-γ and TNF-α secretion. Thus, HSP60 treatment enhanced the regulatory activity of CD4+CD25+ T cells involved both in contact-dependent (CTLA4) and cytokine-dependent (IL-10, TGF-β) mechanisms.

Example 26

HSP60 Induces Phosphorylation of AKT, Pyk-2, p38, and Down-Regulates Anti-CD3-Induced ERK-Phosphorylation in CD4+CD25+ Treg Cells, and Co-Culture of CD4+CD25− T Cells with HSP60-Treated CD4+CD25+ T Cells Down-Regulates ERK Phosphorylation, and Inhibits Nuclear Translocation of NF-κB and T-Bet Expression in the CD4+CD25− Cells As can be seen in FIG. 22, HSP60 induces phosphorylation of AKT, Pyk-2, p38, and down-regulates anti-CD3-induced ERK-phosphorylation in activated CD4+CD25+ T cells. A. Purified CD4+CD25+ T cells were pretreated with intracellular signal transduction inhibitors wortmanin (5 nM), GF109203X (20 nM), SB203580 (10 μm), pertussis toxin (2 μg/ml), or PD98059 (10 μm). Then, the cells were incubated with HSP60 (1 ng/ml, 2 hrs), washed, co-cultured with CD4+ CD25− T cells (ratio 1:9) on anti-CD3 in serum-free medium. The supernatants were collected after 24 hr and analyzed for IFN-γ and TNF-α; B-E. Unseparated CD4+, CD4+CD25+, and CD4+CD25− T cells were incubated with HSP60 (1 ng/ml) for 10 min, washed, and some cells (E) were exposed to anti-CD3 mAbs (60 min). Lysates of these cells were immunoblotted with antibodies: anti-pAKT and anti-tAKT (B), anti-pPyk2 and anti-tPyk2 (C), anti-pp38 and anti-tp38 (D), or anti-phospho-ERK (pERK) and anti-total ERK (tERK) (E). The blot of 1 experiment representative of three different donors is presented. Phosphorylation levels of the experiments were estimated by densitometry, and an average percentage of phosphorylation±SD was calculated as OD of pAKT/tAKT, or pPyk2/tPyk2, or pp38/tp38pERK/tERK× 100%.

Thus, HSP60 induced phosphorylation of AKT, Pyk-2, and p38, whereas ERK phopshorylation induced by anti-CD3 was inhibited in CD4+CD25+ T cells.

Figure 23A:
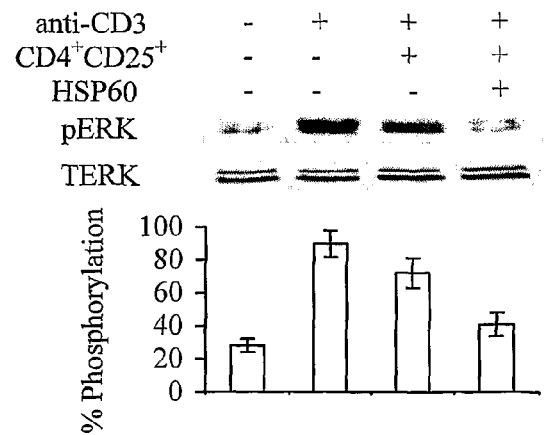
FIG. 23. Co-culture of CD4+CD25− T cells with HSP60-treated CD4+CD25+ T cells down-regulates ERK phosphorylation (A), inhibits, nuclear translocation of NF-κB (B), and T-bet (C) expression in the CD4+CD25− T cells.
Figure 23B:
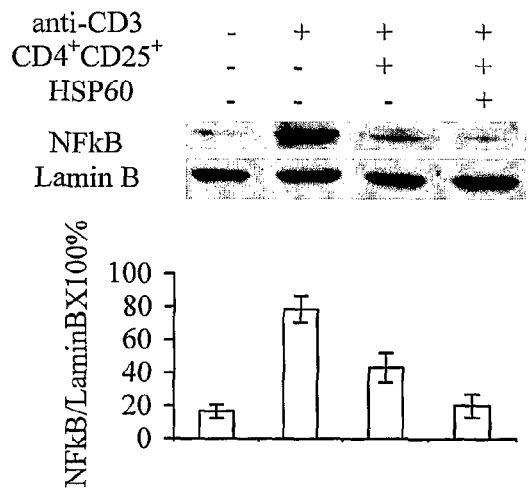
Figure 23C:
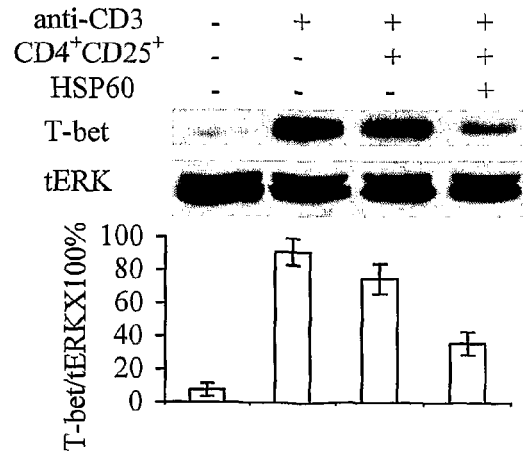

As can be seen in FIG. 23, Co-culture of CD4+CD25− T cells with HSP60-treated CD4+CD25+ T cells down-regulates ERK phopsphorylation (A), inhibits, nuclear translocation of NF-κB (B), and T-bet (C) expression in the CD4+ CD25− T cells. Purified CD4+CD25− T cells were labeled with CFSE, washed, and co-cultured with HSP60-treated (1 ng/ml, 2 hr) CD4+CD25+ T cells (ratio 1:9) on anti-CD3 in serum-free medium for 6 hr. The CD4+CD25− T cells were re-isolated by FACS sorting and cell lysates of these cells were immunoblotted with antibodies: anti-phospho-ERK (pERK) and anti-total ERK (tERK) (A), anti-NF-κB and anti-Lamin B (B), anti-T-bet and anti-total ERK (tERK) (C). The blot of 1 experiment representative of four different donors is presented. The levels of ERK phosphorylation, NF-κB, and T-bet were estimated by densitometry and the average percentage derived from four different donors was shown.

Thus, co-culture of CD4+CD25− T cells with HSP60-treated CD4+CD25+ Treg cells resulted in down-regulation of ERK phosphorylation, inhibition of nuclear translocation of NF-κB and T-bet expression in the regulated CD4+CD25− T cells.

D. HSP60 and p277 Inhibit Th1-Mediated Hepatitis Model via Innate Regulation of Th1/Th2 Transcription Factors and Cytokines Reagents. The following reagents and chemicals were obtained as indicated: RPMI-1640 (Gibco BRL; Paisley, UK), FCS, HEPES buffer, antibiotics, sodium pyruvate (Biological Industries; Kibbutz Beit-Haemek, Israel); phosphatase inhibitor cocktail, cycloheximide, PMA, LPS (Sigma-Aldrich, Rehovot, Israel). Monoclonal antibodies (mAb) anti-TLR2 and anti-TLR4 (eBioscience; San-Diego, Calif.); anti-human recombinant HSP60 (designated clone P5, IgM fraction; kindly provided by F. Quintana of The Weizmann Institute of Science). Polyclonal Ab anti-total ERK½ was obtained from Sigma (Rehovot, Israel); anti-SOCS3 (H-103), anti-NF-κb p65 (A), anti-T-bet (39D), anti-GATA-3 (HG3-31), and anti-Lamin B (C-20) were purchased from Santa-Cruz Biotech (Santa-Cruz, Calif.). Purified mouse anti-NFATp/NFATc2 (4G6-G5.1) was purchased from BD Pharmingen (San-Diego, Calif.). The recombinant HSP60 (StressGen Biotechnologies; Victoria, BC, Canada) used in this study contained less than 0.001 EU/ml (0.1 pg/ml) of bacterial endotoxin, as determined using a kinetic-turbidimetric LAL test method (Biological Industries, Kibutz Beit-Haemek, Israel). The peptides p277 (having the amino acid sequence of VLGGGVALLRVIPALDSLTPANED, p277 (Val$^6$Val$^{11}$), SEQ ID NO:2) and MTp277 (having the amino acid sequence of VAGGGVTLLQAAPTLDELKLEG, SEQ ID NO:10) that were used in Examples 27-34 were prepared using standard FMOC chemistry as previously described (Raz et al., 2001), and contained less than 0.001 EU/mg protein (0.1 pg/mg) of bacterial endotoxin as determined using a kinetic-turbidimetric LAL test method.

Human T cells. T cells were purified from the peripheral blood of healthy human donors (Blood Bank; Tel-Hashomer, Israel). The whole blood was incubated (20 min, 22° C.) with RosetteSep™ human T-cell enrichment cocktail (StemCell Technologies, Vancouver, BC, Canada). The remaining unsedimented cells were then loaded onto Lymphocyte Separation Medium (ICN Biomedicals; Belgium), isolated by density centrifugation, and washed with PBS. The purified cells (>95% CD3+ T cells) so obtained were cultured in RPMI containing antibiotics and 10% heat-inactivated FCS.

Cytokine secretion. T cells ($2 \times 10^6$ cells per ml) were activated (1 hr, 37° C.) with the indicated concentrations of HSP60 in 24-well plates in RPMI containing 10% heat-inactivated FCS. The cells were then washed and re-plated at the same concentration on anti-CD3 mAb pre-coated 24-well plates (0.5 μg/ml; non tissue culture grade plates) in serum free medium containing 0.1% BSA at 4° C. for 24 hr. The supernatants were collected, and the cytokine content (TNF-α, IFN-γ, and IL-10) was determined by ELISA, using the appropriate mAb, according to the manufacturer's instructions.

Western blot analysis of T-cell nuclear extracts. Purified T cells ($5 \times 10^6$) were preincubated with different concentrations of HSP60 for the indicated periods of time (37° C. in a 7% $CO_2$, humidified atmosphere). The cells were then washed and replated in the same concentration of HSP60 on anti-CD3 mAb pre-coated 24-well plates for 24 hr (37° C. in a 7% $CO_2$, humidified atmosphere). T cells were lysed in 10 mM HEPES, 1.5 mM $MgCl_2$, 1 mM dithiothreitol (DTT), 1 mM PMSF, 0.5% Nonidet P-40. The lysates were incubated on ice for 10 min and centrifuged at 2000 rpm for 10 min at 4° C. The supernatants (cytoplasmic extracts) were transferred and the pellet (nuclei) was suspended in buffer containing 30 mM HEPES, 450 mM NaCl, 25% Glycerol, 0.5 mM EDTA, 6 mM DTT, 12 mM $MgCl_2$ 1 mM PMSF, 10 μg/ml leupeptin, 10 μg/ml pepstatin, 1% phosphatase inhibitor cocktail, and the suspension was incubated on ice for 30 min. The lysates were cleared by centrifugation (30 min, $14 \times 10^3$ rpm, 4° C.), and the resulting supernatants analyzed for protein content. For NFATp analysis nuclear extracts were prepared with a NE-PER Nuclear and Cytoplasmic Extraction reagent (Pierce, Rockford, Ill.) according to the manufacturer's protocol. Sample buffer was then added and, after boiling, the samples, containing equal amounts of proteins, were separated on 10% SDS-PAGE gel and transferred to nitrocellulose membranes. The membranes were blocked with TBST buffer containing low-fat milk (5%), Tris pH 7.5 (20 mM), NaCl (135 mM) and Tween 20 (0.1%), and probed with the following mAb in the same buffer: anti-NF-κb (diluted 1:1000), anti-total (t) ERK (diluted 1:20,000), anti-NFATp (diluted 1:500), anti T-bet (diluted 1:1000), anti-GATA-3 (diluted 1:1000), anti-Lamin B (diluted 1:1000). Immunoreactive protein bands were visualized using labeled secondary antibodies and the enhanced ECL system.

Induction and evaluation of liver damage. BALB/c mice were maintained at the Animal Breeding Facility of the E. Wolfson Medical Center. Treatment of the animals was in accordance with institutional guidelines. Acute liver injury was induced by injecting 6-8-week-old male mice with concanavalin A (Con-A) (12 mg/ml; Sigma-Aldrich, Rehovot, Israel) in 250 ml of phosphate buffered saline (PBS) via the tail vein. HSP60, p277 or MTp277 were administered (330 μl, 500 ng/ml) i.p. 18 and 1 hr prior to ConA. After 24 hrs, the mice were bled, euthanized with chloral hydrate anesthesia, their abdomens opened by a midline incision and sections from the left liver lobe were excised for histopathologic examination. Liver sections were fixed in a 5% neutral formol solution and stained with hematoxylin and eosin.

Enzymatic assessment of liver injury and determination of serum levels of cytokines. In addition to a histopathological examination, the extent of the liver damage was estimated, by determining the serum levels of alanine aminotransferase (ALT) and aspartate aminotransferase (AST), with an automated Monarch Monoanalyzer 2000 (Allied, Lexington, Mass.) 24 hr after ConA administration. For determination of serum levels of cytokines, blood was drawn from mice 2 hr after administration of Con A. The levels of TNF-α, IL-6, and IL-10 were determined by ELISA, using the appropriate mAb, according to the manufacturers' instructions. Anti mouse TNF-α CytoSets tm was purchased from Biosource (CA, USA). Anti murine IL-6 Eli-pair and anti murine IL-10 Eli-pair were purchased from Diaclone Research (France).

Example 27

HSP60 Inhibits T-Cell IFNγ and TNFα Secretion and Up-Regulates IL-10 Secretion via TLR2

Figure 24A:
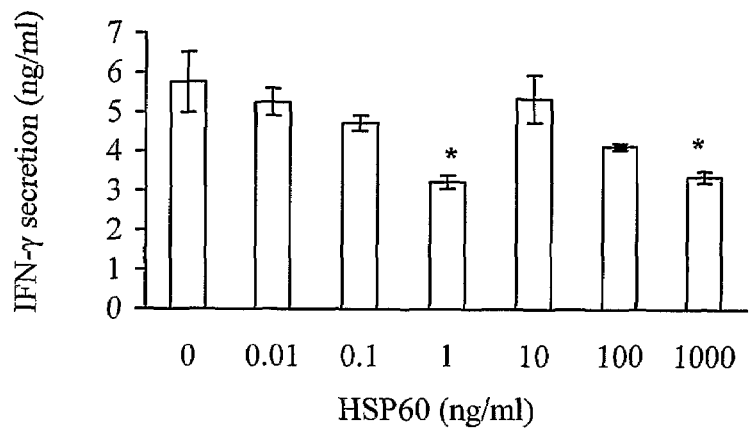
FIG. 24 shows that HSP60 inhibits anti-CD3-induced IFN-γ (a) and TNF-α (b) secretion, and up-regulates IL-10 (c) secretion by T cells. Purified human T cells were pre-incubated with the indicated concentrations of HSP60 for 1 hour, washed and transferred to 24-well plates coated with mAb anti-CD3 (OKT; 0.5 µg/ml) in serum-free medium. The supernatants were collected after 24 hr and analyzed for IFN-γ (A), TNF-α (B) and IL-10 (C) secretion. The means±SD of five experiments are shown. *P<0.05.
Figure 24B:
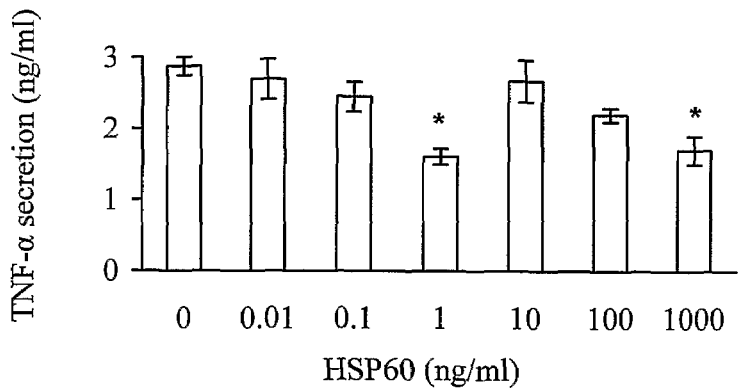
Figure 24C:
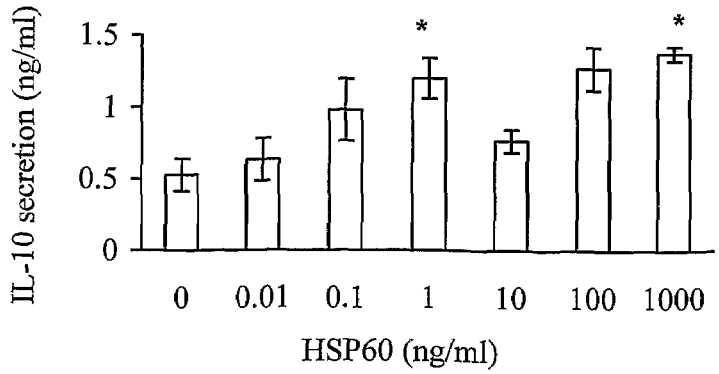

It was previously shown that treatment of human patients or diabetic NOD mice with HSP60 or its bio-active peptide p277 inhibited Th1 autoimmunity and enhanced Th2-like immune responses (Raz et al., 2001; Quintana et al., 2002; Elias et al., 1997). This shift in the cytokine profile was associated with the arrest of inflammatory β-cell destruction in newly diagnosed human subjects with type I diabetes (Raz et al., 2001; Elias et al., 1997). The effects of HSP60 on the cytokine secretion profile of freshly isolated and purified human T cells that were activated by anti-CD3 mAb, were analyzed. HSP60 alone did not induce cytokine secretion from the T cells. However, when the T cells were activated by immobilized anti-CD3, the secretion of the Th1-related cytokines IFN-γ and TNF-α was inhibited by HSP60 (FIGS. 24A and 24B), while IL-10 secretion was enhanced (FIG. 24C). Recently, the inventors have shown that the biological effects of HSP60 on T cells manifested a bell-shaped dose-response curve (Zanin-Zhorov et al., 2003). Interestingly, both the inhibitory effect of HSP60 on IFN-γ and TNF-α secretion and its activation of IL-10 secretion also manifested a bell-shaped dose-response. Significant effects were achieved with relatively low concentrations of HSP60 (0.1-1.0 ng/ml; P<0.05), while higher doses (in the order of 10 ng/ml) did not appear to affect cytokine secretion. However, cytokine secretion was again affected at higher concentrations of HSP60 (0.1-1 μg/ml; P<0.05). Thus, HSP60 can modulate the profiles of Th1 and Th2-associated cytokine secretion in human T cells.

Figure 25A:
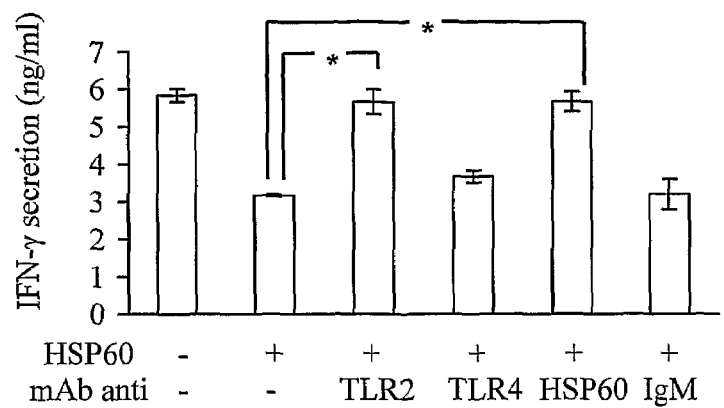
FIG. 25 demonstrates that the effects of HSP60 on T-cell cytokine secretion are TLR2-dependent. Purified human T cells were pretreated with monoclonal anti-TLR2, anti-TLR4 or anti-HSP60 (20 µg/ml, 30 min), and washed. Then, the cells were incubated with HSP60 (1 ng/ml, 1 hr), washed, and exposed to immobilized monoclonal anti-CD3 in serum-free medium. The supernatants were collected after 24 hr and analyzed for IFN-γ (A), TNF-α (B) and IL-10 (C) secretion. The means±SD of three experiments are shown. *P<0.05.
Figure 25B:
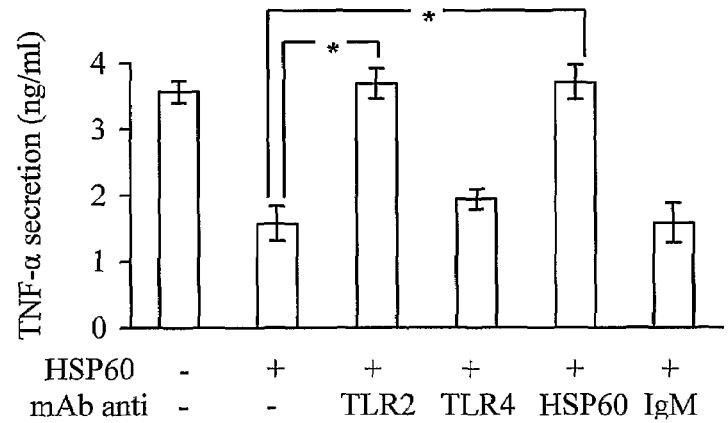
Figure 25C:
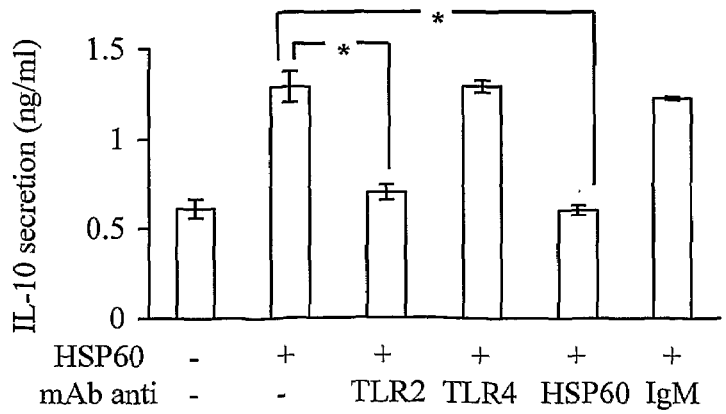

HSP60 has been reported to activate responsive cells via TLR4 or TLR2 signaling (Ohashi et al., 2000; Kol et al., 1998). The inventors have previously reported that HSP60 by TLR2 signaling can induce T-cell adhesion to the extracellular matrix glycoprotein, fibronectin, and inhibit T-cell chemotaxis through fibronectin toward ELC and SDF-1α (CXCL12) (Zanin-Zhorov et al., 2003). To test whether TLR2 or TLR4 was functionally involved in the effects of HSP60 on T-cell cytokines, human T cells were pre-incubated with anti-TLR2 or TLR4 mAb, and their cytokine secretion profile was assessed. The inhibition of IFN-γ and TNF-α secretion (FIG. 25, A and B), or activation of IL-10 secretion (FIG. 25C) by HSP60 was blocked by treating the T cells with a mAb to TLR2, but not by a mAb to TLR4. In addition, the effects of HSP60 on T-cell cytokine secretion were blocked by anti-HSP60 mAb, but not by an isotype-matched control mAb. Thus, TLR2 appears to play a role in mediating the effects of HSP60 on activated human T cells.

Example 28

Figure 26A:
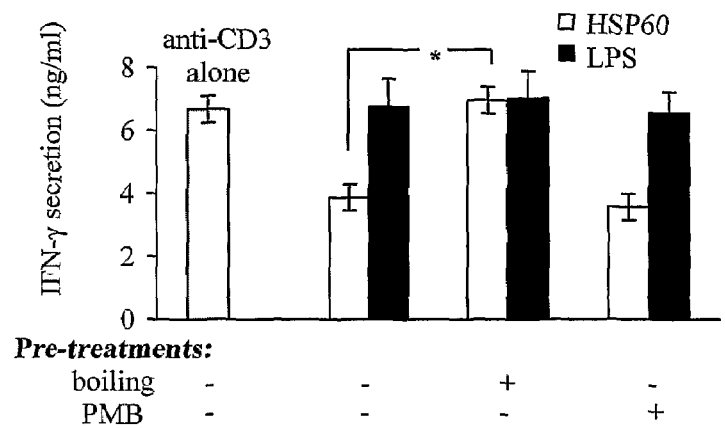
FIG. 26 shows that the effects of HSP60 on cytokine secretion are not due to contaminating LPS. Purified human T cells were treated (1 hr) with HSP60 (0.1 ng/ml) or LPS (100 ng/ml) after pretreatment (30 min) with polymyxin B (PMB; 1 µg/ml). As indicated, the HSP60 and LPS were boiled (100° C., 30 min) in some samples before addition to the to the cell cultures. After washing, the T cells were exposed to immobilized anti-CD3 in serum-free medium. The supernatants were collected after 24 hr and analyzed for IFN-γ (A), TNF-α (B) and IL-10 (C) secretion. The means±SD of three experiments are shown. *P<0.05.
Figure 26B:
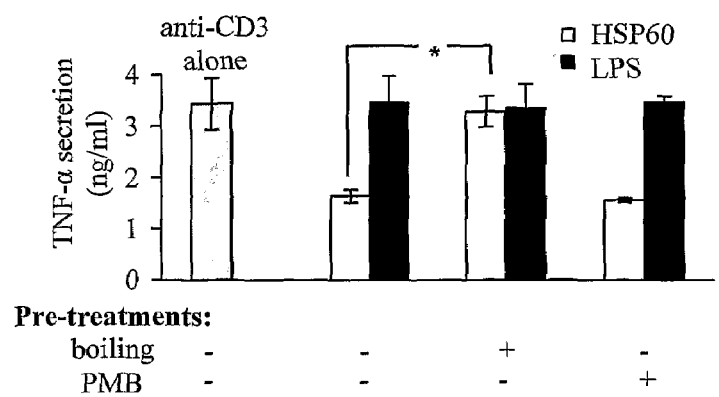
Figure 26C:
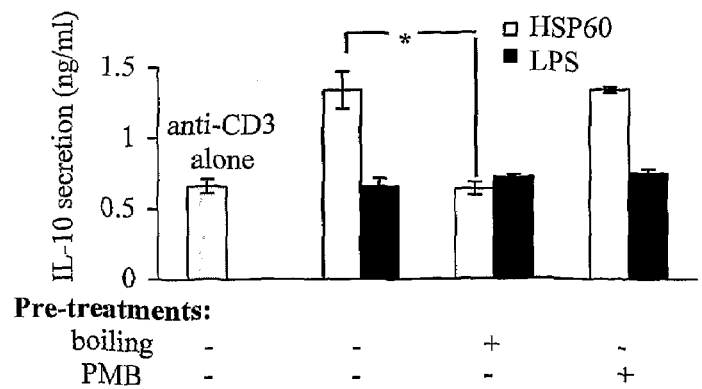

The Effects of HSP60 on T-Cell Cytokine Secretion are not Due to Contaminating LPS LPS-TLR2 interactions can transmit intracellular activation signals in various types of leukocytes. Using a kinetic-turbidimetric test method, it is hereby shown that the recombinant human HSP60 used in this study contained less than 0.001 EU/μg protein (0.1 pg/μg) of bacterial endotoxin. The following studies were performed to further exclude the possibility that even minute amounts of LPS might affect T-cell cytokine secretion using the LPS inhibitor polymyxin B (PMB), and by boiling the HSP60. FIG. 26 shows that the effects of HSP60 on cytokine secretion were completely inhibited by boiling (which denatures proteins, but not LPS), but not by PMB (an inhibitor of LPS). Moreover, in contrast to its effects on macrophages, it is herein demonstrated that purified LPS did not modify T-cell cytokine secretion. Thus, the effects of HSP60 on T-cell cytokine secretion could not be attributed to LPS.

Recently, lipoproteins extracted from the *Escherichia coli* were shown to interact with macrophages via TLR-2 (Gao et al., 2003). Such lipoproteins can be removed from LPS by passage over PMB-coupled agarose beads (Gao et al., 2003). The HSP60 was therefore incubated with PMB-coupled agarose beads, the unbound material was collected, and the protein content assayed, and the effect of the PMB-treated HSP60 on TNFα secretion was tested. Pre-incubation with PMB-conjugated agarose beads did not block the efficacy of our HSP60 preparation on TNFα secretion, but the efficacy of the bacterial preparation was completely abolished. Thus, the effects of HSP60 on cytokine secretion by T cells could be attributed to HSP60 itself.

Example 29

HSP60 Inhibits Nuclear Translocation of NF-κB in T Cells

Figure 27A:
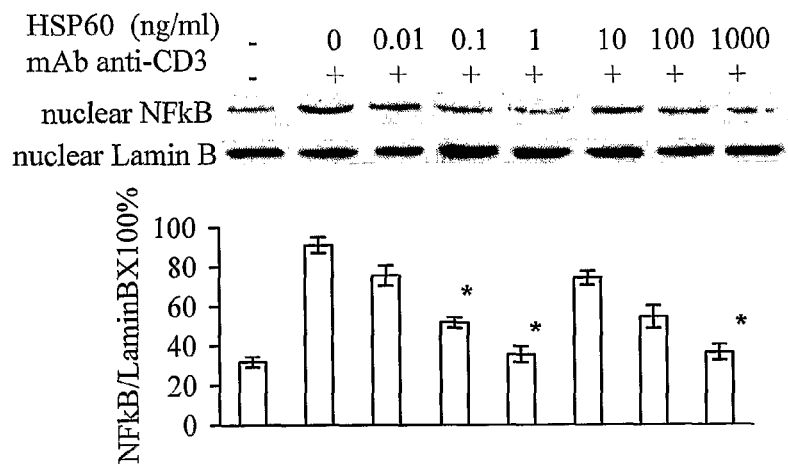
FIG. 27 demonstrates that HSP60 inhibits anti-CD3-induced nuclear translocation of NF-κB in T cells. Purified human T cells were incubated with HSP60 at 0.01-1000 ng/ml for 1 hr (A, B) or with 1 ng/ml for 0-240 min (C). Then, the T cells were washed and exposed to immobilized mAb anti-CD3 (A-C) for 24 hr. Nuclear (A, C) or cytoplasmic (B) lysates were immunoblotted with anti-NF-κB (A-C), anti-Lamin B (A, C), or anti-total ERK (tERK) (B). Abs against Lamin B and tERK served as a control. One experiment representative of three is presented in each case. The levels of NF-κB, Lamin B and tERK were estimated by densitometry and the average percentage of three different experiments was calculated by OD of NF-kB/Lamin B (total ERK)×100%. *P<0.01.
Figure 27B:
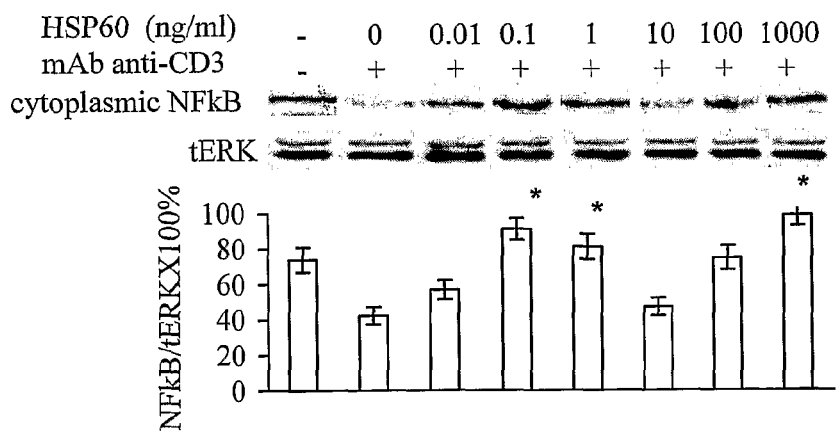
Figure 27C:
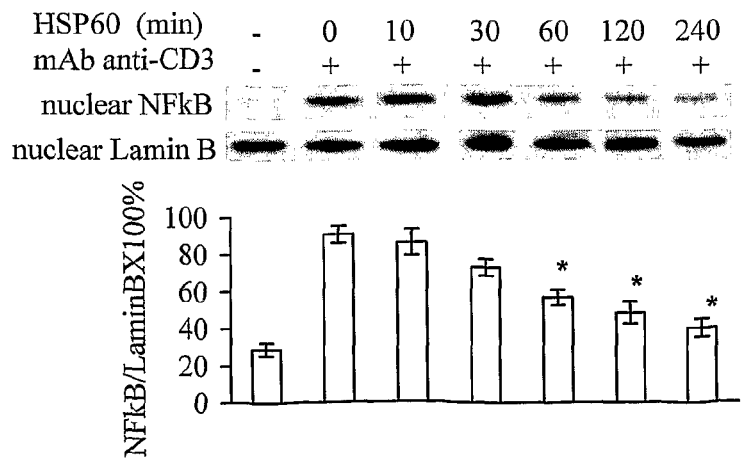

Activation and nuclear translocation of NF-κB is an essential step in the regulation of gene expression and secretion of various pro-inflammatory cytokines in leukocytes, including T cells. To address the modulatory role of HSP60 on the signal transduction cascade leading to regulation of T-cell secretion of TNF-α, IFN-γ, and IL-10, the nuclear translocation of NF-κB was examined by probing nuclear and cytoplasmic T-cell extracts using mAb specific for the p65 subunit of NF-kB. The nuclear protein Lamin B and the cytoplasmic ERK were used as continuatively expressed control proteins, for the quantification of protein amounts (FIG. 27). Treatment of T cells with HSP60 alone did not affect the nuclear translocation of NF-κB. However, pre-treatment of T cells with HSP60, followed by their exposure to anti-CD3, caused a significant down-regulation of NF-kB activation and translocation to the nucleus (FIG. 27A); the p65 subunit of this nuclear factor remained in the cytoplasmic compartment (FIG. 27B). Similar to the results in the cytokine secretion assays (FIG. 24), maximal effects on NF-κB (P<0.01) were observed with 1 ng/ml or 1 μg/ml HSP60 (FIG. 27A). At 1 ng/ml of HSP60, inhibition was already apparent after 60 min (P<0.01), and reached its peak after 120 to 240 min (FIG. 27D).

Example 30

HSP60 Inhibits NFATp Activation in T Cells

Figure 28A:
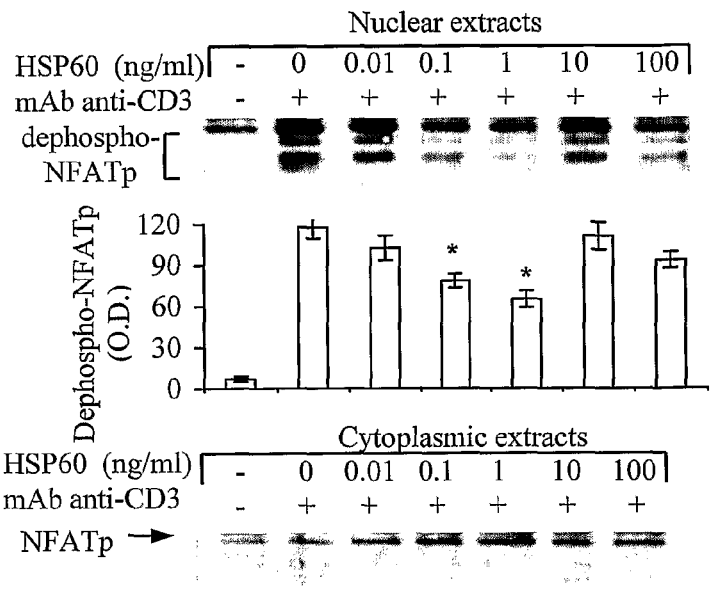
FIG. 28 demonstrates that HSP60 inhibits anti-CD3-induced NFATp activation in T cells. Purified human T cells were incubated with HSP60 at 0.01-100 ng/ml for 1 hr (A) or at 1 ng/ml for 0-240 min (B). In (C), the cells were pre-treated with cycloheximide (CHX; 50 μM, 30 min), and exposed to HSP60 (1 ng/ml, 2 hr). Then, the T cells were washed and exposed to immobilized anti-CD3 for 24 hr. Nuclear (A-C) and cytoplasmic (A) lysates were immunoblotted with anti-NFATp. The upper NFATp band served as a control. One experiment representative of three is presented in each case. The levels of dephospho-NFATp were estimated by densitometry and the average percentage of three different experiments is shown. *P<0.05.
Figure 28B:
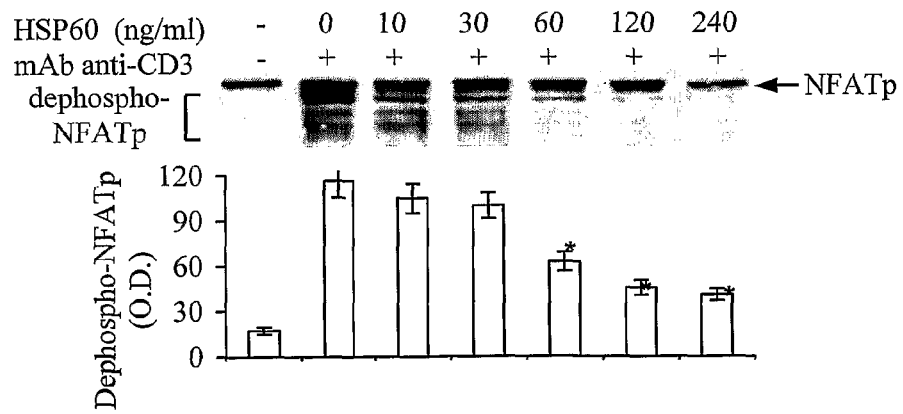

NFAT is a critical regulator of TCR-mediated signals involved in early events associated with gene transcription. Currently, four NFAT genes encoding the cytoplasmic subunits have been characterized: NFATc, NFATp, NFAT3, and NFAT4 (also called NFATc1, NFATc2, NFATc4, and NFATc3, respectively). Several studies indicate that NFATp negatively controls Th2 development. The activation of NFATp and its entry into the nucleus depend on the dephosphorylation of serine/threonine residues, which leads to a 10- to 20-kDa decrease in its apparent molecular mass, as visualized by immunoblots. To study the effects of HSP60 on NFATp activation, the T cells were incubated with HSP60 and immobilized anti-CD3 antibodies, prepared their nuclear extracts, and analyzed the products of activation using immunoblots. Cells that were pre-treated with 1 ng/ml of HSP60 and then exposed to immobilized anti-CD3 antibodies, exhibited a significant down-regulation of their activation and dephosphorylation of NFATp (FIG. 28A). At 1 ng/ml of HSP60, inhibition was apparent after 60 min, and reached its peak after 120 to 240 min (FIG. 28B). In the absence of anti-CD3, HSP60 alone did not affect NFATp phosphorylation.

Figure 28C:
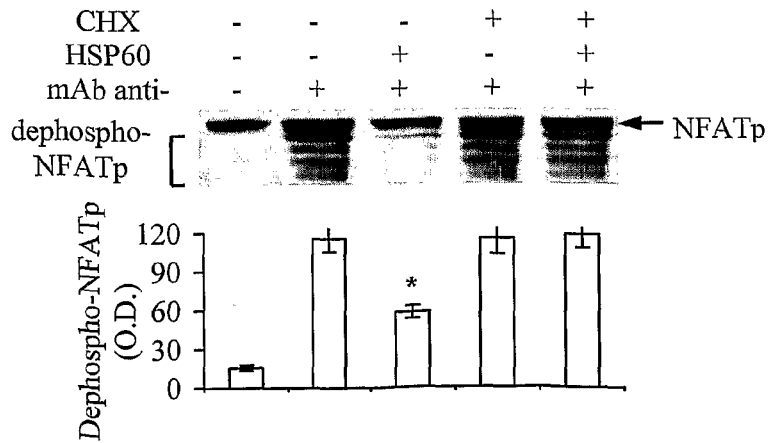

FIG. 28C shows that the inhibitory effect of HSP60 on NFATp dephosphorylation and activation was blocked by the protein synthesis inhibitor cycloheximide (CHX). This is compatible with the conclusion that inhibition of NFATp mediated by HSP60 is an active process.

Example 31

Figure 29A:
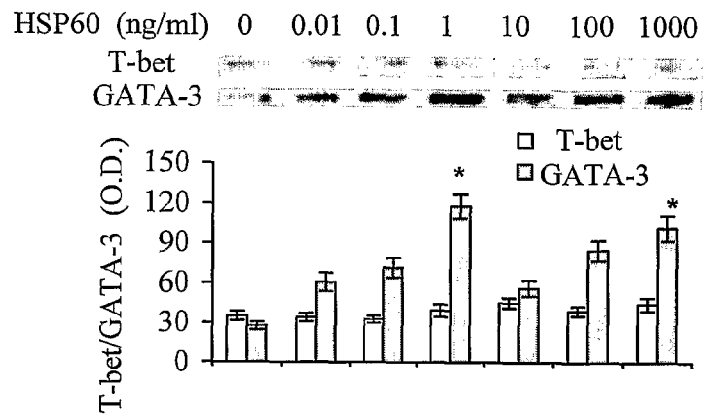
FIG. 29 demonstrates that HSP60 inhibits T-bet and up-regulates GATA-3 expression in TLR-2-dependent signaling. Purified human T cells (A, B, C) or activated mouse lymph node cells (D) were incubated with HSP60 at 0.01-1000 ng/ml for 1 hr (A, B, C). Some cells were pre-treated with anti-TLR2 or anti-TLR4 (20 pg/ml, 30 min), washed and exposed to HSP60 (0.1 ng/ml, 2 hr) (B). Then, the cells were washed and incubated in full medium (A, B, D), or in the presence of immobilized mAb anti-CD3 (C) for 24 hr. Nuclear lysates were immunoblotted with anti-T-bet Ab, stripped, and the same blot was incubated with anti-GATA-3 Ab. One experiment representative of three is presented in each case. The levels of T-bet and GATA-3 were estimated by densitometry and the average percentage derived from three different experiments was shown. *P<0.05.

HSP60 Inhibits T-Bet and Up-Regulates GATA-3 Expression Via TLR2 in Human T Cells HSP60 inhibited the secretion of Th1-associated cytokines IFNγ and TNFα, and increases the secretion of the Th2-associated cytokines IL-10 (FIG. 24), IL-4, and IL-13. Based on these results, it was examined whether HSP60 differentially regulates transcription factors associated with the Th1 and Th2 phenotypes, T-bet and GATA-3. As is demonstrated in FIG. 29A, 1 ng/ml and 1 μg/ml HSP60 significantly (P<0.01) up-regulated the protein level of GATA-3, but not of T-bet. To rule out the possibility that the differences in T-bet and GATA-3 expression were due to unequal amounts of protein loaded on the gel, the same blot was incubated with anti-T-bet and anti-GATA-3 Ab (separated by a stripping procedure). The results confirm that the differences between GATA-3 and T-bet expression were not a result of a difference in protein loading of the gels.

Figure 29B:
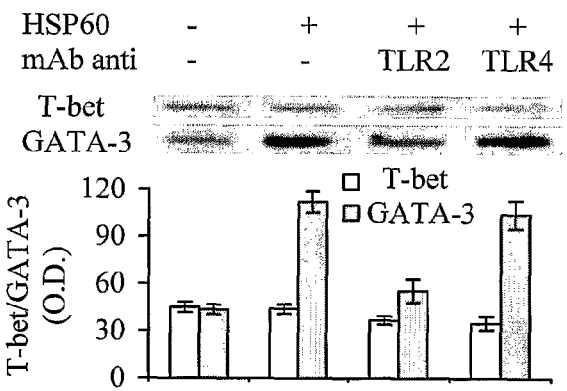

The up-regulation of GATA-3 was TLR2-dependent, since anti-TLR2, but not anti-TLR4 mAb, abrogated the activation by HSP60 (FIG. 29B).

Figure 29C:
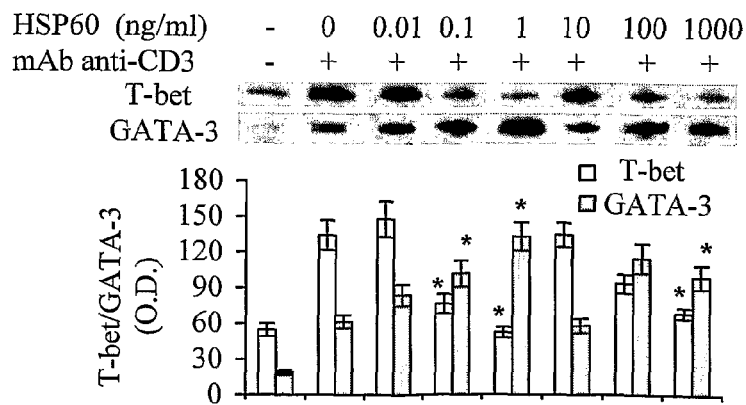
Figure 29D:
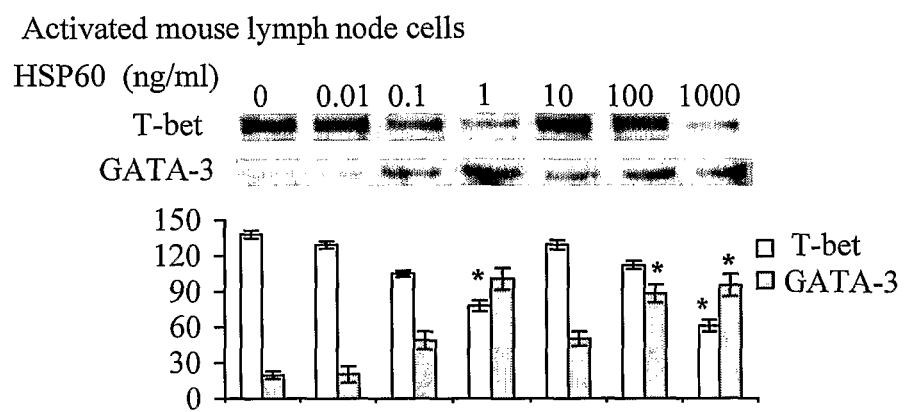

It has been recently reported that the level of T-bet is augmented by TCR-mediated signals. It was also shown that the maximal expression of GATA-3 in human T cells requires stimulatory signals from both TCR and CD28 (Th2-inducing conditions); signaling via TCR alone induces a lesser degree of expression of GATA-3. To analyze the effect of HSP60 on CD3-induced T-bet and GATA-3 expression, the cells were pre-treated with different concentrations of HSP60 (1 hr). The cells were then washed and seeded on immobilized anti-CD3. In the absence of HSP60, expression levels of T-bet were markedly up-regulated in anti-CD3-treated T cells. However, at 1 ng/ml and 1 μg/ml, HSP60 significantly (P<0.05) inhibited the T-bet expression induced by the anti-CD3 (FIG. 29C). As expected, anti-CD3 alone up-regulated the expression of GATA-3 to a much lesser extent, compared to that of T-bet. Furthermore, pre-incubation of T cells with HSP60 significantly up-regulated the expression level of GATA-3. Thus, when the T cells were pre-activated by anti-CD3, HSP60 inhibited the expression of T-bet, but up-regulated that of GATA-3.

Example 32

Figure 30A:
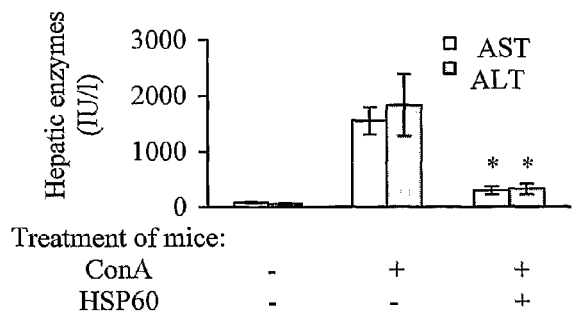
FIG. 30 demonstrates that HSP60 inhibits ConA-induced hepatitis. The levels of hepatic enzymes, AST and ALT (A), and of TNF-α (B) were examined 24 and 2 hr following ConA administration, respectively, in sera obtained from untreated, ConA-treated and HSP60 and ConA-treated BALB/c mice (7 mice per group), (C). Histopathological analysis, using hematoxylin and eosin staining, of liver sections of untreated and treated mice. T cell were purified from the spleens of untreated or treated mice, lysed, and immunoblotted with anti-SOCS3 (D) anti-T-bet, and anti-GATA-3 (E). Each band in the gels is composed of a pool of T-cell lysate from 2 mice. The columns show the levels of SOCS3, T-bet, and GATA-3 expression were estimated by densitometry and the average percentage (±SD) of the various pools was calculated. This experiment was repeated three times, and a representative experiment is shown. *P<0.05.
Figure 30B:
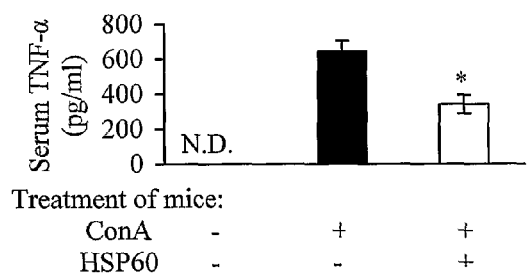

HSP60 Modulates Expression of Th1/Th2 Transcription Factors in Activated Mouse T-Cells The above findings indicated that HSP60 can down-regulate the molecular events leading to Th1 expression and up-regulate those leading to Th2 expression in human T cells in vitro. To test whether HSP60 might exert similar effects in vivo, mouse models were used. The present inventors have previously found that HSP60 abrogated the ability of antigen-reactive T cells to adoptively transfer DTH response to oxazolone in BALB/c mice (WO 03/070761); the DTH reaction is a classical Th1-type immune response that involves the SDF-1α-CXCR4 interaction. This finding suggested that the inhibitory effect of HSP60 on T cell-mediated inflammation might be explained by the ability of HSP60 to down-regulate both T-cell chemotaxis and the secretion of the Th1-type cytokines, TNFα and IFNγ (FIG. 24, A and B). To test this hypothesis, the ability of HSP60 to modulate the expression levels of T-bet and GATA-3 in mouse T cells was examined. Treatment of oxazolone-reactive mouse T cells with 1 ng/ml of HSP60 for 2 hr resulted in down-regulation of T-bet and up-regulation of GATA-3 expression (FIG. 30D). Thus, the inhibitory effect of HSP60 on DTH may be explained not only by its ability to down-regulate the SDF-1α-CXCR4 interactions required for T-cell chemotaxis to inflammatory sites, but also by the ability of HSP60 to shift the transcription factor expression from a Th1 to Th2 pattern.

Example 33

HSP60 Suppresses Th1-Mediated ConA-Induced Hepatic Injury in Mice, Associated with Modulation of Expression of Th1/Th2 Transcription Factors and Cytokines To test whether HSP60 administration could affect inflammatory disease in an in vivo model, the effect of HSP60 on BALB/c mice with acute liver injury induced by intravenous ConA was examined; the liver injury has been shown to be caused by pro-inflammatory CD4+ T cells (Tiegs et ah, 1992). It has also been shown that the level of expression of TNFα and IL-4 are increased following ConA injection, while that of IL-10 is decreased. Down-regulation of SOCS3 is also involved in hepatitis, and SDF-1α-CXCR4 interactions were found to play a major role in the disease.

Here, HSP60 was administered intraperitoneally 1 hr and 18 hr prior to their IV injection with ConA. Control mice were not treated with HSP60. Changes in the secretion profiles of cytokines and a rise in serum levels of liver enzymes were used as markers for the severity of hepatitis; serum cytokines were measured at 2 hr and liver enzymes at 24 hr. Histological analysis of hepatic tissues was also performed 24 hr after ConA administration. HSP60 significantly ($P \leq 0.05$) inhibited the secretion of AST and ALT from the injured livers of the ConA-treated mice (FIG. 30A).

Histopathologic examination of liver sections confirmed that HSP60 administration reduced liver damage. ConA induced a marked inflammatory-cell infiltrate around the central veins and large areas of necrosis in the liver lobules. In contrast, mice treated with HSP60 manifested only minimal liver damage; there were no areas of necrosis and leukocyte infiltration was almost absent (FIG. 30C).

Figure 30C:
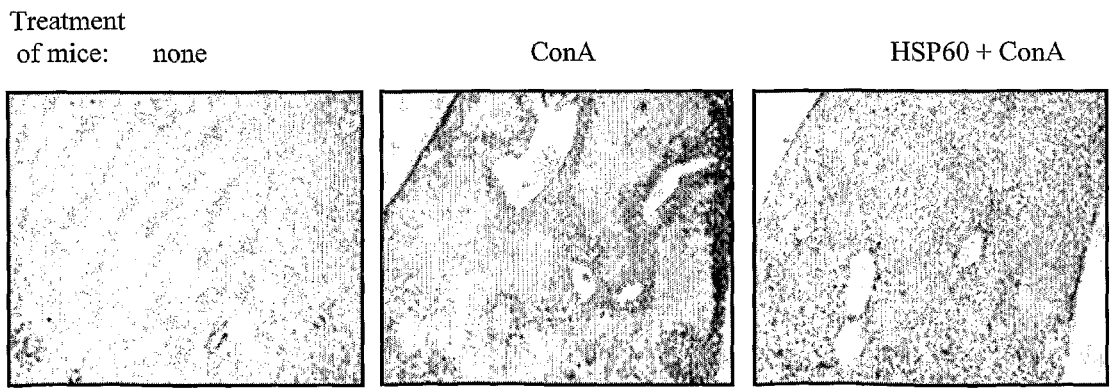
Figure 30D:
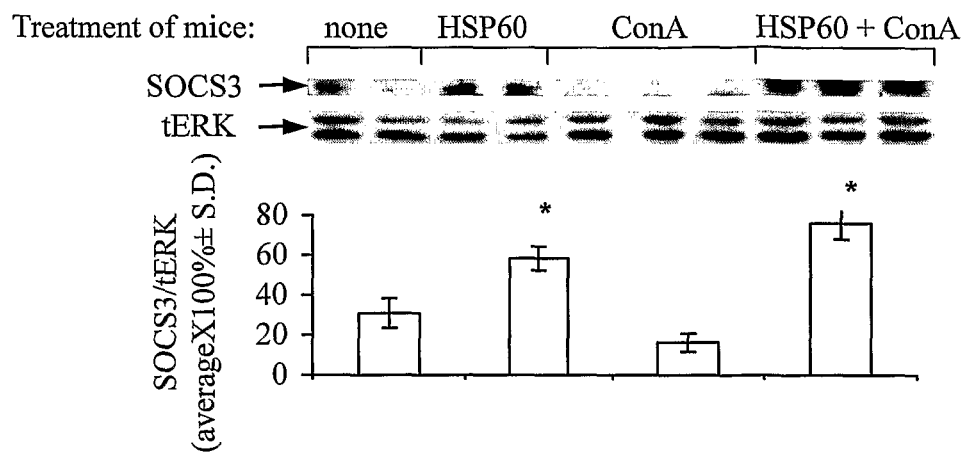

HSP60 also reduced the levels of TNFα in the sera of the mice (FIGS. 30B and 9A), while increasing the level of IL-10 (FIG. 30C).

To assay the effects of HSP60 on the T cells of the mice, T cells were purified from the spleens and the expression of SOCS3, GATA-3, and T-bet in lysates of the T cells was measured. T-cell donor mice were either healthy, treated with HSP60, treated with ConA, or treated with both HSP60 and ConA. SOCS3 expression was minimal in healthy mice, but became elevated following HSP60 treatment, and was even more elevated in the mice treated with both ConA and HSP60 (FIG. 30D). Thus, the suppression of ConA-induced hepatitis was associated with augmentation of SOCS3 expression.

Figure 30E:
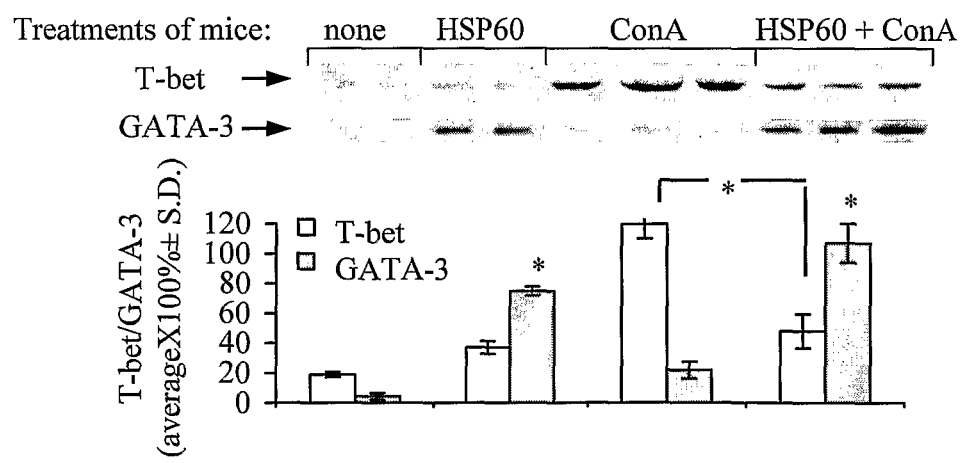

The expression of GATA and T-bet in these mouse T cells was also measured. HSP60 suppressed the ConA-induced expression of the Th1-associated transcription factor T-bet, while significantly augmenting the expression of the Th2-associated factor GATA-3 ($P<0.05$) (FIG. 30E). Thus, HSP60 down-regulates hepatitis in mice by down-regulating the expression of T-bet and up-regulating the expression of GATA-3 and SOCS3, thereby inducing a Th1 to Th2 cytokine shift. These in vivo and ex vivo results in mice confirmed the findings induced by HSP60 in human T cells obtained in vitro.

Figure 31:
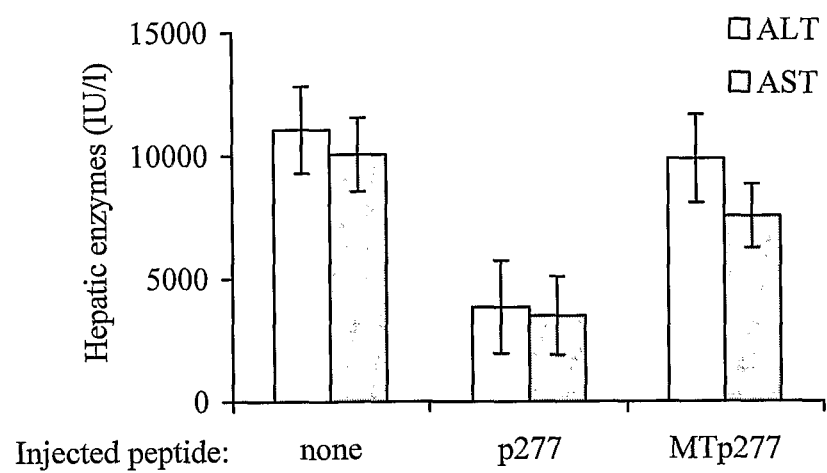
FIG. 31 is a graph showing that p277 inhibits ConA-induced hepatitis. The levels of hepatic enzymes, AST and ALT were examined 24 hr following ConA administration, in sera obtained from untreated, ConA-treated, p277 and ConA-treated, or MTp277 and ConA-treated BALB/c mice.

Example 34 p277 Suppresses Th1-Mediated ConA-Induced Hepatic Injury in Mice Associated with Modulation of Expression of Th1 and Th2 Cytokines The p277 peptide, or a control peptide, MTp277 were injected (330 μl, 500 ng/ml) to BALB/c mice 1 hr and 18 hr prior to ConA treatment. Liver enzymes ALT and AST were measured in sera obtained from the mice 24 hr after ConA administration. p277, but not the control peptide MTp277 significantly inhibited ALT and AST secretion from injured livers of the ConA-treated mice (FIG. 31).

Figure 32A:
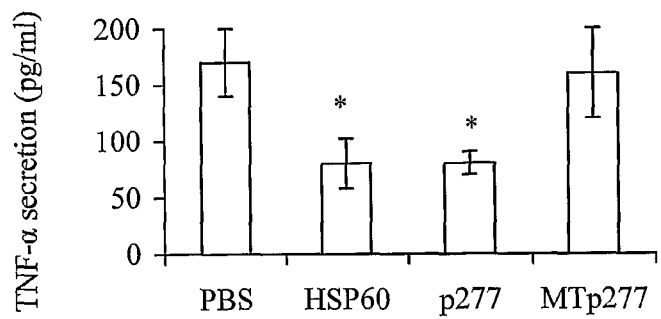
FIG. 32 illustrates that HSP60 and p277 modulate cytokine secretion in ConA-induced hepatitis. The levels of TNF-α (A), IL-6 (B), and IL-10 (C) were examined 2 hr following ConA administration in sera obtained from PBS-, HSP60, p277, and MT-p277-treated BALB/c mice (4 mice per group). *P<0.05.
Figure 32B:
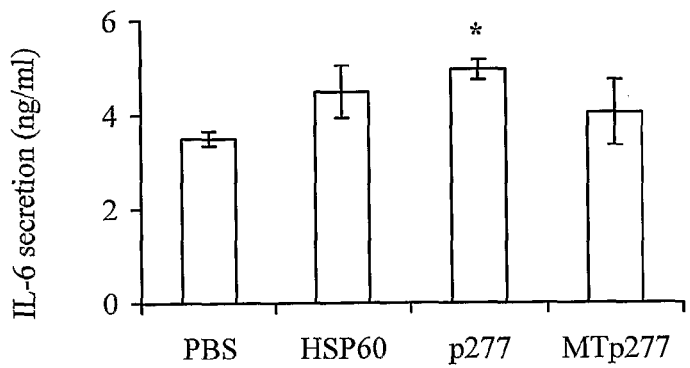
Figure 32C:
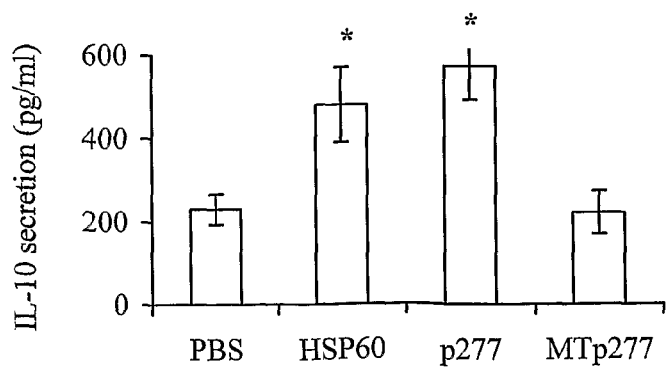

The serum levels of TNF-α and IL-10 were also examined, 2 hr following ConA administration. The levels of TNF-α in the sera were significantly decreased in mice treated with p277, while the level of IL-10 was significantly increased (FIGS. 32A and 32C). The control peptide, MTp277, did not seem to have a significant effect on the levels of cytokines in the sera of ConA-treated mice.

Thus, p277 retains the down-regulating effect of HSP60 on hepatitis in mice, as well as its ability to induce a Th1 to Th2 cytokine shift in ConA-treated mice.

IL-6 is a cytokine secreted by both lymphoid and non-lymphoid cells, which has been implicated in various physiological and pathological processes. IL-6 was previously demonstrated to serve a protective role in ConA-induced hepatitis and other models of liver injury, and to induce a Th1 to Th2 shift by regulating Th1/Th2 transcription factors. Thus, the level of IL-6 in the sera of the mice was assayed. As can be seen in FIG. 32B, p277, and to a lesser extent, HSP60, increased the level of IL-6 in the sera of ConA treated mice.

Example 35

Preparation of T Cell Vaccines

Human T cells are isolated on a Ficoll gradient, washed, and incubated (2 h, 37° C., 7.5% $CO_2$, humidified atmosphere) on petri dishes. The nonadherent cells are then collected and incubated (1 h, 37° C., 7.5% $CO_2$, humidified atmosphere) on nylon wool columns (Novamed, Jerusalem, Israel). Unbound cells are eluted from the columns by extensive washings.

A portion of the cells are activated on anti-CD3 mAb pre-coated 24-well plates (0.5 μg/ml; non tissue culture grade plates), irradiated (5000 rads), and plated in round bottom 96-well microplates $2 \times 10^5$ cells per well in the presence of 10-50 μg/ml p277 and $2 \times 10^5$ untreated T cells per well. The cells are cultured in medium RPMI-1640 (Gibco) supplemented with 10% fetal bovine serum (HyClone), 100 U/ml penicillin, 100 μg/ml streptomycin, and 0.1% glutamine in 37° C., 5% $CO_2$ incubator. Following cultivation for 7-14 days, the cultures are split and subcultures are prepared and re-stimulated with p277-primed T cells as described above. The index of cell stimulation (SI) in response to p277 is examined after additional 72 h in culture using $^3$H-thymidine incorporation assays (Amersham, Arlington Heights, Ill.). Wells exhibiting a minimal SI>3 (threefold increase in $^3$H-thymidine incorporation relative to the average incorporation in reference control wells not stimulated with peptide) are selected for line propagation and expanded with IL-2 (50 IU/ml, Roche).

Example 36

Anti-CD3-Induced T-Cell Proliferation and IFNγ Secretion are Inhibited by p277 Analogs Mice: Female C57BL/6J were purchased from Harlan Olac (Bicester, U.K). The mice were maintained in a specific pathogen-free (SPF) facility in the Weizmann institute, and were used at the age of 5-8 weeks.

Purification of naïve T cells: Mouse spleen-cell suspensions were depleted of red blood cells by treatment with red blood lysis buffer (Sigma, St Louis, USA). T cells were then purified by negative selection with a T-cell isolation kit containing biotin-conjugated monoclonal antibodies to CD11b, CD45R, DX5 and Ter-119 (Miltenyi Biotec, Bergisch Gladbach, Germany). This procedure routinely yielded T cell preparations that were >95% positive for the CD3 marker as determined by FACS analysis.

Cells and medium: The T-cells cultures were set in RPMI-1640 supplemented with 5% FCS (Hyclon Logan, Utah) 100

U/ml penicillin, 100 µg/ml streptomycin, 50 µM 2β-ME, 12.5 mM hepes, 2 mM L-glutamine, 1 mM sodium pyruvate and non essential amino acids (biological industries 01-340-1 diluted 1:100).

Reagents: The peptides used in this Example (VLGGGVALLRVIPALDSLTPANED, p277(Val$^6$Val$^{11}$), SEQ ID NO:2; and VLGGGSALLRSIPALDSLTPANED, p277(Ser$^6$Ser$^{11}$), SEQ ID NO:3) were synthesized using the F-MOC technique with an automatic multiple peptide synthesizer (AMS 422, ABIMED, Langenfeld, Germany). The purity of the peptides was analyzed by HPLC.

The hamster anti-mouse anti-CD3 antibody was collected by TCA precipitation from 2C11 hybridoma supernatant. For the proliferation assay, non-tissue culture-treated polystyrene flat-bottom 96-well microtiter plates (Nunc 269787) were incubated overnight at 4° C. with 0.5-2 µg/ml anti-CD3 antibody.

T-cell proliferation: Mouse splenic purified T cells (1×10$^5$) were pre-incubated with the p277 analogs p277(Val$^6$Val$^{11}$) (SEQ ID NO:2) or p277(Ser$^6$Ser$^{11}$) (SEQ ID NO:3) at the indicated concentrations for 30-60 min, and transferred to anti-CD3 coated wells in triplicate or quadruplicate in 200 µl culture medium. After 72 h of incubation (37° C., 5% CO$_2$) the cells were pulsed with 1 µCi [$^3$H]-thymidine for 7 h, and [$^3$H] thymidine incorporation was measured using a 96-well plate beta-counter. The mean cpm±Standard Error were calculated for each triplicate or quadruplicate.

Interferon-gamma (IFNγ) secretion to the culture media was determined by using an ELISA assay (OptiEIA kits, BD Pharmingen and Pierce Endogen) following the manufacturer's instructions. Standard curves were established using mouse recombinant cytokines. The assay detection limit was 16-32 pg/ml.

The results are presented in Table 1 herein:

TABLE 1

| anti-CD3-induced T-cell proliferation and IFNγ secretion in the presence of p277(Val$^6$Val$^{11}$) or p277(Ser$^6$Ser$^{11}$). | | | | |
|---|---|---|---|---|
| Added peptide | p277(Val$^6$Val$^{11}$) | | p277(Ser$^6$Ser$^{11}$) | |
| Peptide concentration (ng/ml) | Percent Inhibition of proliferation | Percent Inhibition of IFNγ secretion | Percent Inhibition of proliferation | Percent Inhibition of IFNγ secretion |
| 0 | 0% ± 11% | 0% ± 15.2% | 0% ± 9.6% | 0% ± 15% |
| 0.1 | 50% ± 19% | 94% ± 0.81% | 80% ± 2.2% | 86.6% ± 11.3% |
| 1 | 73% ± 7.5% | 88.9% ± 3.4% | 76% ± 8% | 86.4% ± 1.3% |
| 10 | 69% ± 14% | 86.7% ± 8.8% | 68% ± 7.8% | 82.6% ± 4.75% |

The values for antiCD3-induced T-cell proliferation and IFNγ secretion without the presence of p277(Val$^6$Val$^{11}$) or p277(Ser$^6$Ser$^{11}$) were 5879 cpm and 5 ng/ml, respectively.

As can be seen in Table 1, both p277(Val$^6$Val$^{11}$) and p277(Ser$^6$Ser$^{11}$) inhibited T-cell proliferation and IFNγ secretion induced by the anti-CD3 antibody.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

1. Quintana et al., 2000. J Immunol 165:6148-6155.
2. Quintana et al., 2003. J Immunol 171:3533-3541.
3. Anderton et al., 1994. J Immunol 152:3656-3664.
4. van Eden et al., 1988. Nature 331:171-173.
5. Mor et al., 1992. J Clin Invest 90:2447-2455.
6. Quintana et al., 2002. J Immunol 169:6030-6035.
7. Quintana et al., 2002b. J Immunol 169:3422-3428.
8. Ragno et al., 1997. Arthritis Rheum 40:277-283.
9. Wang et al., 2002. Clin. Immunol. 105:199-207.
10. Ferris et al., 1988. Proc Natl Acad Sci USA 85:3850-3854.
11. Reizis et al., 1996. Int Immunol 8:1825-1832.
12. Zanin-Zhorov et al., 2003. Faseb J 17:1567.
13. Zanin-Zhorov et al., 2003b. J Immunol 171:5882.
14. Kollet O et al, 2001. Blood 97:3283.
15. Kol et al., 1999. J Clin Invest 103:571.
16. Kol et al., 1998. Circulation 98:300-307.
17. Ohashi et al., 2000. J Immunol 164:558.
18. Wallin et al., 2002. Trends Immunol 23:130.
19. Yokota et al., 2000. Cell Stress Chaperones 5:337.
20. Xu et al., 2000. Circulation 102:14.
21. Laplante et al., 1998. J Histochem Cytochem 46:1291.
22. Elias et al., 1997. Diabetes 46:758.
23. Raz et al., 2001. Lancet 358:1749.
24. Mosmann, 1983. J Immunol Methods 65:55.
25. Gao et al., 2003. J Biol Chem 278:22523.
26. Ben-Nun et al., 1987. Nature 292:60.
27. Holoshitz. et. al., 1983. Science 219:56.
28. Stewart, J. M. and Young, J. D., 1963. Solid Phase Peptide Synthesis, W. H. Freeman Co. (San Francisco);
29. Meienhofer, 1973. Hormonal Proteins and Peptides, vol. 2, p. 46, Academic Press (New York).
30. Schroder and Lupke, 1965. The Peptides, vol. 1, Academic Press (New York).
31. Sambrook et al., Molecular Cloning: A Laboratory Manual, Cold Spring Harbor Labs Press, 1989.
32. Wolff et al., 1990. Science 247, 1465-1468.
33. Stribling et al., 1992. Proc. Natl. Acad. Sci. USA 189:11277-11281.
34. Achiron et al., 2004. Clin. Immunol: 113 155160.
35. Tiegs et al., 1992. J. Clinic. Invest. 90:196-203.
36. Heneghan et al., 2002. Hepatology 35:7.
37. Chedid et al., 1993. Gastroenterology 105:254.
38. Rosen et al., 2002. Hepatology 35:190.
39. Hu et al., 1998. Eur. J. Immunol. 28:2444-2455.

The invention claimed is:

1. A method of treating hepatitis comprising administering to a subject in need thereof a pharmaceutical composition comprising as an active ingredient a therapeutically effective amount of an HSP60 fragment analog or salts thereof, wherein the HSP60 fragment analog has the amino acid sequence as set forth in SEQ ID NO:3, and a pharmaceutically acceptable carrier or diluent.

2. The method of claim 1, wherein the composition comprises a sustained release formulation.

3. The method of claim 2, wherein the active ingredient consists of the amino acid sequence as set forth in any one of SEQ ID NO:3.

4. The method of claim 1, wherein the active ingredient consists of the amino acid sequence as set forth in SEQ ID NO:3.

5. A method of treating or preventing liver damage comprising administering to a subject in need thereof a pharmaceutical composition comprising as an active ingredient a therapeutically effective amount of an HSP60 fragment analog or salts thereof, wherein the HSP60 fragment analog has the amino acid sequence as set forth in SEQ ID NO:3, and a pharmaceutically acceptable carrier or diluent.

6. The method of claim 5, wherein the subject in need thereof is afflicted with a disease selected from: (i) viral hepatitis (ii) parasitic hepatitis (iii) autoimmune hepatitis (iv) primary biliary cirrhosis (v) alcoholic liver disease.

* * * * *

SEQUENCE LISTING

<160> NUMBER OF SEQ ID NOS: 16

<210> SEQ ID NO 1
<211> LENGTH: 24
<212> TYPE: PRT
<213> ORGANISM: Artificial Sequence
<220> FEATURE:
<223> OTHER INFORMATION: SYNTHETIC PEPTIDE

<400> SEQUENCE: 1

Val Leu Gly Gly Gly Cys Ala Leu Leu Arg Cys Ile Pro Ala Leu Asp
1               5                   10                  15

Ser Leu Thr Pro Ala Asn Glu Asp
            20

<210> SEQ ID NO 2
<211> LENGTH: 24
<212> TYPE: PRT
<213> ORGANISM: Artificial Sequence
<220> FEATURE:
<223> OTHER INFORMATION: synthetic peptide

<400> SEQUENCE: 2

Val Leu Gly Gly Gly Val Ala Leu Leu Arg Val Ile Pro Ala Leu Asp
1               5                   10                  15

Ser Leu Thr Pro Ala Asn Glu Asp
            20

<210> SEQ ID NO 3
<211> LENGTH: 24
<212> TYPE: PRT
<213> ORGANISM: Artificial Sequence
<220> FEATURE:
<223> OTHER INFORMATION: synthetic peptide

<400> SEQUENCE: 3

Val Leu Gly Gly Gly Ser Ala Leu Leu Arg Ser Ile Pro Ala Leu Asp
1               5                   10                  15

Ser Leu Thr Pro Ala Asn Glu Asp
            20

<210> SEQ ID NO 4
<211> LENGTH: 573
<212> TYPE: PRT
<213> ORGANISM: Homo sapiens

<400> SEQUENCE: 4

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

```
Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
        130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
                180                 185                 190

Val Gly Arg Lys Gly Val Ile Thr Val Lys Asp Gly Lys Thr Leu Asn
            195                 200                 205

Asp Glu Leu Glu Ile Ile Glu Gly Met Lys Phe Asp Arg Gly Tyr Ile
        210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
        290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
        340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
        370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
                420                 425                 430

Glu Glu Gly Ile Val Leu Gly Gly Gly Cys Ala Leu Leu Arg Cys Ile
            435                 440                 445

Pro Ala Leu Asp Ser Leu Thr Pro Ala Asn Glu Asp Gln Lys Ile Gly
        450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Val
```

```
                    530                 535                 540
Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565                 570

<210> SEQ ID NO 5
<211> LENGTH: 72
<212> TYPE: DNA
<213> ORGANISM: Artificial Sequence
<220> FEATURE:
<223> OTHER INFORMATION: synthetic oligonucleotide

<400> SEQUENCE: 5
gttttgggag ggggttgtgc cctccttcga tgcattccag ccttggactc attgactcca      60
gctaatgaag at                                                         72

<210> SEQ ID NO 6
<211> LENGTH: 72
<212> TYPE: DNA
<213> ORGANISM: Artificial Sequence
<220> FEATURE:
<223> OTHER INFORMATION: synthetic oligonucleotide

<400> SEQUENCE: 6
gttttgggag gggtgttgc cctccttcga gtcattccag ccttggactc attgactcca       60
gctaatgaag at                                                         72

<210> SEQ ID NO 7
<211> LENGTH: 72
<212> TYPE: DNA
<213> ORGANISM: Artificial Sequence
<220> FEATURE:
<223> OTHER INFORMATION: synthetic oligonucleotide

<400> SEQUENCE: 7
gttttgggag gggttctgc cctccttcga tccattccag ccttggactc attgactcca       60
gctaatgaag at                                                         72

<210> SEQ ID NO 8
<211> LENGTH: 2202
<212> TYPE: DNA
<213> ORGANISM: Homo sapiens

<400> SEQUENCE: 8
cacgcttgcc gccgccccgc agaaatgctt cggttaccca cagtctttcg ccagatgaga      60
ccggtgtcca gggtactggc tcctcatctc actcgggctt atgccaaaga tgtaaaattt     120
ggtgcagatg cccgagcctt aatgcttcaa ggtgtagacc ttttagccga tgctgtggcc     180
gttacaatgg ggccaaaggg aagaacagtg attattgagc agggttgggg aagtcccaaa     240
gtaacaaaag atggtgtgac tgttgcaaag tcaattgact taaaagataa atacaagaac     300
attggagcta aacttgttca agatgttgcc aataacacaa atgaagaagc tggggatggc     360
actaccactg ctactgtact ggcacgctct atagccaagg aaggcttcga aagattagc      420 aaaggtgcta atccagtgga atcaggaga ggtgtgatgt tagctgttga tgctgtaatt     480
gctgaactta aaaagcagtc taaacctgtg accaccctg aagaaattgc acaggttgct     540
acgatttctg caaacggaga caaagaaatt ggcaatatca tctctgatgc aatgaaaaaa     600
gttggaagaa agggtgtcat cacagtaaag gatggaaaaa cactgaatga tgaattagaa     660
```

-continued

```
attattgaag gcatgaagtt tgatcgaggc tatatttctc catactttat taatacatca    720
aaaggtcaga aatgtgaatt ccaggatgcc tatgttctgt tgagtgaaaa gaaaatttct    780
agtatccagt ccattgtacc tgctcttgaa attgccaatg ctcaccgtaa gcctttggtc    840
ataatcgctg aagatgttga tggagaagct ctaagtacac tcgtcttgaa taggctaaag    900
gttggtcttc aggttgtggc agtcaaggct ccagggtttg gtgacaatag aaagaaccag    960
cttaaagata tggctattgc tactggtggt gcagtgtttg gagaagaggg attgaccctg   1020
aatcttgaag acgttcagcc tcatgactta ggaaaagttg agaggtcat tgtgaccaaa    1080 gacgatgcca tgctcttaaa aggaaaaggt gacaaggctc aaattgaaaa acgtattcaa   1140
gaaatcattg agcagttaga tgtcacaact agtgaatatg aaaggaaaa actgaatgaa     1200 cggcttgcaa aactttcaga tggagtggct gtgctgaagg ttggtgggac aagtgatgtt   1260
gaagtgaatg aaaagaaaga cagagttaca gatgccctta atgctacaag agctgctgtt   1320
gaagaaggca ttgttttggg aggggggttgt gccctccttc gatgcattcc agccttggac   1380
tcattgactc cagctaatga agatcaaaaa attggtatag aaattattaa agaacactc    1440 aaaattccag caatgaccat tgctaagaat gcaggtgttg aaggatcttt gatagttgag   1500
aaaattatgc aaagttcctc agaagttggt tatgatgcta tggctggaga ttttgtgaat   1560
atggtggaaa aaggaatcat tgacccaaca aaggttgtga aactgctttt attggatgct   1620
gctggtgtgg cctctctgtt aactacagca gaagttgtag tcacagaaat tcctaaagaa   1680
gagaaggacc ctggaatggg tgcaatgggt ggaatgggag gtggtatggg aggtggcatg   1740
ttctaactcc tagactagtg ctttaccttt attaatgaac tgtgacagga gcccaaggc    1800 agtgttcctc accaataact tcagagaagt cagttggaga aaatgaagaa aaaggctggc   1860
tgaaaatcac tataaccatc agttactggt ttcagttgac aaaatatata atggtttact   1920
gctgtcattg tccatgccta cagataattt attttgtatt tttgaataaa aacatttgt    1980 acattcctga tactgggtac aagagccatg taccagtgta ctgctttcaa cttaaatcac   2040
tgaggcattt ttactactat tctgttaaaa tcaggatttt agtgcttgcc accaccagat   2100
gagaagttaa gcagcctttc tgtggagagt gagaataatt gtgtacaaag tagaagaagta  2160 tccaattatg tgacaacctt tgtgtaataa aaattttgttt aa                      2202
```

<210> SEQ ID NO 9
<211> LENGTH: 548
<212> TYPE: PRT
<213> ORGANISM: Escherichia coli

<400> SEQUENCE: 9

| Met | Ala | Ala | Lys | Asp | Val | Lys | Phe | Gly | Asn | Asp | Ala | Arg | Val | Lys | Met |
|---|---|---|---|---|---|---|---|---|---|---|---|---|---|---|---|
| 1 | | | | 5 | | | | | 10 | | | | | 15 | |

| Leu | Arg | Gly | Val | Asn | Val | Leu | Ala | Asp | Ala | Val | Lys | Val | Thr | Leu | Gly |
|---|---|---|---|---|---|---|---|---|---|---|---|---|---|---|---|
| | | | 20 | | | | | 25 | | | | | 30 | | |

| Pro | Lys | Gly | Arg | Asn | Val | Val | Leu | Asp | Lys | Ser | Phe | Gly | Ala | Pro | Thr |
|---|---|---|---|---|---|---|---|---|---|---|---|---|---|---|---|
| | | | 35 | | | | | 40 | | | | | 45 | | |

| Ile | Thr | Lys | Asp | Gly | Val | Ser | Val | Ala | Arg | Glu | Ile | Glu | Leu | Glu | Asp |
|---|---|---|---|---|---|---|---|---|---|---|---|---|---|---|---|
| | 50 | | | | | 55 | | | | | 60 | | | | |

| Lys | Phe | Glu | Asn | Met | Gly | Ala | Gln | Met | Val | Lys | Glu | Val | Ala | Ser | Lys |
|---|---|---|---|---|---|---|---|---|---|---|---|---|---|---|---|
| 65 | | | | | 70 | | | | | 75 | | | | | 80 |

| Ala | Asn | Asp | Ala | Ala | Gly | Asp | Gly | Thr | Thr | Thr | Ala | Thr | Val | Leu | Ala |
|---|---|---|---|---|---|---|---|---|---|---|---|---|---|---|---|
| | | | | 85 | | | | | 90 | | | | | 95 | |

| Gln | Ala | Ile | Ile | Thr | Glu | Gly | Leu | Lys | Ala | Val | Ala | Ala | Gly | Met | Asn |
|---|---|---|---|---|---|---|---|---|---|---|---|---|---|---|---|
| | | | 100 | | | | | 105 | | | | | 110 | | |

Pro Met Asp Leu Lys Arg Gly Ile Asp Lys Ala Val Thr Val Ala Val
        115                 120                 125

Glu Glu Leu Lys Ala Leu Ser Val Pro Cys Ser Asp Ser Lys Ala Ile
        130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
        210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
        290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
        370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
        450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met

Gly Gly Met Met
545

<210> SEQ ID NO 10
<211> LENGTH: 22
<212> TYPE: PRT
<213> ORGANISM: Artificial Sequence
<220> FEATURE:
<223> OTHER INFORMATION: synthetic peptide

<400> SEQUENCE: 10

Val Ala Gly Gly Gly Val Thr Leu Leu Gln Ala Ala Pro Thr Leu Asp
1               5                   10                  15

Glu Leu Lys Leu Glu Gly
            20

<210> SEQ ID NO 11
<211> LENGTH: 573
<212> TYPE: PRT
<213> ORGANISM: Homo sapiens

<400> SEQUENCE: 11

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Gly Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

```
Ile Ile Ala Glu Asp Val Asp Gly Glu Ala Leu Ser Thr Leu Val Leu
        275                 280                 285

Asn Arg Leu Lys Val Gly Leu Gln Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Gly Leu Thr Leu Asn Leu Glu Asp
                325                 330                 335

Val Gln Pro His Asp Leu Gly Lys Val Gly Glu Val Ile Val Thr Lys
                340                 345                 350

Asp Asp Ala Met Leu Leu Lys Gly Lys Gly Asp Lys Ala Gln Ile Glu
                355                 360                 365

Lys Arg Ile Gln Glu Ile Ile Glu Gln Leu Asp Val Thr Thr Ser Glu
370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
                500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
        530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570
```

<210> SEQ ID NO 12
<211> LENGTH: 21
<212> TYPE: PRT
<213> ORGANISM: Artificial Sequence
<220> FEATURE:
<223> OTHER INFORMATION: synthetic peptide

<400> SEQUENCE: 12

```
Phe Asn Glu Glu Thr Val Ser Phe Trp Leu Arg Val Pro Lys Val Ser
1               5                   10                  15

Ala Ser His Leu Glu
            20
```

<210> SEQ ID NO 13
<211> LENGTH: 21
<212> TYPE: DNA
<213> ORGANISM: Artificial Sequence
<220> FEATURE:
<223> OTHER INFORMATION: synthetic oligonucleotide

```
<400> SEQUENCE: 13
aagagcgagt accagctggt g                                              21

<210> SEQ ID NO 14
<211> LENGTH: 15
<212> TYPE: PRT
<213> ORGANISM: Artificial Sequence
<220> FEATURE:
<223> OTHER INFORMATION: synthetic peptide

<400> SEQUENCE: 14

Glu Glu Ser Asn Thr Phe Gly Leu Gln Leu Glu Leu Thr Glu Gly
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: synthetic peptide

<400> SEQUENCE: 15

Ala Tyr Asp Glu Glu Ala Arg Arg Gly Leu Glu Arg Gly Leu Asn Ala
1               5                   10                  15

Leu Ala Asp Ala
            20

<210> SEQ ID NO 16
<211> LENGTH: 20
<212> TYPE: PRT
<213> ORGANISM: Artificial Sequence
<220> FEATURE:
<223> OTHER INFORMATION: synthetic peptide

<400> SEQUENCE: 16

Lys Phe Gly Ala Asp Ala Arg Ala Leu Met Leu Gln Gly Val Asp Leu
1               5                   10                  15

Leu Ala Asp Ala
            20
```